(12) United States Patent
Ikuma et al.

(10) Patent No.: US 12,150,941 B2
(45) Date of Patent: *Nov. 26, 2024

(54) PROCESS FOR PREPARING SUBSTITUTED PYRAZOLO[1,5-a]PYRAZINES

(71) Applicant: Sumitomo Pharma Co., Ltd., Osaka (JP)

(72) Inventors: Yohei Ikuma, Osaka (JP); Kengo Tojo, Osaka (JP); Ryo Fukazawa, Osaka (JP); Shuji Masumoto, Osaka (JP)

(73) Assignee: SUMITOMO PHARMA CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/120,519

(22) Filed: Mar. 13, 2023

(65) Prior Publication Data

US 2023/0210850 A1    Jul. 6, 2023

Related U.S. Application Data

(63) Continuation of application No. 16/764,962, filed as application No. PCT/JP2018/043094 on Nov. 22, 2018, now Pat. No. 11,633,395.

(30) Foreign Application Priority Data

Nov. 24, 2017   (JP) .................................. 2017-225364

(51) Int. Cl.
  *C07D 487/04*   (2006.01)
  *A61K 31/4985*  (2006.01)
  *A61P 25/28*    (2006.01)
  *C07D 519/00*   (2006.01)

(52) U.S. Cl.
  CPC .......... *A61K 31/4985* (2013.01); *A61P 25/28* (2018.01); *C07D 519/00* (2013.01)

(58) Field of Classification Search
  CPC .................................................. C07D 487/04
  USPC ....................................................... 544/350
  See application file for complete search history.

(56) References Cited

U.S. PATENT DOCUMENTS

| 10,189,843 B2 | 1/2019 | Nagano et al. |
| 2013/0345204 A1 | 12/2013 | Conn et al. |
| 2015/0361081 A1 | 12/2015 | Conn et al. |
| 2016/0052937 A1 | 2/2016 | Takaishi et al. |
| 2020/0345729 A1 | 11/2020 | Ikuma et al. |

FOREIGN PATENT DOCUMENTS

| AR | 10105 | 11/2016 |
| JP | 2013-189395 | 9/2013 |
| JP | 2015-10745 | 1/2015 |
| JP | 2016-124810 | 7/2016 |
| JP | 2019-182784 | 10/2019 |
| JP | 2020-193176 | 12/2020 |
| JP | 2020-196709 | 12/2020 |
| WO | 2006/030847 | 3/2006 |
| WO | 2006/050803 | 5/2006 |
| WO | 2006/084634 | 8/2006 |
| WO | 2007/039439 | 4/2007 |
| WO | 2008/011560 | 1/2008 |
| WO | 2009/062676 | 5/2009 |
| WO | 2010/060589 | 6/2010 |
| WO | 2013/066736 | 5/2013 |
| WO | 2013/174822 | 11/2013 |
| WO | 2014/133022 | 3/2014 |
| WO | 2014/064028 | 5/2014 |
| WO | 2014/195311 | 12/2014 |
| WO | 2015/129821 | 9/2015 |
| WO | 2016/016380 | 2/2016 |
| WO | 2016/016381 | 2/2016 |
| WO | 2016/016382 | 2/2016 |
| WO | 2016/016383 | 2/2016 |
| WO | 2016/016395 | 2/2016 |
| WO | 2016/027844 | 2/2016 |
| WO | 2016/087487 | 6/2016 |
| WO | 2016/087489 | 6/2016 |
| WO | 2017/018475 | 2/2017 |
| WO | 2017/103179 | 6/2017 |

(Continued)

OTHER PUBLICATIONS

Hemstapat et al., "A Novel Family of Potent Negative Allosteric Modulators of Group II Metabotropic Glutamate Receptors", The Journal of Pharmacology and Experimental Therapeutics, 2007, vol. 322, pp. 254-264.

(Continued)

*Primary Examiner* — Douglas M Willis
(74) *Attorney, Agent, or Firm* — WENDEROTH, LIND & PONACK, L.L.P.

(57) ABSTRACT

A process for preparing a compound of Formula (1a):

(1a)

or a pharmaceutically acceptable salt thereof.

6 Claims, 3 Drawing Sheets

(56) References Cited

FOREIGN PATENT DOCUMENTS

| WO | 2017/103182 | 6/2017 |
|---|---|---|
| WO | 2018/079628 | 5/2018 |
| WO | 2018/192864 | 10/2018 |
| WO | 2019/098211 | 5/2019 |

OTHER PUBLICATIONS

Lundström et al., "Structural determinants of allosteric antagonism at metabotropic glutamate receptor 2: mechanistic studies with new potent negative allosteric modulators", British Journal of Pharmacology, 2011, vol. 164, pp. 521-537.

Doré et al, "Structure of class C GPCR metabotropic glutamate receptor 5 transmembrane domain", Nature, 2014, vol. 511, pp. 557-562.

Chaki et al., "mGlu2/3 and mGlu5 receptors: Potential targets for novel antidepressants", Neuropharmacology, 2013, vol. 66, pp. 40-52.

Higgins et al., "Pharmacological manipulation of mGlu2 receptors influences cognitive performance in the rodent", Neuropharmacology, 2004, vol. 46, pp. 907-917.

International Search Report issued Feb. 12, 2019 in International (PCT) Application No. PCT/JP2018/043094.

Durand et al., "mGlu3 receptor and astrocytes: Partners in neuroprotection", Neuropharmacology, 2013, Vol. 66, pp. 1-11.

Engers et al., "Discovery of a Selective and CNS Penetrant Negative Allosteric Modulator of Metabotropic Glutamate Receptor Subtype 3 with Antidepressant and Anxiolytic Activity in Rodents", Journal of Medicinal Chemistry, 2015, vol. 58, pp. 7485-7500.

Barsanti et al., "Structure-Based Drug Design of Novel Potent and Selective Tetrahydropyrazolo[1,5-a]pyrazines as ATR Inhibitors", ACS Medicinal Chemistry Letters, 2014, vol. 6, pp. 37-41.

Chervyakov et al., "Synthesis of 8-Aroylpyrrolo[1,2-a]pyrazine-1,6,7(2H)-triones and Their Reaction with Water. New Analogs of Cyclic Dipeptides", Russian Journal of Organic Chemistry, 2015, vol. 51, No. 11, pp. 1587-1592.

Micheli et al., "From pyrroles to pyrrolo[1,2-a]pyrazinones: A new class of mGluR1 antagonists", Bioorganic & Medicinal Chemistry Letters, 2006, vol. 16, pp. 1342-1345.

International Preliminary Report on Patentability issued May 26, 2020 in International (PCT) Application No. PCT/JP2018/043094.

Office Action issued Dec. 10, 2020 in continuation U.S. Appl. No. 16/996,314.

Jordan, V.C., "Tamoxifen: A Most Unlikely Pioneering Medicine", Nature Reviews: Drug Discovery, 2003, vol. 2, pp. 205-213.

Hackam et al., "Translation of Research Evidence From Animals to Humans", JAMA, 2006, vol. 296, No. 14, pp. 1731-1732.

Extended European Search Report issued Jun. 4, 2021 in European Patent Application No. 18882052.6.

Chinese Search Report dated Sep. 9, 2022 in Chinese Patent Application No. 201880087389.4, with English translation.

Yi-lei Yang et al., "Research progress of selective mGluR1 antagonists", Acta Pharmaceutica Sinica, 2011, vol. 46, No. 10, pp. 1167-1172, with English Abstract.

Zhang, X., et al., "Synthesis and Preliminary Studies of a Novel Negative Allosteric Modulator, 7-((2,5-Dioxopyrrolidin-1-yl)methyl)-4-(2-fluoro-4-[$^{11}$C]methoxyphenyl)quinoline-2-carboxamide, for Imaging of Metabotropic Glutamate Receptor 2", ACS Chem. Neurosci., 2017, vol. 8, pp. 1937-1948.

Meng-Lin Li et al., "Perspectives on the mGluR2/3 agonists as a therapeutic target for schizophrenia: still promising or a dead end?", Prog. Neuropsychopharmacol Biol Psychiatry, Jul. 3, 2015, vol. 60, pp. 66-76.

Qunies, A.M., et al., "Negative allosteric modulators of group II metabotropic glutamate receptors: A patent review (2015-present)", Expert Opinion on Therapeutic Patents, Mar. 31, 2021, vol. 31, Issue 8, pp. 687-708, English Abstract.

Office Action issued Mar. 7, 2023 in Japanese Patent Application No. 2020-093919, with English-language translation.

Hiyoshi, Tetsuaki et al., "Discovery of novel antipsychotics targeting group II metabotropic glutamate receptor", Folia Pharmacologica Japonica, 2012, vol. 140, pp. 111-115.

Wierońska, Joanna M. et al., "The reversal of cognitive, but not negative or positive symptoms of schizophrenia, by the mGlu$_{2/3}$ receptor agonist, LY379268, is 5-HT$_{1A}$ dependent", Behavioural Brain Research, 2013, vol. 256, pp. 298-304.

Shigeyuki Chaki, "mGlu2/3 Receptor Antagonists as Novel Antidepressants", Trends in Pharmacol. Sci. (2017), vol. 38, No. 6, pp. 569-580.

Donald C. Goff et al., "A Placebo-Controlled Pilot Study of the Ampakine CX516 Added to Clozapine in Schizophrenia", J. Clin. Psychopharmacol. (2001), vol. 21, No. 5, pp. 484-487.

Brooke M. Roberts et al., "Prevention of ketamine-induced working memory impairments by AMPA potentiators in a nonhuman primate model of cognitive dysfunction", Behav. Brain Res. (2010), vol. 212, No. 1, pp. 41-48.

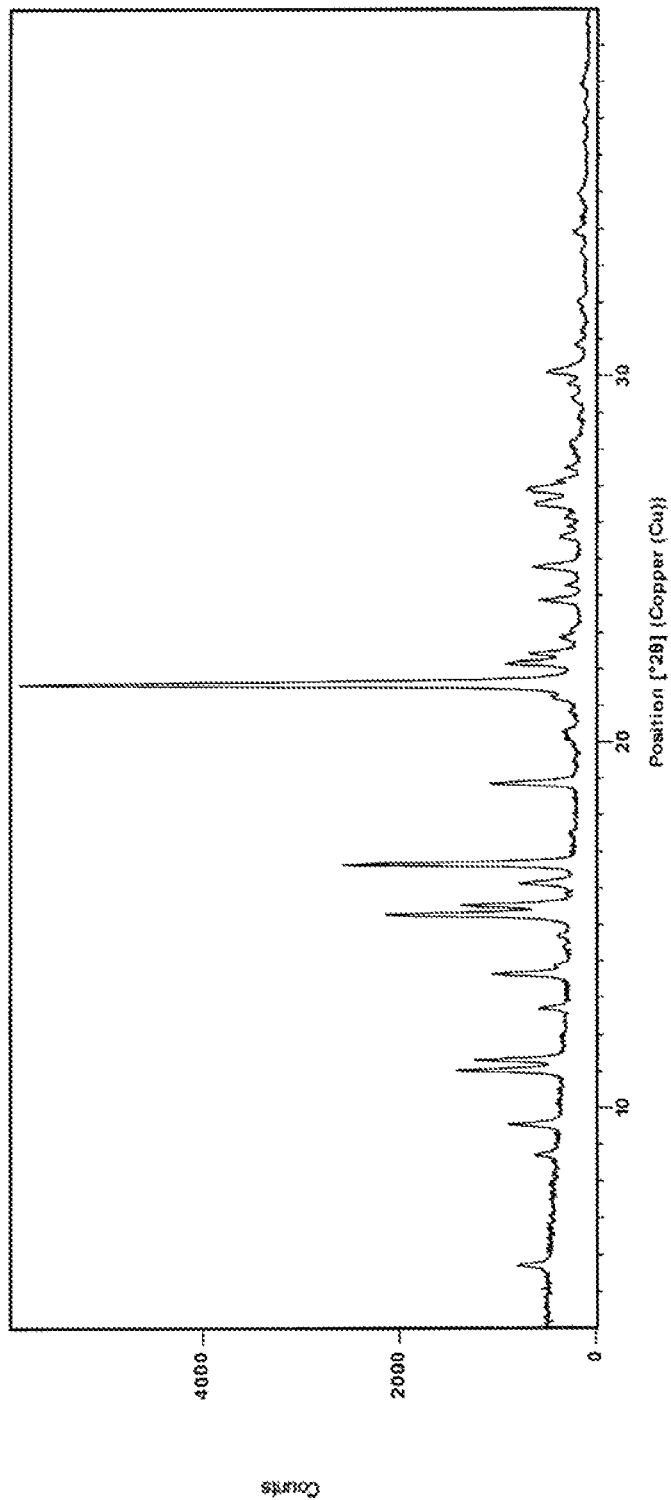

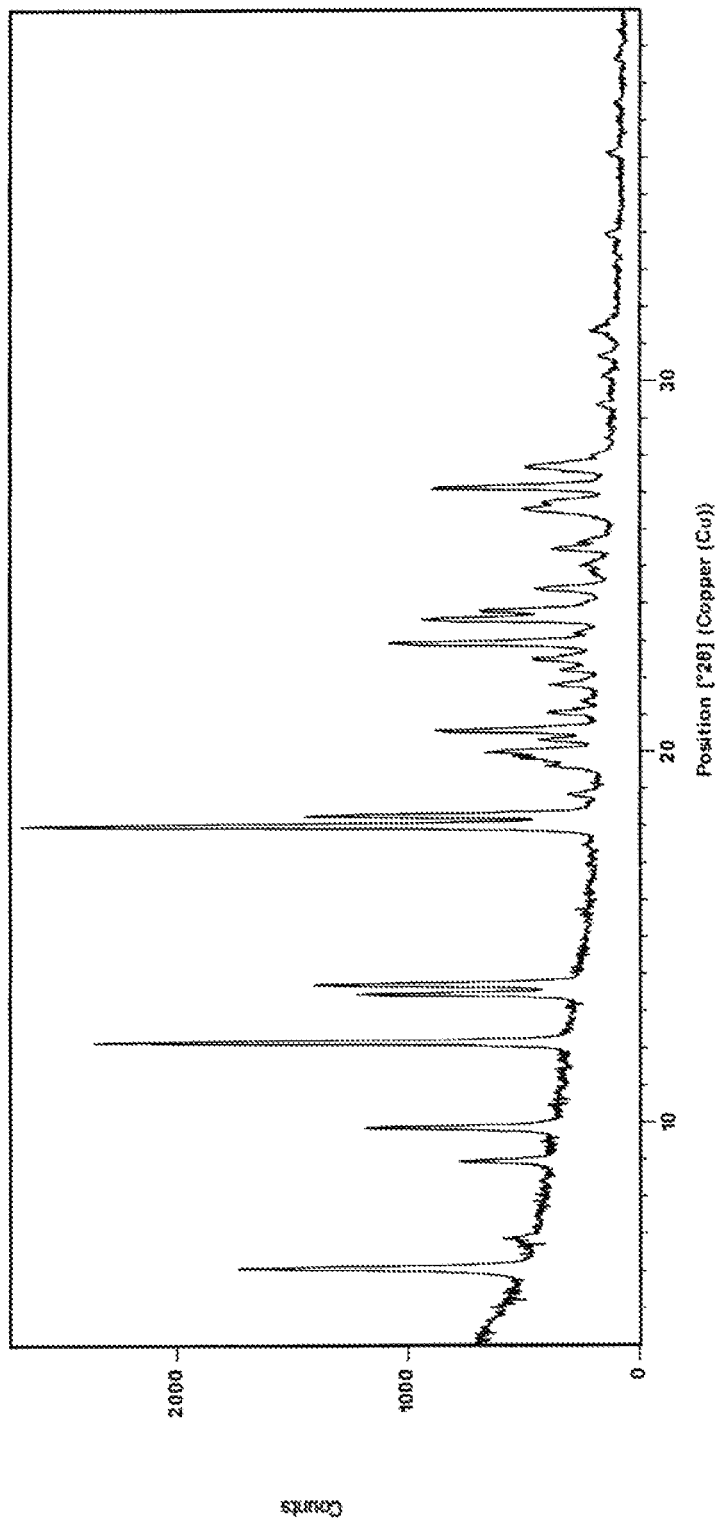

PROCESS FOR PREPARING SUBSTITUTED PYRAZOLO[1,5-a]PYRAZINES

CROSS-REFERENCE TO RELATED APPLICATIONS

This is continuation application of U.S. application Ser. No. 16/764,962 filed May 18, 2020, which is a U.S. national stage application filed under 35 U.S.C. § 371 of International Application No. PCT/JP2018/043094 filed Nov. 22, 2018, which claims priority to Japan Patent Application No. 2017-225364 filed Nov. 24, 2017, which is incorporated herein by reference in its entirety.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to a 6,7-dihydropyrazolo[1,5-a]pyrazinone derivative, or a pharmaceutically acceptable salt thereof, having negative allosteric modulation against Group II metabotropic glutamate (mGlu) receptors, and a preventive and/or therapeutic agent for a disease involving metabotropic glutamate receptor subtype 2 (mGluR2) and/or metabotropic glutamate receptor subtype 3 (mGluR3), comprising the same as an active ingredient.

Description of Related Art

Glutamate is a major excitatory neurotransmitter in the central nervous system, and acts on ion-channel receptors (i.e., N-methyl-D-aspartate (NMDA) glutamate receptor, α-amino-3-hydroxy-5-methyl-4-isoxazolepropionic acid (AMPA) receptor, and kainate receptor) and G-protein-coupled receptors (GPCRs) such as metabotropic glutamate receptors (mGlu receptors). mGlu receptors are classified as class C of GPCRs, and have an extracellular large orthosteric ligand binding site besides the seven transmembrane domain (TMD) common to GPCRs. mGlu receptors have high homology in the orthosteric ligand binding site, and it has been regarded as being difficult to develop subtype-selective orthosteric ligands. Allosteric modulators show the subtype selectivity by binding to the TMD (Non Patent Literatures 1 to 3).

mGlu receptors include 8 subtypes 1 to 8 (mGluR1 to 8), and are classified into Group I (mGluR1, mGluR5), Group II (mGluR2, mGluR3), and Group III (mGluR4, mGluR6, mGluR7, mGluR8) based on the homology, the signaling system to be conjugated, and pharmacological properties. Group II mGlu receptors (mGluR2, mGluR3) mainly express in presynapse, and negatively modulate glutamate release. It has been, therefore, reported that mGlu2/3 receptor negative allosteric modulators (NAMs) have the potential to an antidepressant (Non Patent Literature 4) and cognitive-function enhancer (Non Patent Literature 5).

Recently, compounds that act as an mGlu2/3 receptor NAM have been reported in Patent Literatures 1 to 7. These patent literatures, however, do not disclose or indicate a compound of Formula (1) as described hereinafter.

CITATION LIST

Patent Literature

[Patent Literature 1] WO 2014/195311
[Patent Literature 2] WO 2016/016380
[Patent Literature 3] WO 2016/016381
[Patent Literature 4] WO 2016/016382
[Patent Literature 5] WO 2016/016383
[Patent Literature 6] WO 2016/016395
[Patent Literature 7] WO 2016/087487

Non Patent Literature

[Non Patent Literature 1] Hemstapat et al, Pharmacology and Experimental Therapeutics, 2007, 322, 254-264
[Non Patent Literature 2] Lungstrom et al, British Journal of Pharmacology, 2011, 164, 521-537
[Non Patent Literature 3] Dore et al, Nature, 2014, 511, 557-562
[Non Patent Literature 4] Chaki et al, Neuropharmacology, 2013, 66, 40-52
[Non Patent Literature 5] Higgins et al, Neuropharmacology, 2004, 46, 907-917

BRIEF SUMMARY OF THE INVENTION

Problems to be Solved by the Invention

A problem to be solved by the present invention is to find out novel compounds having negative allosteric modulation against Group II mGlu receptors, and to provide a preventive and/or therapeutic agent useful for the treatment of a disease involving Group II mGlu receptors (i.e., metabotropic glutamate receptor subtype 2 (mGluR2) and/or metabotropic glutamate receptor subtype 3 (mGluR3)).

Means of Solving the Problems

The present inventor has found out that the problem is solved by a compound of Formula (1) as described below, or a pharmaceutically acceptable salt thereof, also referred to as "the present compound" hereinafter, and has achieved the present invention.

The present invention includes the following embodiments.

[Item 1]

A compound of Formula (1):

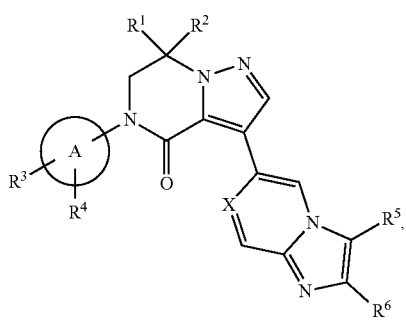

or a pharmaceutically acceptable salt thereof, wherein $R^1$ and $R^2$ are each independently hydrogen atom, halogen atom, cyano, $C_{1-4}$ alkyl, or $C_{3-6}$ saturated carbocyclyl group, wherein the alkyl and the saturated carbocyclyl group are each independent and may be optionally substituted with the same or different 1 to 5 substituents selected from the group consisting of halogen atom, hydroxy, and $C_{1-4}$ alkoxy, or alternatively, $R^1$ and $R^2$ may combine together with the carbon atom to which they attach to form a $C_{3-4}$ saturated carbocyclyl group, wherein the saturated carbocyclyl group may be optionally substituted with the same or different 1 to 5 substituents selected from the group consisting of halogen atom, hydroxy, and $C_{1-4}$ alkoxy;

Ring A is $C_{6-10}$ aromatic carbocyclyl group, 4- to 10-membered saturated heterocyclyl group, or 5- to 10-membered aromatic heterocyclyl group;

$R^3$ and $R^4$ are each independently hydrogen atom, halogen atom, cyano, hydroxy, $C_{1-6}$ alkyl, $C_{1-4}$ alkoxy, $C_{1-4}$ alkylthio, $C_{2-4}$ alkenyl, 4- to 6-membered saturated heterocyclyl group, or 5- or 6-membered aromatic heterocyclyl group (wherein the alkyl, the alkoxy, the alkylthio, the saturated heterocyclyl group, and the aromatic heterocyclyl group are each independent and may be optionally substituted with the same or different 1 to 5 halogen atoms), $C_{3-6}$ saturated carbocyclyl group, or $C_{3-6}$ cycloalkoxy, wherein the saturated carbocyclyl group and the cycloalkoxy are each independent and may be optionally substituted with the same or different 1 to 5 substituents selected from the group consisting of halogen atom and $C_{1-4}$ alkyl;

$R^5$ and $R^6$ are each independently hydrogen atom, halogen atom, cyano, hydroxy, $C_{1-6}$ alkyl, $C_{1-6}$ alkoxy, $C_{1-6}$ alkylthio, 4- to 6-membered saturated heterocyclyl group (wherein the alkyl, the alkoxy, the alkylthio, and the saturated heterocyclyl group are each independent and may be optionally substituted with the same or different 1 to 5 substituents selected from the group consisting of halogen atom, hydroxy, and $C_{1-4}$ alkoxy optionally substituted with the same or different 1 to 5 halogen atoms), $C_{3-6}$ cycloalkoxy, $C_{3-6}$ saturated carbocyclyl group (wherein the cycloalkoxy and the saturated carbocyclyl group are each independent and may be optionally substituted with the same or different 1 to 5 substituents selected from the group consisting of halogen atom, hydroxy, $C_{1-4}$ alkyl, and $C_{1-4}$ alkoxy optionally substituted with the same or different 1 to 5 halogen atoms), $-NR^aR^b$, $-NR^d-C(O)-R^c$, $-NR^d-C(O)-OR^c$, $-NR^d-C(O)-NR^aR^b$, $-NR^d-SO_2-R^c$, $-CH_2-C(O)-NR^aR^b$, $-C(O)-R^d$, $-C(O)-OR^d$, or $-C(O)-NR^aR^b$;

$R^a$ and $R^b$ are each independent and $R^a$s or $R^b$s when $NR^aR^b$ exists plurally are each independent, and they are hydrogen atom, $C_{1-4}$ alkyl (wherein the alkyl is each independent and may be optionally substituted with the same or different 1 to 5 substituents selected from the group consisting of halogen atom, hydroxy, and $C_{1-4}$ alkoxy), $C_{3-6}$ saturated carbocyclyl group, or 4- to 6-membered saturated heterocyclyl group, wherein the saturated carbocyclyl group and the saturated heterocyclyl group are each independent and may be optionally substituted with the same or different 1 to 5 substituents selected from the group consisting of halogen atom, hydroxy, $C_{1-4}$ alkyl, and $C_{1-4}$ alkoxy, or alternatively, $R^a$ and $R^b$ may combine together with the nitrogen atom to which they attach to form a 4- to 6-membered nitrogen-containing saturated heterocyclyl group, wherein the nitrogen-containing saturated heterocyclyl group may be optionally substituted with the same or different 1 to 5 substituents selected from the group consisting of halogen atom, hydroxy, $C_{1-4}$ alkyl, and $C_{1-4}$ alkoxy;

$R^c$, where $R^c$s are each independent when existing plurally, is $C_1$ alkyl, $C_{3-6}$ saturated carbocyclyl group, or 4- to 6-membered saturated heterocyclyl group, wherein the alkyl, the saturated carbocyclyl group, and the saturated heterocyclyl group are each independent and may be optionally substituted with the same or different 1 to 5 substituents selected from the group consisting of halogen atom, hydroxy, and $C_{1-4}$ alkoxy;

$R^d$, where $R^d$s are each independent when existing plurally, is hydrogen atom, $C_{1-4}$ alkyl, $C_{3-6}$ saturated carbocyclyl group, or 4- to 6-membered saturated heterocyclyl group, wherein the alkyl, the saturated carbocyclyl group, and the saturated heterocyclyl group are each independent and may be optionally substituted with the same or different 1 to 5 substituents selected from the group consisting of halogen atom, hydroxy, and $C_{1-4}$ alkoxy;

X is nitrogen atom or $-CR^e-$; and $R^e$ is hydrogen atom, halogen atom, cyano, $C_{1-6}$ alkyl, or $C_{1-6}$ alkoxy, wherein the alkyl and the alkoxy may be optionally substituted with the same or different 1 to 5 halogen atoms.

[Item 2]

The compound according to Item 1, or a pharmaceutically acceptable salt thereof, wherein $R^1$ and $R^2$ are each independently hydrogen atom or $C_{1-4}$ alkyl, wherein the alkyl may be optionally substituted with the same or different 1 to 5 substituents selected from the group consisting of halogen atom, hydroxy, and $C_{1-4}$ alkoxy, or alternatively, $R^1$ and $R^2$ combine together with the carbon atom to which they attach to form a cyclopropane ring or cyclobutane ring.

[Item 3]

The compound according to Item 1 or 2, or a pharmaceutically acceptable salt thereof, wherein Ring A is benzene, naphthalene, pyridine, pyrimidine, pyrazine, thiophene, thiazole, isothiazole, oxazole, isoxazole, quinoline, isoquinoline, benzothiophene, benzofuran, indolizine, imidazopyridine, 1,3-benzodioxole, chromane, 2,3-dihydrobenzofuran, 1,3-dihydroisobenzofuran, 2,3-dihydro-1H-indene, or 2,3-dihydro-1H-inden-1-one.

[Item 4]

The compound according to any one of Items 1 to 3, or a pharmaceutically acceptable salt thereof, wherein $R^3$ and $R^4$ are each independently
  (1) hydrogen atom,
  (2) halogen atom,
  (3) cyano,
  (4) hydroxy,
  (5) $C_{1-4}$ alkyl optionally substituted with the same or different 1 to 5 halogen atoms,
  (6) $C_{1-4}$ alkoxy optionally substituted with the same or different 1 to 5 halogen atoms,
  (7) $C_{3-6}$ cycloalkoxy, wherein the cycloalkoxy may be optionally substituted with the same or different 1 to 5 substituents selected from the group consisting of $C_{1-4}$ alkyl and halogen atom, or
  (8) $C_{1-4}$ alkylthio optionally substituted with the same or different 1 to 5 halogen atoms.

[Item 5]

The compound according to any one of Items 1 to 4, or a pharmaceutically acceptable salt thereof, wherein $R^5$ and $R^6$ are each independently
  (1) hydrogen atom,
  (2) halogen atom,
  (3) cyano,
  (4) hydroxy,
  (5) $C_{1-4}$ alkyl, wherein the alkyl may be optionally substituted with the same or different 1 to 5 substituents selected from the group consisting of halogen atom, hydroxy, and $C_{1-4}$ alkoxy optionally substituted with the same or different 1 to 5 halogen atoms,
  (6) $C_1$ alkoxy, wherein the alkoxy may be optionally substituted with the same or different 1 to 5 substituents selected from the group consisting of halogen atom, hydroxy, and $C_{1-4}$ alkoxy optionally substituted with the same or different 1 to 5 halogen atoms,
  (7) 4- to 6-membered saturated heterocyclyl group, wherein the saturated heterocyclyl group may be optionally substituted with the same or different 1 to 5 substituents selected from the group consisting of halogen atom, hydroxy, and $C_{1-4}$ alkoxy optionally substituted with the same or different 1 to 5 halogen atoms, or
  (8) —$NR^aR^b$, —$NR^d$—C(O)—$R^c$, —$NR^d$—C(O)—$OR^c$, —$NR^d$—C(O)—$NR^aR^b$, —$NR^d$—$SO_2$—$R^c$, —$CH_2$—C(O)—$NR^aR^b$, —C(O)—$R^d$, —C(O)—$OR^d$, or —C(O)—$NR^aR^b$.

[Item 6]

The compound according to any one of Items 1 to 5, or a pharmaceutically acceptable salt thereof, wherein $R^a$ and $R^b$ are each independent and $R^a$s or $R^b$s when $NR^aR^b$ exists plurally are each independent, and they are hydrogen atom or $C_{1-4}$ alkyl, wherein the alkyl is each independent and may be optionally substituted with the same or different 1 to 5 substituents selected from the group consisting of halogen atom, hydroxy, and $C_{1-4}$ alkoxy, or alternatively, $R^a$ and $R^b$ combine together with the nitrogen atom to which they attach to form a 4- to 6-membered nitrogen-containing saturated heterocyclyl group, wherein the nitrogen-containing saturated heterocyclyl group may be optionally substituted with the same or different 1 to 5 substituents selected from the group consisting of halogen atom, hydroxy, $C_{1-4}$ alkyl, and $C_{1-4}$ alkoxy.

[Item 7]

The compound according to any one of Items 1 to 6, or a pharmaceutically acceptable salt thereof, wherein $R^c$, where $R^c$s are each independent when existing plurally, is $C_{1-4}$ alkyl or $C_{3-6}$ saturated carbocyclyl group, wherein the alkyl and the saturated carbocyclyl group are each independent and may be optionally substituted with the same or different 1 to 5 substituents selected from the group consisting of halogen atom, hydroxy, and $C_{1-4}$ alkoxy.

[Item 8]

The compound according to any one of Items 1 to 7, or a pharmaceutically acceptable salt thereof, wherein $R^d$, where $R^d$s are each independent when existing plurally, is
  (1) hydrogen atom,
  (2) $C_{1-4}$ alkyl, wherein the alkyl may be optionally substituted with the same or different 1 to 5 substituents selected from the group consisting of halogen atom, hydroxy, and $C_{1-4}$ alkoxy, or
  (3) $C_{3-6}$ saturated carbocyclyl group, wherein the saturated carbocyclyl group may be optionally substituted with the same or different 1 to 5 substituents selected from the group consisting of halogen atom, hydroxy, and $C_{1-4}$ alkoxy.

[Item 9]

The compound according to any one of Items 1 to 8, or a pharmaceutically acceptable salt thereof, wherein $R^e$ is
  (1) hydrogen atom,
  (2) halogen atom, or
  (3) $C_{1-4}$ alkyl optionally substituted with the same or different 1 to 5 halogen atoms.

[Item 10]

The compound according to any one of Items 1, 3 to 9, or a pharmaceutically acceptable salt thereof, wherein $R^1$ and $R^2$ are each independently hydrogen atom, methyl, ethyl, isopropyl, cyclopropyl, methoxymethyl, hydroxymethyl, difluoromethyl, or trifluoromethyl, or alternatively, $R^1$ and $R^2$ combine together with the carbon atom to which they attach to form a cyclopropane ring or a cyclobutane ring.

[Item 11]

The compound according to any one of Items 1 to 10, or a pharmaceutically acceptable salt thereof, wherein Ring A is benzene, thiophene, pyridine, quinoline, or 1,3-benzodioxole.

[Item 12]

The compound according to any one of Items 1 to 11, or a pharmaceutically acceptable salt thereof, wherein $R^3$ and $R^4$ are each independently
  (1) hydrogen atom,
  (2) halogen atom,
  (3) cyano,
  (4) $C_{1-4}$ alkyl optionally substituted with the same or different 1 to 5 halogen atoms, or
  (5) $C_{1-4}$ alkoxy optionally substituted with the same or different 1 to 5 halogen atoms.

[Item 13]

The compound according to any one of Items 1 to 12, or a pharmaceutically acceptable salt thereof, wherein $R^c$, where $R^c$s are each independent when existing plurally, is $C_{1-4}$ alkyl optionally substituted with the same or different 1 to 5 halogen atoms.

[Item 14]

The compound according to any one of Items 1 to 13, or a pharmaceutically acceptable salt thereof, wherein $R^d$, where $R^d$s are each independent when existing plurally, is hydrogen atom or $C_{1-4}$ alkyl optionally substituted with the same or different 1 to 5 halogen atoms.

[Item 15]

The compound according to any one of Items 1 to 14, or a pharmaceutically acceptable salt thereof, wherein $R^5$ and $R^6$ are each independently
(1) hydrogen atom,
(2) halogen atom,
(3) cyano,
(4) hydroxy,
(5) $C_{1-4}$ alkyl, wherein the alkyl may be optionally substituted with the same or different 1 to 5 substituents selected from the group consisting of halogen atom, hydroxy, and $C_{1-4}$ alkoxy optionally substituted with the same or different 1 to 5 halogen atoms,
(6) $C_{1-4}$ alkoxy, wherein the alkoxy may be optionally substituted with the same or different 1 to 5 substituents selected from the group consisting of halogen atom, hydroxy, and $C_{1-4}$ alkoxy optionally substituted with the same or different 1 to 5 halogen atoms,
(7) 4- to 6-membered saturated heterocyclyl group, wherein the saturated heterocyclyl group may be optionally substituted with the same or different 1 to 5 substituents selected from the group consisting of halogen atom, hydroxy, and $C_{1-4}$ alkoxy optionally substituted with the same or different 1 to 5 halogen atoms, or
(8) —$NR^aR^b$.

[Item 16]

The compound according to any one of Items 1 to 15, or a pharmaceutically acceptable salt thereof, wherein $R^a$ and $R^b$ are each independent and $R^a$s or $R^b$s when $NR^aR^b$ exists plurally are each independent, and they are hydrogen atom or $C_{1-4}$ alkyl, wherein the alkyl may be optionally substituted with the same or different 1 to 3 substituents selected from the group consisting of halogen atom, hydroxy, and $C_{1-4}$ alkoxy.

[Item 17]

The compound according to any one of Items 1 to 16, or a pharmaceutically acceptable salt thereof, wherein $R^e$ is
(1) hydrogen atom,
(2) fluorine atom, or
(3) $C_{1-4}$ alkyl optionally substituted with the same or different 1 to 5 halogen atoms.

[Item 18]

The compound according to Item 1, or a pharmaceutically acceptable salt thereof, wherein $R^1$ is methyl;
$R^2$ is hydrogen atom;
a 6,7-dihydropyrazolo[1,5-a]pyrazin-4(5H)-one moiety has S-configuration at the 7-position;
Ring A is benzene;
$R^3$ and $R^4$ are each independently hydrogen atom, fluorine, chlorine, difluoromethyl, trifluoromethyl, or difluoromethoxy;
$R^5$ and $R^6$ are each independently hydrogen atom or —$NH_2$; and
X is nitrogen atom or —CH—.

[Item 19]

The compound according to Item 1, or a pharmaceutically acceptable salt thereof, selected from the following compounds:
Example 1: (7S)-3-(imidazo[1,2-a]pyridin-6-yl)-7-methyl-5-[4-(trifluoromethyl)phenyl]-6,7-dihydropyrazolo[1,5-a]pyrazin-4(5H)-one;
Example 2: (7S)-3-(imidazo[1,2-a]pyrazin-6-yl)-7-methyl-5-[4-(trifluoromethyl)phenyl]-6,7-dihydropyrazolo[1,5-a]pyrazin-4 (5H)-one;
Example 3: (7S)-3-(imidazo[1,2-a]pyridin-6-yl)-7-methyl-5-[3-chloro-4-fluorophenyl]-6,7-dihydropyrazolo[1,5-a]pyrazin-4(5H)-one;
Example 4: (7S)-5-[4-(difluoromethyl)phenyl]-3-(imidazo[1,2-a]pyridin-6-yl)-7-methyl-6,7-dihydropyrazolo[1,5-a]pyrazin-4(5H)-one;
Example 5: (7S)-5-(4-chloro-3-fluorophenyl)-3-(imidazo[1,2-a]pyridin-6-yl)-7-methyl-6,7-dihydropyrazolo[1,5-a]pyrazin-4 (5H)-one;
Example 6: (7S)-5-(4-chlorophenyl)-3-(imidazo[1,2-a]pyridin-6-yl)-7-methyl-6,7-dihydropyrazolo[1,5-a]pyrazin-4 (5H)-one;
Example 9: (7S)-5-[4-(difluoromethoxy)phenyl]-3-(imidazo[1,2-a]pyridin-6-yl)-7-methyl-6,7-dihydropyrazolo[1,5-a]pyrazin-4(5H)-one; and
Example 11: (7S)-3-(3-aminoimidazo[1,2-a]pyridin-6-yl)-7-methyl-5-[4-(trifluoromethyl)phenyl]-6,7-dihydropyrazolo[1,5-a]pyrazin-4(5H)-one.

[Item 20]

The compound according to Item 1, or a pharmaceutically acceptable salt thereof, selected from the following compounds:
Example 13: (7S)-3-(3-fluoroimidazo[1,2-a]pyridin-6-yl)-7-methyl-5-[4-(trifluoromethyl)phenyl]-6,7-dihydropyrazolo[1,5-a]pyrazin-4(5H)-one;
Example 14: (7S)-7-methyl-3-(3-methylimidazo[1,2-a]pyridin-6-yl)-5-[4-(trifluoromethyl)phenyl]-6,7-dihydropyrazolo[1,5-a]pyrazin-4(5H)-one;
Example 15: (7S)-3-(3-ethylimidazo[1,2-a]pyridin-6-yl)-7-methyl-5-[4-(trifluoromethyl)phenyl]-6,7-dihydropyrazolo[1,5-a]pyrazin-4(5H)-one; and
Example 16: (7S)-7-methyl-3-(3-propylimidazo[1,2-a]pyridin-6-yl)-5-[4-(trifluoromethyl)phenyl]-6,7-dihydropyrazolo[1,5-a]pyrazin-4(5H)-one.

[Item 21]

The compound according to Item 1, or a hydrochloride or phosphate salt thereof, selected from the following compounds:
Example 1: (7S)-3-(imidazo[1,2-a]pyridin-6-yl)-7-methyl-5-[4-(trifluoromethyl)phenyl]-6,7-dihydropyrazolo[1,5-a]pyrazin-4(5H)-one;
Example 3: (7S)-3-(imidazo[1,2-a]pyridin-6-yl)-7-methyl-5-[3-chloro-4-fluorophenyl]-6,7-dihydropyrazolo[1,5-a]pyrazin-4 (5H)-one;
Example 13: (7S)-3-(3-fluoroimidazo[1,2-a]pyridin-6-yl)-7-methyl-5-[4-(trifluoromethyl)phenyl]-6,7-dihydropyrazolo[1,5-a]pyrazin-4(5H)-one; and
Example 14: (7S)-7-methyl-3-(3-methylimidazo[1,2-a]pyridin-6-yl)-5-[4-(trifluoromethyl)phenyl]-6,7-dihydropyrazolo[1,5-a]pyrazin-4(5H)-one.

[Item 22]

A pharmaceutical composition comprising a compound according to any one of Items 1 to 21, or a pharmaceutically acceptable salt thereof.

[Item 23]

A therapeutic agent and/or preventive agent for a disease involving Group II mGlu receptor, comprising a compound according to any one of Items 1 to 21, or a pharmaceutically acceptable salt thereof, as an active ingredient.

[Item 24]

The therapeutic agent and/or preventive agent according to Item 23, wherein the Group II mGlu receptor is metabotropic glutamate receptor subtype 2 (mGluR2).

[Item 25]
The therapeutic agent and/or preventive agent according to Item 23 or 24, wherein the disease involving Group II mGlu receptor is psychiatric disease or neurodegenerative disease.

[Item 26]
The therapeutic agent and/or preventive agent according to Item 25, wherein the psychiatric disease or neurodegenerative disease is major depressive disorder, depressive disorder, bipolar and related disorders, anxiety disorder, posttraumatic stress disorder, obsessive-compulsive disorder, acute stress disorder, schizophrenia, autism spectrum disorder, Alzheimer's disease, cognitive dysfunction, dementia, drug dependence, obesity, seizure, tremor, pain, or sleep disorder.

[Item 27]
Use of a compound according to any one of Items 1 to 21, or a pharmaceutically acceptable salt thereof, in the manufacture of a therapeutic agent and/or preventive agent for a disease involving Group II mGlu receptor.

[Item 28]
A compound according to any one of Items 1 to 21, or a pharmaceutically acceptable salt thereof, for use in the treatment and/or prevention of a disease involving Group II mGlu receptor.

[Item 29]
A method for treating and/or preventing a disease involving Group II mGlu receptor, comprising administering a therapeutically effective amount of a compound according to any one of Items 1 to 21, or a pharmaceutically acceptable salt thereof, to a patient in need thereof.

[Item 30]
A medicament which comprises a medicament comprising a compound according to any one of Items 1 to 21, or a pharmaceutically acceptable salt thereof, and one or more medicaments selected from therapeutic agents for major depressive disorder, depressive disorder, bipolar and related disorders, anxiety disorder, posttraumatic stress disorder, obsessive-compulsive disorder, acute stress disorder, schizophrenia, autism spectrum disorder, Alzheimer's disease, cognitive dysfunction, dementia, drug dependence, obesity, seizure, tremor, pain, or sleep disorder.

[Item 31]
A medicament for treating psychiatric disease or neurodegenerative disease, comprising a compound according to any one of Items 1 to 21, or a pharmaceutically acceptable salt thereof, for use in combination with one or more antipsychotic drugs.

[Item 32]
A method of preparing a compound of Formula (1a):

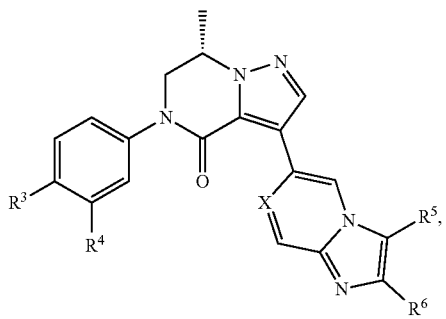

(1a)

or a pharmaceutically acceptable salt thereof, wherein $R^3$ and $R^4$ are each independently hydrogen atom, halogen atom, $C_{1-6}$ alkyl, or $C_{1-4}$ alkoxy, wherein the alkyl and the alkoxy are each independent and may be optionally substituted with the same or different 1 to 5 halogen atoms;

$R^5$ and $R^6$ are each independently hydrogen atom, halogen atom, $C_{1-6}$ alkyl, or —$NH_2$; and X is nitrogen atom or —CH—, which comprises the following steps:

(step A1) reacting a compound of Formula (4a):

(4a)

wherein PG is a protecting group such as tert-butoxycarbonyl group and benzyloxycarbonyl group, and a compound of Formula (3):

(3)

wherein $R^7$ is methyl or ethyl, under Mitsunobu condition to give a compound of Formula (6a):

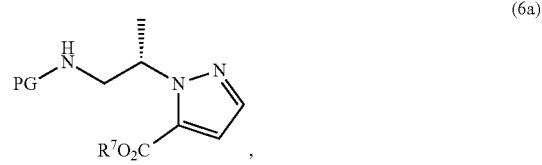

(6a)

wherein PG and $R^7$ are as defined in this Item;

(step A2) cyclizing the compound of Formula (6a) in the presence of an acid or base to give a compound of Formula (7a):

(7a)

(step A3) coupling the compound of Formula (7a) and a compound of Formula (8a):

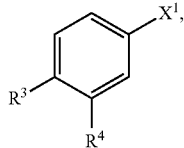
(8a)

wherein $R^3$ and $R^4$ are as defined in this Item, and $X^1$ is iodine, bromine, or chlorine,
in the presence of a transition metal catalyst to give a compound of Formula (9a):

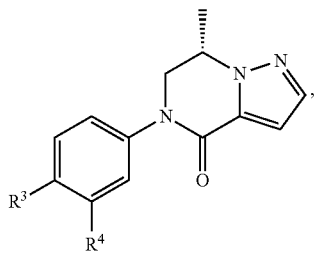
(9a)

wherein $R^3$ and $R^4$ are as defined in this Item;
(step A4) reacting the compound of Formula (9a) in the presence of a halogenating agent to give a compound of Formula (15a)

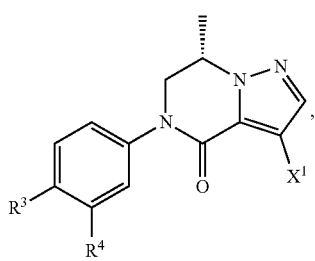
(15a)

wherein $R^3$, $R^4$, and $X^1$ are as defined in this Item; and
(step A5) coupling the compound of Formula (15a) and a compound of Formula (16):

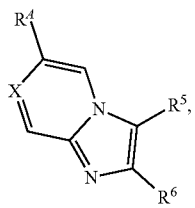
(16)

or a salt thereof,
wherein $R^5$, $R^6$, and X are as defined in this claim, and $R^4$ is boronic acid or boronic acid ester, in the presence of a transition metal catalyst to give a compound of Formula (1a) or a pharmaceutically acceptable salt thereof.

[Item 33]
A method of preparing a compound of Formula (1a):

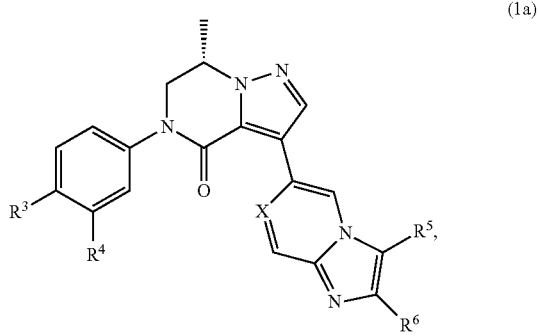
(1a)

or a pharmaceutically acceptable salt thereof,
wherein $R^3$ and $R^4$ are each independently hydrogen atom, halogen atom, $C_{1-6}$ alkyl, or $C_{1-4}$ alkoxy, wherein the alkyl and the alkoxy are each independent and may be optionally substituted with the same or different 1 to 5 halogen atoms;
$R^5$ and $R^6$ are each independently hydrogen atom, halogen atom, $C_{1-6}$ alkyl, or —$NH_2$; and
X is nitrogen atom or —CH—,
which comprises the following steps:
(step B1) coupling a compound of Formula (8a):

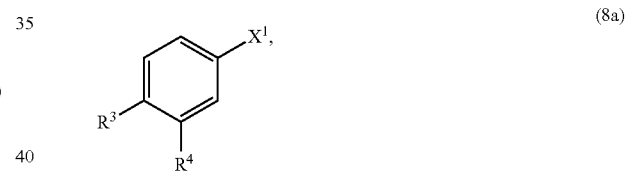
(8a)

wherein $R^3$ and $R^4$ are as defined in this Item, and $X^1$ is iodine, bromine, or chlorine,
with a compound of Formula (12a):

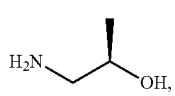
(12a)

or a salt thereof,
in the presence of a transition metal catalyst to give a compound of Formula (13a):

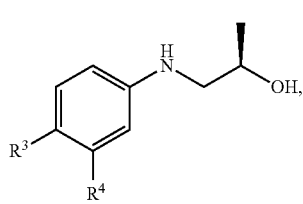
(13a)

or a salt thereof,
wherein $R^3$ and $R^4$ are as defined in this Item;

(step B2) reacting the compound of Formula (13a), or a salt thereof, and a compound of Formula (22):

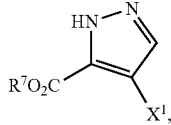
(22)

or a salt thereof,
wherein $X^1$ is as defined in this Item, and $R^7$ is methyl or ethyl,
under Mitsunobu condition to give a compound of Formula (23a):

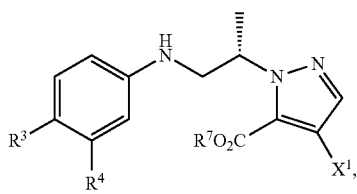
(23a)

or a salt thereof,
wherein $R^3$, $R^4$, $R^7$, and $X^1$ are as defined in this Item;
(step B3) hydrolyzing the compound of Formula (23a), or a salt thereof, in the presence of an acid or base to give a compound of Formula (24a):

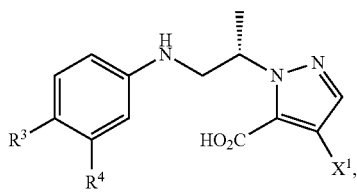
(24a)

or a salt thereof,
wherein $R^3$, $R^4$, and $X^1$ are as defined in this Item; (step B4) cyclizing the compound of Formula (24a), or a salt thereof, in the presence of an acid or base to give a compound of Formula (15a):

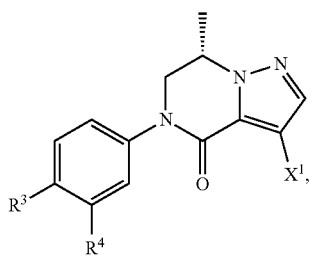
(15a)

wherein $R^3$, $R^4$, and $X^1$ are as defined in this Item; and (step B5) coupling the compound of Formula (15a) and a compound of Formula (16):

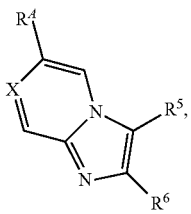
(16)

or a salt thereof,
wherein $R^5$, $R^6$, and X are as defined in this Item, and $R^A$ is boronic acid or boronic acid ester,
in the presence of a transition metal catalyst to give a compound of Formula (1a), or a pharmaceutically acceptable salt thereof;
wherein the step B3 and step B4 may be replaced with one single step of the following step B6:
(step B6) cyclizing the compound of Formula (23a), or a salt thereof, in the presence of an acid or base to give a compound of Formula (15a).
[Item 34]
A crystal (Crystalline Form I) of (7S)-3-(imidazo[1,2-a]pyridin-6-yl)-7-methyl-5-[4-(trifluoromethyl)phenyl]-6,7-dihydropyrazolo[1,5-a]pyrazin-4(5H)-one, having a powder X-ray diffraction pattern comprising diffraction peaks at diffraction angles 2θ (°): 4.5±0.2, 8.5±0.2, 8.9±0.2, 10.1±0.2, 13.4±0.2, and 16.9±0.2, measured by powder X-ray diffraction.
[Item 35]
A crystal (Crystalline Form II) of a hydrochloride salt of (7S)-3-(imidazo[1,2-a]pyridin-6-yl)-7-methyl-5-[4-(trifluoromethyl)phenyl]-6,7-dihydropyrazolo[1,5-a]pyrazin-4(5H)-one, having a powder X-ray diffraction pattern comprising diffraction peaks at diffraction angles 2θ (°): 5.7±0.2, 8.7±0.2, 9.5±0.2, 11.0±0.2, 11.3±0.2, and 15.3±0.2, measured by powder X-ray diffraction.
[Item 36]
A crystal (Crystalline Form III) of a 2.5 phosphate salt of (7S)-3-(imidazo[1,2-a]pyridin-6-yl)-7-methyl-5-[4-(trifluoromethyl)phenyl]-6,7-dihydropyrazolo[1,5-a]pyrazin-4(5H)-one, having a powder X-ray diffraction pattern comprising diffraction peaks at diffraction angles 2θ (°): 6.1±0.2, 8.9±0.2, 9.8±0.2, 12.1±0.2, 13.4±0.2, and 13.7±0.2, measured by powder X-ray diffraction.

Effect of the Invention

The present compound shows negative allosteric modulation against Group II metabotropic glutamate (mGlu) receptors. Thus, the present compound is useful for a therapeutic agent and/or preventive agent for a disease involving Group II mGlu receptors (i.e., metabotropic glutamate receptor subtype 2 (mGluR2) and/or metabotropic glutamate receptor subtype 3 (mGluR3)).

BRIEF DESCRIPTION OF THE SEVERAL VIEWS OF THE DRAWINGS

FIG. 2 shows a powder X-ray diffraction pattern of Crystalline Form II.

FIG. 3 shows a powder X-ray diffraction pattern of Crystalline Form III.

DETAILED DESCRIPTION OF THE INVENTION

Figure 1:
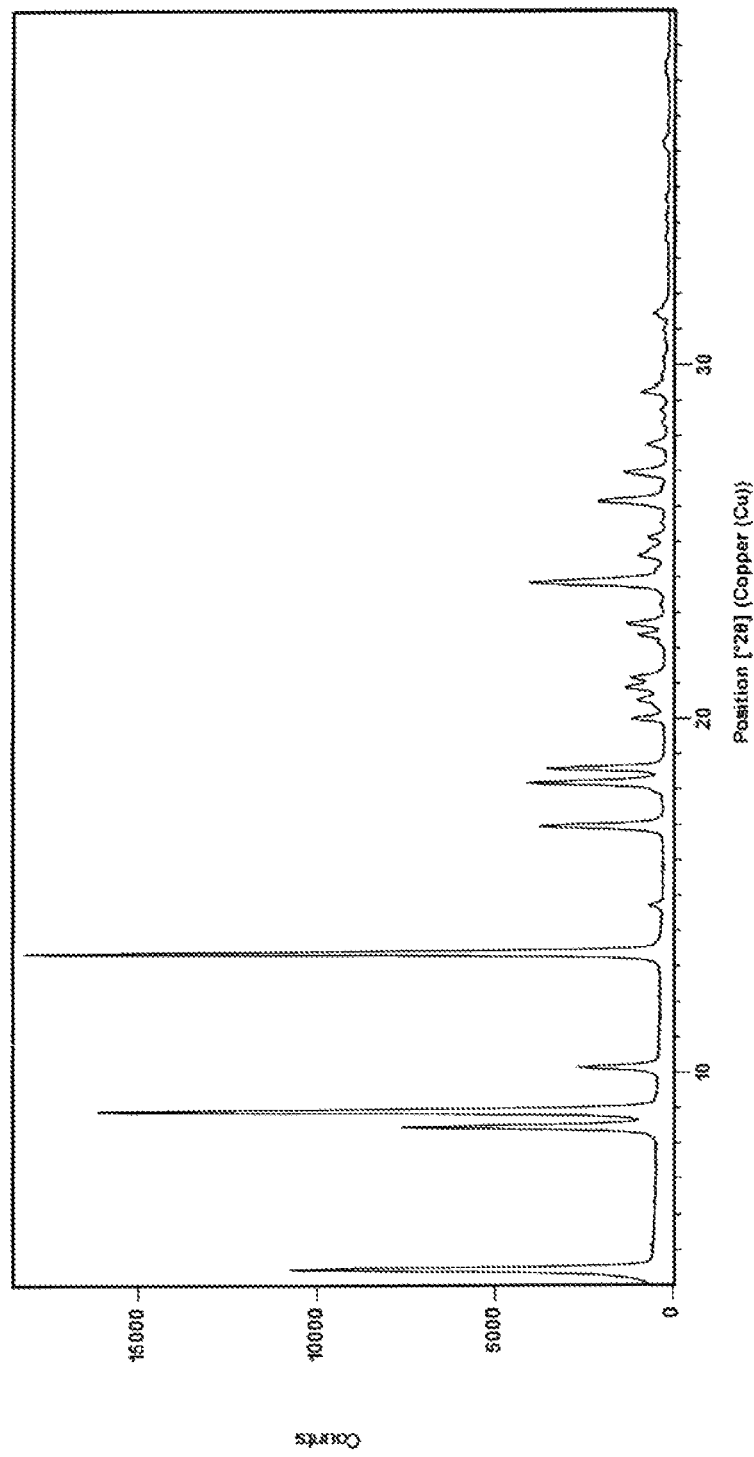
FIG. 1 shows a powder X-ray diffraction pattern of Crystalline Form I. The horizontal axis indicates diffraction angles 2θ (°), whereas the vertical axis indicates the number of counts; hereinafter, the same can be applied to FIGS. 2 and 3.

Hereinafter, the terms used herein are explained.

The term "group" means a monovalent group. The term "group" may be omitted herein.

The number of substituents in a group defined with the term "optionally substituted" or "substituted" is not limited as long as they are applicable. Each definition of each group is also applicable to the case where the group is a part or a substituent of other groups, unless otherwise indicated.

The term "$C_{1-4}$ alkyl" means an aliphatic hydrocarbon group having 1 to 4 carbon atoms, and the term "$C_G$ alkyl" means an aliphatic hydrocarbon group having 4 carbon atoms. The same can be applied to the other numbers. Examples of "$C_{1-4}$ alkyl" include, for example, methyl, ethyl, n-propyl, 1-methylethyl, n-butyl, 1,1-dimethylethyl, 1-methylpropyl, and 2-methylpropyl.

The term "$C_{1-6}$ alkyl" means an aliphatic hydrocarbon group having 1 to 6 carbon atoms. "$C_{1-6}$ alkyl" includes, preferably, "$C_{1-4}$ alkyl". Examples of "$C_{1-6}$ alkyl" include, for example, 4-methylpentyl, 3-methylpentyl, 2-methylpentyl, 1-methylpentyl, and n-hexyl besides the examples of "$C_{1-4}$ alkyl" as described above.

The term "halogen" includes, for example, fluorine, chlorine, bromine, and iodine. A preferable one is fluorine or chlorine.

The term "$C_{1-4}$ alkoxy" means an oxy group substituted with "$C_{1-4}$ alkyl" as described above. Examples of "$C_{1-4}$ alkoxy" include, for example, methoxy, ethoxy, n-propoxy, 1-methylethoxy, n-butoxy, 1,1-dimethylethoxy, 1-methylpropoxy, and 2-methylpropoxy. A preferable one is methoxy or ethoxy.

The term "$C_{1-6}$ alkoxy" means an oxy group substituted with "$C_{1-6}$ alkyl" as described above. "$C_{1-6}$ alkoxy" includes, preferably, "$C_{1-4}$ alkoxy". Examples of "$C_{1-6}$ alkoxy" include, for example, n-pentyloxy, 3-methylbutoxy, 2-methylbutoxy, 2,2-dimethylpropoxy, 1-ethylpropoxy, 1,1-dimethylpropoxy, n-hexyloxy, 4-methylpentyloxy, 3-methylpentyloxy, 2-methylpentyloxy, 1-methylpentyloxy, 3,3-dimethylbutoxy, 2,2-dimethylbutoxy, 1,1-dimethylbutoxy, and 1,2-dimethylbutoxy besides the examples of "$C_{1-4}$ alkoxy" as described above.

The term "$C_{3-6}$ cycloalkoxy" means an oxy group substituted with cyclic alkyl having 3 to 6 carbon atoms. Examples of "$C_{3-6}$ cycloalkoxy" include, for example, cyclopropoxy, cyclobutoxy, cyclopentyloxy, and cyclohexyloxy. A preferable one is cyclopropoxy or cyclobutoxy.

The term "$C_{1-4}$ alkylthio" means a thiol group substituted with "$C_{1-4}$ alkyl" as described above. Examples of "$C_{1-4}$ alkylthio" include, for example, methylthio, ethylthio, n-propylthio, isopropylthio, n-butylthio, isobutylthio, s-butylthio, and t-butylthio.

The term "$C_{1-6}$ alkylthio" means a thiol group substituted with "$C_{1-6}$ alkyl" as described above. "$C_{1-6}$ alkylthio" includes, preferably, "$C_{1-4}$ alkylthio". Examples of "$C_{1-6}$ alkylthio" include, for example, 1-ethylpropylthio, n-pentylthio, neopentylthio, n-hexylthio, and isohexylthio besides the examples of "$C_{1-4}$ alkylthio" as described above.

The term "$C_{2-4}$ alkenyl" means an aliphatic hydrocarbon group having 2 to 4 carbon atoms in the chain and comprising at least one carbon-carbon double bond. Examples of "$C_{2-4}$ alkenyl" include, for example, vinyl, allyl, 1-propenyl, and 1-butenyl.

The term "$C_{3-6}$ saturated carbocycle" means a monocyclic saturated or partially unsaturated hydrocarbon ring having 3 to 6 carbon atoms. "$C_{3-6}$ saturated carbocycle" includes, preferably, "$C_{3-4}$ saturated carbocycle". Examples of "$C_{3-6}$ saturated carbocycle" include, for example, cyclopropane, cyclobutane, cyclopentane, cyclohexane, cyclopropene, cyclobutene, cyclopentene, cyclohexene, and cyclohexadiene. A preferable one is cyclopropane or cyclobutane.

The term "$C_{3-4}$ saturated carbocyclyl group" means a monovalent group of "$C_{3-4}$ saturated carbocycle" among "$C_{3-6}$ saturated carbocycle" as described above.

The term "4- to 10-membered saturated heterocycle" means a monocyclic or bicyclic saturated heterocycle consisting of 4 to 10 atoms, comprising the same or different one or two heteroatoms selected from the group consisting of oxygen atom, nitrogen atom, and sulfur atom, and includes that which comprises a partially unsaturated bond, partially bridged structure, or partial spiro structure. The bicyclic saturated heterocycle includes a fused ring wherein a monocyclic saturated heterocycle is fused with benzene or a monocyclic 5- to 6-membered aromatic heterocycle. The saturated heterocycle may comprise one or two carbonyl, thiocarbonyl, sulfinyl, or sulfonyl for formation, and includes cyclic groups such as lactam, thiolactam, lactone, thiolactone, cyclic imide, cyclic carbamate, and cyclic thiocarbamate. The oxygen atom of carbonyl, sulfinyl, and sulfonyl or the sulfur atom of thiocarbonyl is not counted as the number of the 4- to 10-members (i.e., the size of the ring) or heteroatoms that form the ring. The "4- to 10-membered saturated heterocycle" includes, preferably a monocyclic or bicyclic "4- to 8-membered saturated heterocycle", more preferably a monocyclic "4- to 6-membered saturated heterocycle", further preferably a monocyclic "5- or 6-membered saturated heterocycle". Examples of the "4-to 10-membered saturated heterocycle" include, for example, azetidine, pyrrolidine, piperidine, piperazine, morpholine, homopiperidine, oxetane, tetrahydrofuran, tetrahydropyran, 1,3-benzodioxole, and 1,3-dihydroisobenzofuran, and preferably, pyrrolidine, piperidine, piperazine, morpholine, 1,3-benzodioxole, and 1,3-dihydroisobenzofuran.

The term "4- to 6-membered saturated heterocyclyl group" means a monovalent group of "4- to 6-membered saturated heterocycle" among "4- to 10-membered saturated heterocycle" as described above. A preferable one is azetidinyl, pyrrolidinyl, piperidinyl, piperazinyl, morpholinyl, oxetanyl, tetrahydrofuranyl, or tetrahydropyranyl.

The term "4- to 6-membered nitrogen-containing saturated heterocyclyl group" means a monovalent saturated heterocyclyl group comprising at least one nitrogen atom among "4- to 6-membered saturated heterocycle" as described above. A preferable one is azetidinyl, pyrrolidinyl, piperidinyl, piperazinyl, or morpholinyl.

The term "$C_{6-10}$ aromatic carbocycle" means a monocyclic or bicyclic aromatic hydrocarbon ring having 6 to 10 carbon atoms. Examples of "$C_{6-10}$ aromatic carbocycle" include, for example, benzene, 1-naphthalene, and 2-naphthalene, and preferably benzene.

The term "5- to 10-membered aromatic heterocycle" means a monocyclic or bicyclic aromatic heterocycle consisting of 5 to 10 atoms, comprising the same or different 1 to 3 heteroatoms selected from the group consisting of oxygen atom, nitrogen atom, and sulfur atom. The "5- to 10-membered aromatic heterocycle" includes, preferably a monocyclic or bicyclic "5- to 9-membered aromatic heterocycle", more preferably a monocyclic "5- to 8-membered aromatic heterocycle", further preferably a monocyclic "5- or 6-membered aromatic heterocycle". Examples of "5- to 10-membered aromatic heterocycle" include, for example, pyridine, pyridazine, pyrimidine, pyrazine, triazine, thiophene, pyrrole, thiazole, isothiazole, pyrazole, imidazole, furan, oxazole, isoxazole, oxadiazole, thiadiazole, triazole, tetrazole, quinoline, isoquinoline, naphthyridine, quinazoline, benzofuran, benzothiophene, indole, benzoxazole, benzoisoxazole, 1H-indazole, 2H-indazole, benzimidazole, benzoxadiazole, benzothiadiazole, indolizine, benzofurazine, thienopyrimidine, pyrazolopyridine, imidazopyridine, imidazopyrazine, pyrazolopyrimidine, triazolopyrimidine, thienothiophene, imidazothiazole, chromane, 2,3-dihydrobenzofuran, 1,3-dihydrobenzofuran, 2,3-dihydro-1H-indene, 2,3-dihydro-1H-inden-1-one, 2,3-dihydro-1H-pyrrolopyridine, 2,3-dihydro-1H-pyrrolopyridin-1-one, 1,2-dihydro-3H-pyrrolopyridin-3-one, and 5,6,7,8-tetrahydroimidazopyrazine.

The "5-membered aromatic heterocycle" includes, for example, thiophene, pyrrole, thiazole, isothiazole, pyrazole, imidazole, furan, oxazole, isoxazole, oxadiazole, thiadiazole, triazole, and tetrazole. A preferable one includes thiophene, thiazole, and isothiazole.

The "6-membered aromatic heterocycle" includes, for example, pyridine, pyridazine, pyrimidine, and pyrazine. A preferable one is pyridine.

The term "5- or 6-membered aromatic heterocyclyl group" means a monovalent group of the "5-membered aromatic heterocycle" or "6-membered aromatic heterocycle".

In the present compound of Formula (1), preferable embodiments of $R^1$, $R^2$, $R^3$, $R^4$, $R^5$, $R^6$, $R^a$, $R^b$, $R^c$, $R^d$, $R^e$, Ring A, and X are shown below, but the scope of the present invention is not intended to be limited to the preferable embodiments shown below, each of which may be optionally combined.

Preferably, $R^1$ and $R^2$ are each independently hydrogen atom or $C_{1-4}$ alkyl, wherein the alkyl may be optionally substituted with 1 to 5 substituents independently selected from the group consisting of fluorine atom and $C_{1-4}$ alkoxy. More preferably, $R^1$ and $R^2$ are each independently hydrogen atom, methyl, ethyl, methoxymethyl, or trifluoromethyl, further preferably hydrogen atom or methyl. Particularly preferably, $R^1$ is methyl, and $R^2$ is hydrogen atom.

Preferably, $R^3$ and $R^4$ are each independently hydrogen atom, halogen atom, $C_{1-4}$ alkyl, or $C_{1-4}$ alkoxy, wherein the alkyl and the alkoxy may be optionally substituted with 1 to 5 fluorine atoms. More preferably, $R^3$ and $R^4$ are each independently hydrogen atom, fluorine atom, chlorine atom, methyl, difluoromethyl, trifluoromethyl, methoxy, difluoromethoxy, or trifluoromethoxy, further preferably hydrogen atom, fluorine atom, chlorine atom, difluoromethyl, trifluoromethyl, or difluoromethoxy.

Preferably, $R^5$ and $R^6$ are each independently hydrogen atom, halogen atom, $C_{1-4}$ alkyl, $C_{1-4}$ alkoxy, wherein the alkyl and the alkoxy may be optionally substituted with 1 to 5 fluorine atoms, or —$NR^aR^b$. More preferably, $R^5$ and $R^6$ are each independently hydrogen atom, fluorine atom, chlorine atom, methyl, ethyl, propyl, methoxy, or —$NR^aR^b$, further preferably hydrogen atom, fluorine atom, methyl, ethyl, or —$NR^aR^b$. Still further preferably, they are hydrogen atom, fluorine atom, methyl, or —$NH_2$. Particularly preferably, they are hydrogen atom or —$NH_2$.

Preferably, $R^a$ and $R^b$ are each independently hydrogen atom or $C_{1-4}$ alkyl, wherein the alkyl may be optionally substituted with 1 to 5 fluorine atoms. More preferably, $R^a$ and $R^b$ are each independently hydrogen atom or methyl. Further preferably, both are hydrogen atom.

Preferably, $R^c$ includes $C_{1-4}$ alkyl, wherein the alkyl may be optionally substituted with the same or different 1 to 5 substituents selected from the group consisting of halogen atom, hydroxy, and $C_{1-4}$ alkoxy, more preferably methyl or ethyl, further preferably methyl.

Preferably, $R^d$ includes hydrogen atom and $C_{1-4}$ alkyl, more preferably hydrogen atom or methyl.

Preferably, $R^e$ includes hydrogen atom, $C_{1-4}$ alkyl, and halogen atom, more preferably hydrogen atom or fluorine atom, further preferably hydrogen atom.

Preferably, X includes nitrogen atom and —CH—, further preferably —CH—.

Preferably, Ring A includes benzene, pyridine, thiophene, 1,3-benzodioxole, benzothiophene, benzofuran, and quinoline, more preferably benzene, thiophene, pyridine, or 1,3-benzodioxole, further preferably benzene or pyridine, particularly preferably benzene.

One embodiment of the compound of Formula (1) includes the following (A).

(A)

A compound of Formula (1), or a pharmaceutically acceptable salt thereof,
wherein $R^1$ and $R^2$ are each independently hydrogen atom or methyl;
$R^3$ and $R^4$ are each independently hydrogen atom, fluorine atom, chlorine atom, $C_{1-4}$ alkyl, or $C_{1-4}$ alkoxy, wherein the alkyl and the alkoxy may be optionally substituted with 1 to 5 fluorine atoms;
$R^5$ and $R^6$ are each independently hydrogen atom, fluorine atom, chlorine atom, methyl, ethyl, propyl, methoxy, or —$NR^aR^b$;
$R^a$ and $R^b$ are each independently hydrogen atom, or $C_{1-4}$ alkyl;
$R^e$ is hydrogen atom or fluorine atom;
X is nitrogen atom or —$CR^e$—; and
Ring A is benzene, thiophene, or pyridine.

Another embodiment of the compound of Formula (1) includes the following (B).

(B)

A compound of Formula (1), or a pharmaceutically acceptable salt thereof,
wherein $R^1$ is methyl;
$R^2$ is hydrogen atom;
$R^3$ and $R^4$ are each independently hydrogen atom, fluorine atom, chlorine atom, methyl, difluoromethyl, trifluoromethyl, methoxy, difluoromethoxy, or trifluoromethoxy;
$R^5$ and $R^6$ are each independently hydrogen atom, fluorine atom, methyl, or $NH_2$;
X is —CH—; and
Ring A is benzene or pyridine.

Among the present compounds, more preferable ones are those which show no or only slightly mechanism-based inhibition (MBI) against Cytochrome P450 3A4 (CYP3A4), and which have lower risks for significant side effects such as hepatotoxicity as well as drug-drug interactions.

The term "pharmaceutically acceptable salt" includes acid addition salts, base addition salts, and amino acid salts. For example, the acid addition salts include inorganic acid salts such as hydrochloride, hydrobromide, sulfate, hydroiodide, nitrate, and phosphate and organic acid salts such as citrate, oxalate, phthalate, fumarate, maleate, succinate, malate, acetate, formate, propionate, benzoate, trifluoroacetate, methanesulfonate, benzenesulfonate, para-toluenesulfonate, and camphorsulfonate. The base addition salts include inorganic base salts such as sodium salt, potassium salt, calcium salt, magnesium salt, barium salt, and aluminum salt and organic base salts such as trimethylamine, triethylamine, pyridine, picoline, 2,6-lutidine, ethanolamine, diethanolamine, triethanolamine, tromethamine, tris(hydroxymethyl)methylamine, tert-butylamine, cyclohexylamine, dicyclohexylamine, and N,N-dibenzylethylamine. The amino acid salts include amino acid salts with basic amino acids or acidic amino acids such as arginine, lysine, ornithine, asparagine acid, and glutamic acid. More preferable ones include hydrochloride and phosphate, further preferably a 2.5 phosphate salt.

Preferable salts of starting materials and intermediates and salts acceptable for pharmaceutical materials are commonly-used non-toxic salts. Such salts include acid addition salts such as organic acid salts (e.g., acetate, trifluoroacetate, maleate, fumarate, citrate, tartrate, methanesulfonate, benzenesulfonate, formate, and para-toluenesulfonate) and inorganic acid salts (e.g., hydrochloride, hydrobromide, hydroiodide, sulfate, nitrate, and phosphate), salts with amino acids (e.g., arginine, asparagine acid, and glutamic acid), metal salts such as alkali metal salts (e.g., sodium salt and potassium salt) and alkaline-earth metal salts (e.g., calcium salt and magnesium salt), ammonium salts, organic base salts (e.g., trimethylamine salt, triethylamine salt, pyridine salt, picoline salt, dicyclohexylamine salt, and N,N'-dibenzylethylenediamine salt), and those which a person skilled in the art can optionally select.

When a salt of the present compound is to be obtained, a salt of the present compound may be purified directly in the case where the present compound is obtained in the form of such a salt, whereas in the case where the present compound is obtained in its free form, such a free form may be solved or suspended in an appropriate organic solvent, followed by addition of an acid or base, resulting in the formation of a corresponding salt according to common methods.

The present invention includes a compound of Formula (1), or a pharmaceutically acceptable salt thereof, or a cocrystal. Such a cocrystal includes, for example, a cocrystal (molar ratio of 1:1 to 2.5) of a compound of Formula (1), or a pharmaceutically acceptable salt thereof, with a hydrochloric-acid or phosphoric-acid molecule. The present compound may also exist in the form of a hydrate and/or solvates with various solvents (e.g., ethanolate), and includes these hydrate and/or solvates as well.

The present compound includes those which may have optical isomers based on a chiral center, atropisomers based on axial or planar chirality caused by hindrance of intramolecular rotation, or other isomers such as stereoisomers, tautomers, and geometric isomers, and all possible isomers, including these isomers, and a mixture thereof are encompassed within the scope of the present invention. In addition to the above isomers, any crystalline forms and a mixture thereof are also encompassed in the present invention.

In particular, optical isomers and atropisomers may be obtained in a mixture having a different steric structure such as a racemic mixture or in an optically active substance in the case where optically active starting materials or intermediates are used. Racemates of corresponding starting materials, intermediates, or final products may be physically or chemically separated into their optical enantiomers by known separation procedures, such as a method with an optically active column and fractionated crystallization, at an appropriate step of the preparation process as below, if necessary. For example, in the diastereomer method, two diastereomers are formed from a racemate in a reaction with an optically resolving reagent. Each diastereomer generally has different physical properties, and may be separated by known procedures such as fractionated crystallization.

The present compound encompasses a prodrug of a compound of Formula (1), or a pharmaceutically acceptable salt thereof, as well as the above isomers. The present compound also encompasses compounds where a part or all of atoms constituting a compound of Formula (1) are replaced with isotopes, for example, those which hydrogen is deuterated or tritiated ($^2H$, $^3H$) and those which $^{12}C$ is replaced with $^{14}C$.

The term "prodrug of a compound of Formula (1)" herein means a compound that is converted into a compound of Formula (1) in the reaction with enzymes or gastric acid under physiological conditions in vivo, i.e., a compound that is enzymatically oxidized, reduced, or hydrolyzed to change into a compound of Formula (1), or a compound that is hydrolyzed depending on pH changes with gastric acid to change into a compound of Formula (1).

Preparation of the Present Compound

Preparation of the present compound is illustrated by example hereinafter, but the present invention is not intended to be limited thereto.

The present compound can be prepared by, for example, the methods shown in the following Preparation 1 to 12. These Preparation may be optionally modified on the basis of knowledge of a person skilled in organic synthetic chemistry. Compounds used for starting materials may be substituted with their salts or those which a functional group is protected, if necessary.

In the Preparation as below, when any of functional groups other than a reaction site may change depending on reaction conditions or may not be suitable for treatment after reactions, in addition to the case where the use of a protecting group is explicitly mentioned, any groups other than the reaction site may be protected, if necessary, followed by deprotection after the completion of reaction or a series of reactions, to give a desired product. Such a protecting group includes any common protecting groups described in literature (such as T. W. Greene and P. G. M. Wuts, "Protective Groups in Organic Synthesis", 3rd Ed., John Wiley and Sons, Inc., New York (1999)), and the introduction and removal of such a protecting group may be carried out by or in accordance with methods commonly used in the organic synthetic chemistry (e.g., the methods described in the above literature). Specifically, protecting groups for amino include, for example, benzyloxycarbonyl, tert-butoxycarbonyl, acetyl, and benzyl and those for hydroxy include, for example, trialkylsilyl, acetyl, and benzyl.

Any starting materials and intermediates used in each of the following Preparation are commercially available or can be obtained and synthesized from commercially available compounds or known compounds by or in accordance with methods known by a person skilled in the art. Such starting materials and intermediates may be used in their salt forms or in those which any of functional groups are protected, if necessary.

Any of intermediates and desired compounds in the preparation as below may be converted into any of other compounds encompassed in the present invention by optionally transforming any functional groups thereof or extending various side chains, specifically via amino, hydroxy, carbonyl, or halogen, followed by the above-mentioned protection and deprotection, if necessary. The transformation of functional groups and extension of side chains may be carried out by or in accordance with general methods commonly used (e.g., R. C. Larock, "Comprehensive Organic Transformations", 2nd Ed., John Wiley and Sons Inc., New York (1999)).

The inert solvent used in the Preparation as below means any of solvents that do not react with starting materials, reagents, bases, acids, catalysts, and ligands used in reactions.

Preparation 1

Compound (3) is prepared by, for example, the following process.

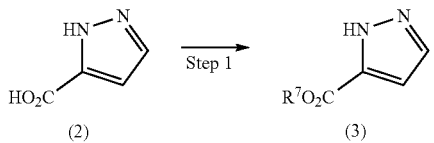

(In the scheme, $R^7$ is methyl or ethyl.)

step 1: Compound (2) may be esterified in a similar manner to known methods (e.g., R. C. Larock, "Comprehensive Organic Transformations", 2nd Ed., John Wiley and Sons inc., New York (1999)) to give Compound (3). Compound (2) may be commercially available or synthesized by known methods.

Preparation 2

Compound (6) is prepared by, for example, the following processes.

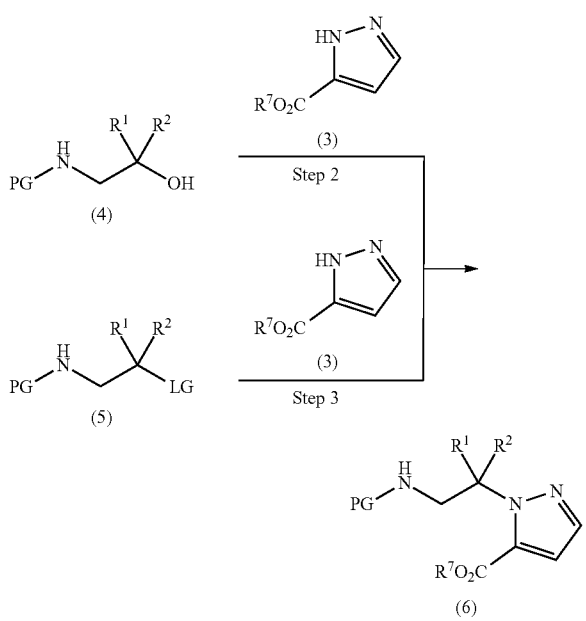

(In the scheme, $R^1$ and $R^2$ are as defined in Item 1; $R^7$ is methyl or ethyl; PG is a protecting group (such as tert-butoxycarbonyl group and benzyloxycarbonyl group); and LG is a leaving group (such as iodine atom, bromine atom, chlorine atom, and substituted sulfonyloxy group (e.g., methanesulfonyloxy group, trifluoromethanesulfonyloxy group, and p-toluenesulfonyloxy group)).)

step 2: Compound (6) may be prepared by Mitsunobu reaction of Compound (3) and Compound (4) in an appropriate inert solvent with conventional methods. Specifically, the reaction may be carried out in the presence of triphenylphosphine or tributylphosphine and a Mitsunobu reaction reagent such as diethyl azodicarboxylate, diisopropyl azodicarboxylate, and N,N,N',N'-tetramethylazodicarboxamide, or with a cyanomethylenephosphorane reagent. The reaction temperature of the present step generally ranges from −20° C. to a boiling point of the solvent used herein. The reaction time of the present step ranges from 1 minute to 5 days. Compounds (3) and (4) may be commercially available or synthesized by known methods.

Examples of the inert solvent used in the present step include, for example, halogenated hydrocarbons such as chloroform and dichloromethane; aromatic hydrocarbons such as benzene and toluene; ether solvents such as tetrahydrofuran, diethyl ether, and 1,4-dioxane; and a mixed solvent thereof.

step 3: Compound (6) may also be prepared by reacting Compound (3) and Compound (5) in the presence of an appropriate base in an appropriate inert solvent according to conventional methods. The reaction may be carried out in the presence of an appropriate phase-transfer catalyst, if necessary. The reaction temperature of the present step generally ranges from −20° C. to a boiling point of the solvent used herein. The reaction time of the present step ranges from 1 minute to 5 days. Compounds (3) and (5) may be commercially available or synthesized by known methods.

Examples of the base used in the present step include, for example, organic bases such as triethylamine, N,N-diisopropylethylamine, and pyridine; inorganic bases such as potassium carbonate, sodium carbonate, cesium carbonate, potassium hydrogen carbonate, sodium hydrogen carbonate, potassium dihydrogen phosphate, dipotassium hydrogen phosphate, potassium phosphate, sodium dihydrogen phosphate, disodium hydrogen phosphate, sodium phosphate, potassium hydroxide, sodium hydroxide, and sodium hydride; and metal alkoxides such as sodium methoxide and potassium tert-butoxide.

Examples of the phase-transfer catalyst used in the present step include, for example, tetrabutylammonium hydrogen sulfate.

Examples of the inert solvent used in the present step include, for example, halogenated hydrocarbons such as chloroform and dichloromethane; ketones such as acetone and methyl ketone; aromatic hydrocarbons such as benzene and toluene; ether solvents such as tetrahydrofuran, diethyl ether, 1,4-dioxane, and 1,2-dimethoxyethane; lower alcohols such as methanol, ethanol, and 2-propanol; aprotic polar solvents such as acetonitrile, N,N-dimethylformamide, and N-methyl-2-pyrrolidone; water; and a mixed solvent thereof.

Preparation 3

Compound (9) is prepared by, for example, the following processes.

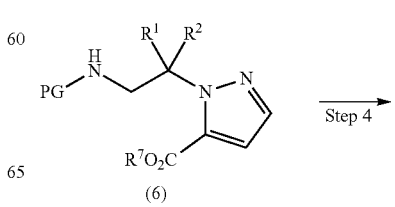

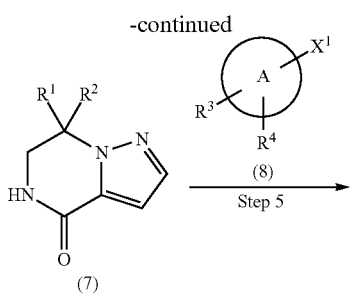

(7)

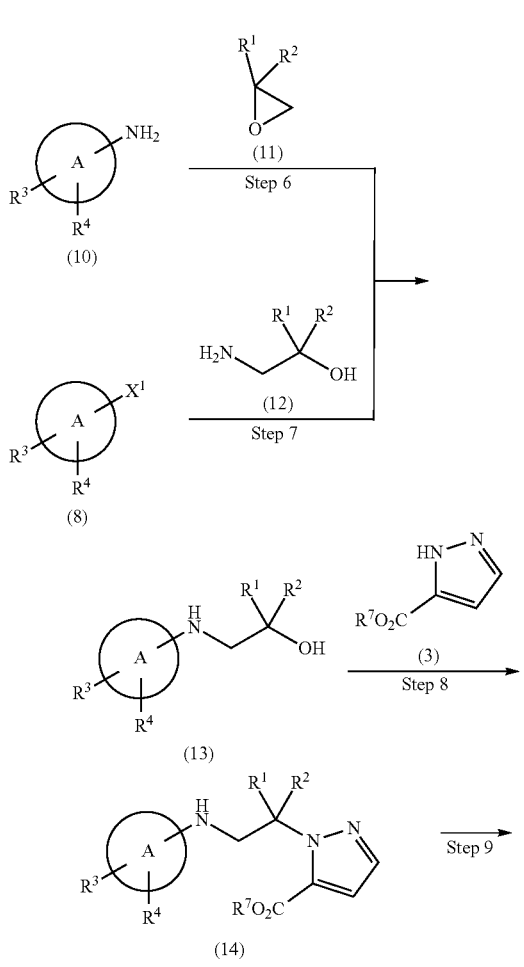

(In the scheme, Ring A, $R^1$, $R^2$, $R^3$, and $R^4$ are as defined in Item 1; $R^7$ is methyl or ethyl; PG is a protecting group such as tert-butoxycarbonyl group and benzyloxycarbonyl group; and $X^1$ is iodine, bromine, or chlorine.)

step 4: Compound (7) may be prepared by removing a protecting group of amine, PG, from Compound (6) in an appropriate inert solvent by any of various methods known to a person skilled in the art (see T. W. Greene and P. G. M. Wuts, "Protective Groups in Organic Synthesis", 3rd Ed., John Wiley and Sons, inc., New York (1999)), followed by cyclization in the presence of an appropriate base or acid. In the present step, the removal of a protecting group and cyclization may also be carried out simultaneously in a single reaction system in the presence of an appropriate base or acid in an appropriate inert solvent according to conventional methods. The reaction temperature of the present step generally ranges from –20° C. to a boiling point of the solvent used herein. The reaction time of the present step ranges from 1 minute to 5 days.

Examples of the base used in the present step include, for example, organic bases such as triethylamine and pyridine; inorganic bases such as potassium carbonate and sodium carbonate; and metal alkoxides such as potassium tert-butoxide.

Examples of the acid used in the present step include, for example, inorganic acids such as hydrochloric acid and sulfuric acid and organic acids such as acetic acid and trifluoroacetic acid.

Examples of the inert solvent used in the present step include, for example, halogenated hydrocarbons such as chloroform and dichloromethane; aromatic hydrocarbons such as benzene and toluene; ether solvents such as tetrahydrofuran, diethyl ether, 1,4-dioxane, and 1,2-dimethoxyethane; lower alcohols such as methanol, ethanol, and 2-propanol; aprotic polar solvents such as acetonitrile, N,N-dimethylformamide, and N-methyl-2-pyrrolidone; organic acids such as acetic acid; and a mixed solvent thereof.

step 5: Compound (9) may be prepared in a coupling reaction of Compound (7) and Compound (8) in the presence of an appropriate transition metal catalyst and base in an appropriate inert solvent according to conventional methods. The reaction may be carried out in the presence of an appropriate ligand, if necessary. The reaction temperature of the present step generally ranges from room temperature to a boiling point of the solvent used herein. The reaction time of the present step ranges from 1 minute to 5 days. Compound (8) may be commercially available or synthesized by known methods.

Examples of the transition metal catalyst used in the present step include, for example, palladium (II) acetate, tris(dibenzylideneacetone)dipalladium (0), bis(tri-tert-butylphosphine)palladium (0), copper (I) iodide, and copper (II) oxide.

Examples of the ligand used in the present step include, for example, tri-tert-butylphosphine, 2-dicyclohexylphosphino-2',4',6'-triisopropylbiphenyl, 4,5-bis(diphenylphosphino)-9,9-dimethylxanthene, and N,N'-dimethylethylenediamine.

Examples of the base used in the present step include, for example, metal alkoxides such as sodium tert-butoxide and inorganic bases such as tripotassium phosphate and potassium carbonate.

Examples of the inert solvent used in the present step include, for example, aromatic hydrocarbons such as benzene and toluene; ether solvents such as tetrahydrofuran, diethyl ether, 1,4-dioxane, and 1,2-dimethoxyethane; aprotic polar solvents such as N,N-dimethylformamide and N,N-dimethylacetamide; and a mixed solvent thereof.

Preparation 4

Compound (9) is also prepared by, for example, the following processes.

-continued

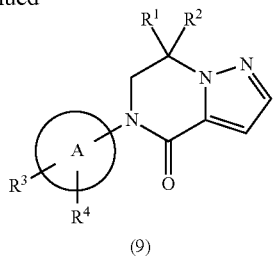

(9)

(In the scheme, Ring A, $R^1$, $R^2$, $R^3$, and $R^4$ are as defined in Item 1; and $R^7$ and $X^1$ are as defined above.)

step 6: Compound (13) may be prepared by reacting Compound (10) and Compound (11) in an appropriate inert solvent according to conventional methods. The reaction may be carried out in the presence of a base or acid with an appropriate additive, if needed, and in the presence of an appropriate phase-transfer catalyst. The reaction temperature of the present step generally ranges from −20° C. to a boiling point of the solvent used herein. The reaction time of the present step ranges from 1 minute to 10 days. Compounds (10) and (11) may be commercially available or synthesized by known methods.

Examples of the additive used in the present step include, for example, lithium bromide.

Examples of the base used in the present step include, for example, organic bases such as triethylamine and pyridine; and inorganic bases such as potassium carbonate, sodium carbonate, potassium hydroxide, and sodium hydroxide.

Examples of the acid used in the present step include, for example, inorganic acids such as hydrochloric acid and sulfuric acid and organic acids such as p-toluenesulfonic acid and trifluoroacetic acid.

Examples of the inert solvent used in the present step include, for example, halogenated hydrocarbons such as chloroform and dichloromethane; aromatic hydrocarbons such as benzene and toluene; ether solvents such as tetrahydrofuran, diethyl ether, 1,4-dioxane, and 1,2-dimethoxyethane; lower alcohols such as methanol, ethanol, and 2-propanol; aprotic polar solvents such as acetonitrile, N,N-dimethylformamide, and N-methyl-2-pyrrolidone; and a mixed solvent thereof.

step 7: Compound (13) may also be prepared by coupling Compound (8) and Compound (12) in the presence of an appropriate transition metal catalyst and base in an appropriate inert solvent or under solvent-free condition.

The reaction temperature of the present step generally ranges from −20° C. to a boiling point of the solvent used herein. The reaction time of the present step ranges from 1 minute to 5 days. Compound (8) and Compound (12) may be commercially available or synthesized by known methods.

Examples of the transition metal catalyst used in the present step include, for example, palladium (II) acetate, tris(dibenzylideneacetone)dipalladium (0), bis(tri-tert-butylphosphine)palladium (0), copper (I) chloride, copper (I) bromide, copper (I) iodide, copper (I) acetate, and copper (II) oxide.

Examples of the base used in the present step include, for example, organic bases such as triethylamine and pyridine; and inorganic bases such as potassium carbonate, sodium carbonate, cesium carbonate, potassium hydroxide, and sodium hydroxide.

Examples of the inert solvent used in the present step include, for example, halogenated hydrocarbons such as chloroform and dichloromethane; aromatic hydrocarbons such as benzene and toluene; ether solvents such as tetrahydrofuran, diethyl ether, 1,4-dioxane, and 1,2-dimethoxyethane; lower alcohols such as methanol, ethanol, and 2-propanol; aprotic polar solvents such as acetonitrile, N,N-dimethylformamide, N-methyl-2-pyrrolidone, and dimethylsulfoxide; water; and a mixed solvent thereof.

step 8: Compound (14) may be prepared by Mitsunobu reaction of Compound (3) and Compound (13) in an appropriate inert solvent according to conventional methods. Specifically, the reaction may be carried out in the presence of triphenylphosphine or tributylphosphine and a Mitsunobu reaction reagent such as diethyl azodicarboxylate, diisopropyl azodicarboxylate, and N,N,N',N'-tetramethylazodicarboxamide, or with a cyanomethylenephosphorane reagent. The reaction temperature of the present step generally ranges from −20° C. to a boiling point of the solvent used herein. The reaction time of the present step ranges from 1 minute to 5 days. Compound (3) may be commercially available or synthesized by known methods.

Examples of the inert solvent used in the present step include, for example, aromatic hydrocarbons such as benzene and toluene; ether solvents such as tetrahydrofuran, diethyl ether, and 1,4-dioxane; and a mixed solvent thereof.

step 9: Compound (9) may be prepared by cyclization of Compound (14) in the presence of an appropriate base or acid in an appropriate inert solvent according to conventional methods. The reaction temperature of the present step generally ranges from −20° C. to a boiling point of the solvent used herein. The reaction time of the present step ranges from 1 minute to 5 days.

Examples of the base used in the present step include, for example, organic bases such as triethylamine and pyridine; inorganic bases such as potassium carbonate and sodium carbonate; and metal alkoxides such as potassium tert-butoxide.

Examples of the acid used in the present step include, for example, inorganic acids such as hydrochloric acid and sulfuric acid and organic acids such as p-toluenesulfonic acid monohydrate, acetic acid, and trifluoroacetic acid.

Examples of the inert solvent used in the present step include, for example, halogenated hydrocarbons such as chloroform and dichloromethane; aromatic hydrocarbons such as benzene and toluene; ether solvents such as tetrahydrofuran, diethyl ether, 1,4-dioxane, and 1,2-dimethoxyethane; lower alcohols such as methanol, ethanol, and 2-propanol; aprotic polar solvents such as acetonitrile, N,N-dimethylformamide, and N-methyl-2-pyrrolidone; and a mixed solvent thereof.

Preparation 5

Compound (15) is prepared by, for example, the following process.

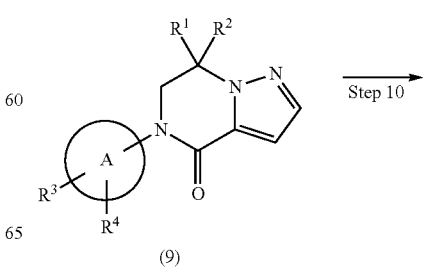

(9)

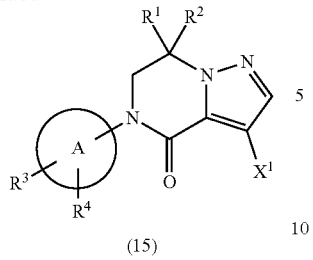

(In the scheme, Ring A, $R^1$, $R^2$, $R^3$, and $R^4$ are as defined in Item 1; and $X^1$ is as defined above.)

step 10: Compound (15) may be prepared by reacting Compound (9) and an appropriate halogenating agent in an appropriate inert solvent according to conventional methods. The reaction may be carried out in the presence of an appropriate additive or acid, if necessary. The reaction temperature of the present step generally ranges from −20° C. to a boiling point of the solvent used herein. The reaction time of the present step ranges from 1 minute to 5 days.

Examples of the halogenating agent used in the present step include, for example, N-iodosuccinimide, N-bromosuccinimide, N-chlorosuccinimide, iodine, iodine monochloride, bromine, and 1,3-diiodo-5,5-dimethylhydantoin.

Examples of the additive used in the present step include, for example, ammonium cerium (IV) nitrate, sodium acetate, and iron.

Examples of the acid used in the present step include, for example, hydrochloric acid, sulfuric acid, acetic acid, para-toluenesulfonic acid, and pyridinium para-toluenesulfonate.

Examples of the inert solvent used in the present step include, for example, halogenated hydrocarbons such as chloroform, dichloromethane, and carbon tetrachloride; aprotic polar solvents such as N,N-dimethylformamide and ethyl acetate; protic polar solvents such as acetic acid; and a mixed solvent thereof.

Preparation 6

Compound (1) is prepared by, for example, the following process.

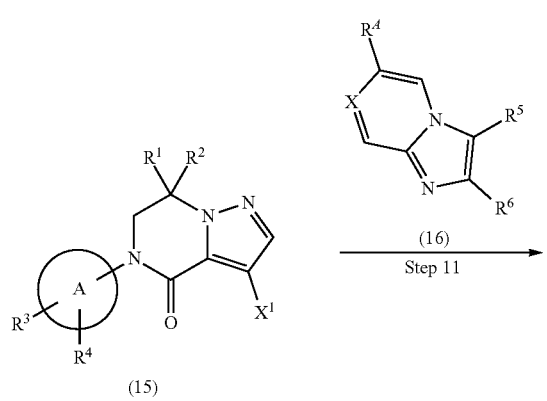

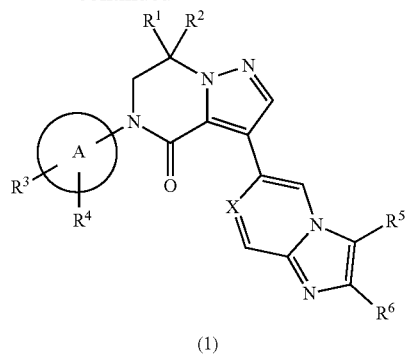

(In the scheme, Ring A, X, $R^1$, $R^2$, $R^3$, $R^4$, $R^5$, and $R^6$ are as defined in Item 1; $X^1$ is as defined above; and $R^A$ is boronic acid or boronic acid ester.)

step 11: Compound (1) may be prepared in a coupling reaction of Compound (15) and Compound (16) in the presence of an appropriate transition metal catalyst and base in an appropriate inert solvent according to conventional methods. The present step may also be carried out in the presence of an appropriate ligand, if necessary. The reaction temperature of the present step generally ranges from room temperature to a boiling point of the solvent used herein, preferably from 50° C. to 150° C. The reaction time of the present step generally ranges from 1 minute to 5 days, preferably from 1 minute to 2 days. The present step may also be carried out under microwave irradiation. Compound (16) may be commercially available or synthesized by known methods.

Examples of the transition metal catalyst used in the present step include, for example, tetrakis(triphenylphosphine)palladium (0), palladium (II) acetate, palladium (II) chloride, tris(dibenzylideneacetone)dipalladium (0), dichlorobis(triphenylphosphine)palladium (II), dichloro[1,1'-bis(diphenylphosphino)ferrocene]palladium (II) dichloromethane adduct, and dichlorobis[di-tert-butyl(4-dimethylaminophenyl)phosphino]palladium (II).

Examples of the base used in the present step include, for example, sodium carbonate, potassium carbonate, cesium carbonate, sodium hydroxide, potassium hydroxide, and potassium phosphate.

Examples of the ligand used in the present step include, for example, triphenylphosphine, tri-tert-butylphosphine, 2-dicyclohexylphosphino-2',6'-dimethoxybiphenyl, and 2-dicyclohexylphosphino-2',4',6'-triisopropylbiphenyl.

Examples of the inert solvent used in the present step include, for example, ether solvents such as tetrahydrofuran, diethyl ether, 1,4-dioxane, and 1,2-dimethoxyethane; aprotic polar solvents such as N,N-dimethylformamide, N,N-dimethylacetamide, N-methyl-2-pyrrolidone, and acetonitrile; aromatic hydrocarbons such as benzene and toluene; water; and a mixed solvent thereof.

Preparation 7

Compound (1) is also prepared by, for example, the following processes.

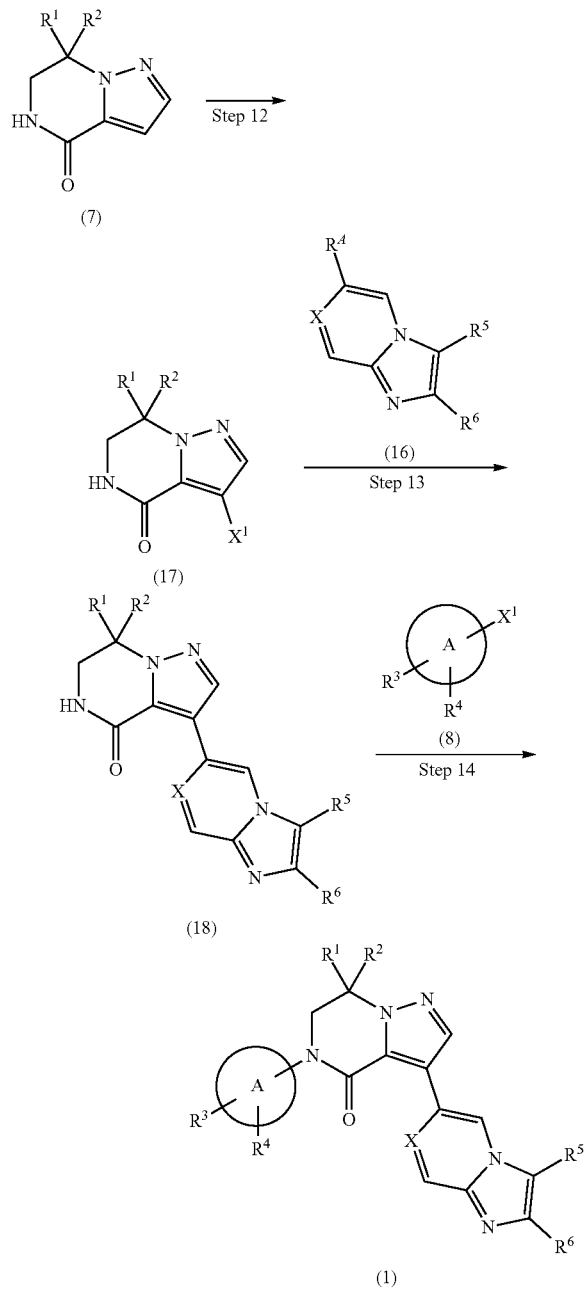

(In the scheme, Ring A, X, $R^1$, $R^2$, $R^3$, $R^4$, $R^5$, and $R^E$ are as defined in Item 1; and $X^1$ and $R^A$ are as defined above.)

step 12: Compound (17) may be prepared in a similar manner to step 10 with Compound (7).

step 13: Compound (18) may be prepared in a similar manner to step 11 with Compound (17) and Compound (16).

step 14: Compound (1) may be prepared in a similar manner to step 5 with Compound (8) and Compound (18).

Preparation 8

Compound (1) is also prepared by, for example, the following processes.

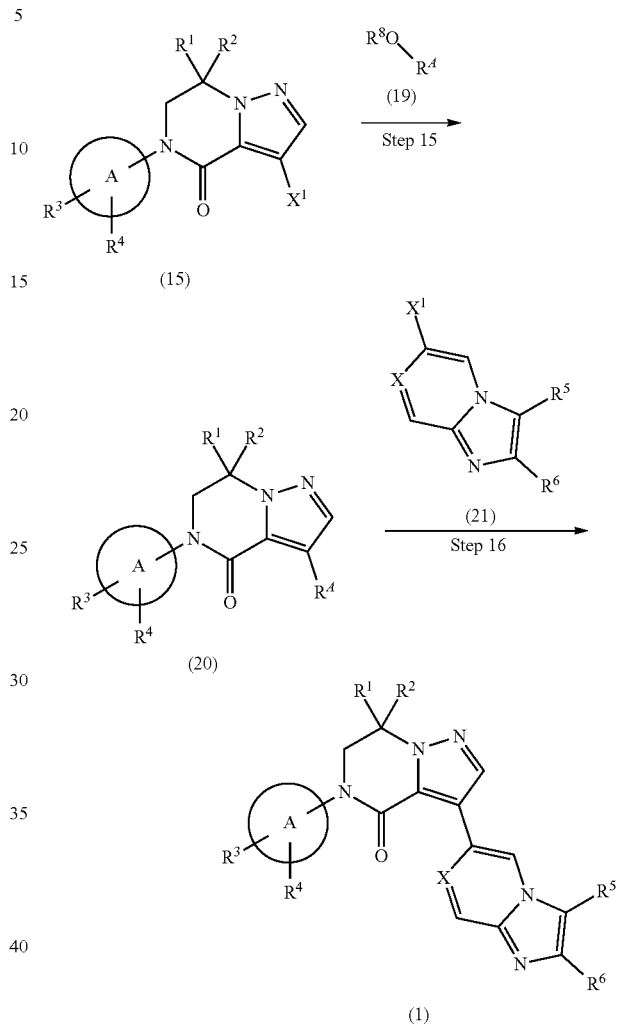

(In the scheme, Ring A, X, $R^1$, $R^2$, $R^3$, $R^4$, $R^5$, and $R^6$ are as defined in Item 1; $X^1$ and $R^A$ are as defined above; and $R^8$ is $C_{1-4}$ alkyl.)

step 15: Compound (20) may be prepared by reacting Compound (15) and Compound (19) in the presence of an appropriate base in an appropriate inert solvent according to conventional methods. The reaction temperature of the present step generally ranges from −78° C. to a boiling point of the solvent used herein, preferably from −78° C. to room temperature. The reaction time of the present step generally ranges from 1 minute to 5 days, preferably from 1 minute to 2 days. Compound (19) may be commercially available or synthesized by known methods.

Examples of the base used in the present step include, for example, isopropylmagnesium chloride-lithium chloride complex, n-butyllithium, sec-butyllithium, tert-butyllithium, lithium diisopropylamide, lithium tetramethylpiperidide, lithium hexamethyldisilazide, sodium hexamethyldisilazide, and potassium hexamethyldisilazide.

Examples of the inert solvent used in the present step include, for example, ether solvents such as tetrahydrofuran, diethyl ether, 1,4-dioxane, and 1,2-dimethoxyethane; saturated hydrocarbons such as n-hexane, n-heptane, and cyclohexane; and a mixed solvent thereof.

step 16: Compound (1) may be prepared in a similar manner to step 11 with Compound (20) and Compound (21). Compound (21) may be commercially available or synthesized by known methods.

Preparation 9

Compound (15) is also prepared by, for example, the following processes.

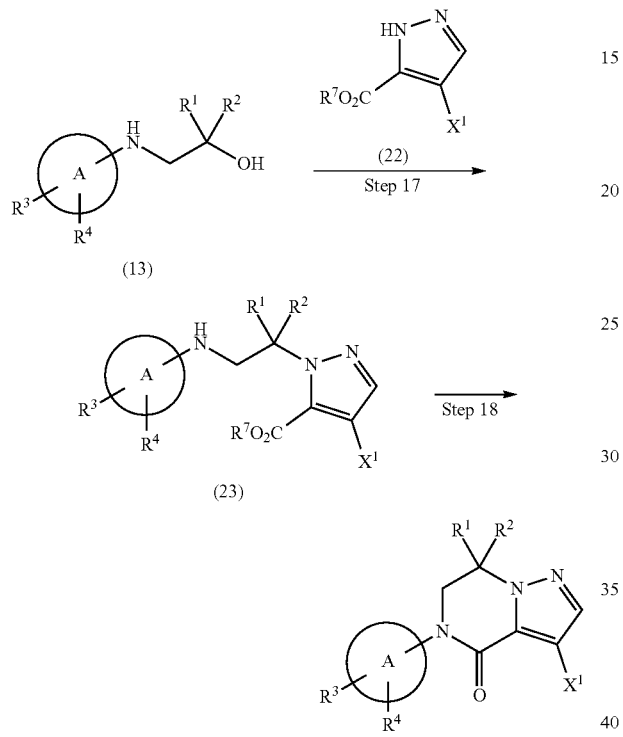

(In the scheme, Ring A, $R^1$, $R^2$, $R^3$, and $R^4$ are as defined in Item 1; and $R^7$ and $X^1$ are as defined above.)

step 17: Compound (23) may be prepared in a similar manner to step 8 with Compound (13) and Compound (22). Compound (22) may be commercially available or synthesized by known methods.

step 18: Compound (15) may be prepared in a similar manner to step 9 with Compound (23).

Preparation 10

Compound (15) is also prepared by, for example, the following processes.

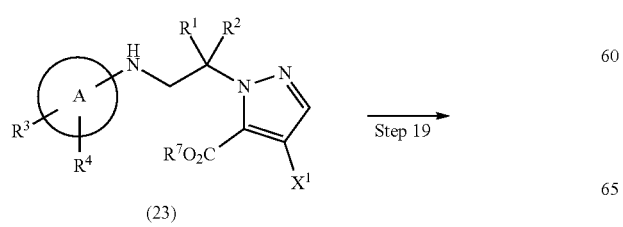

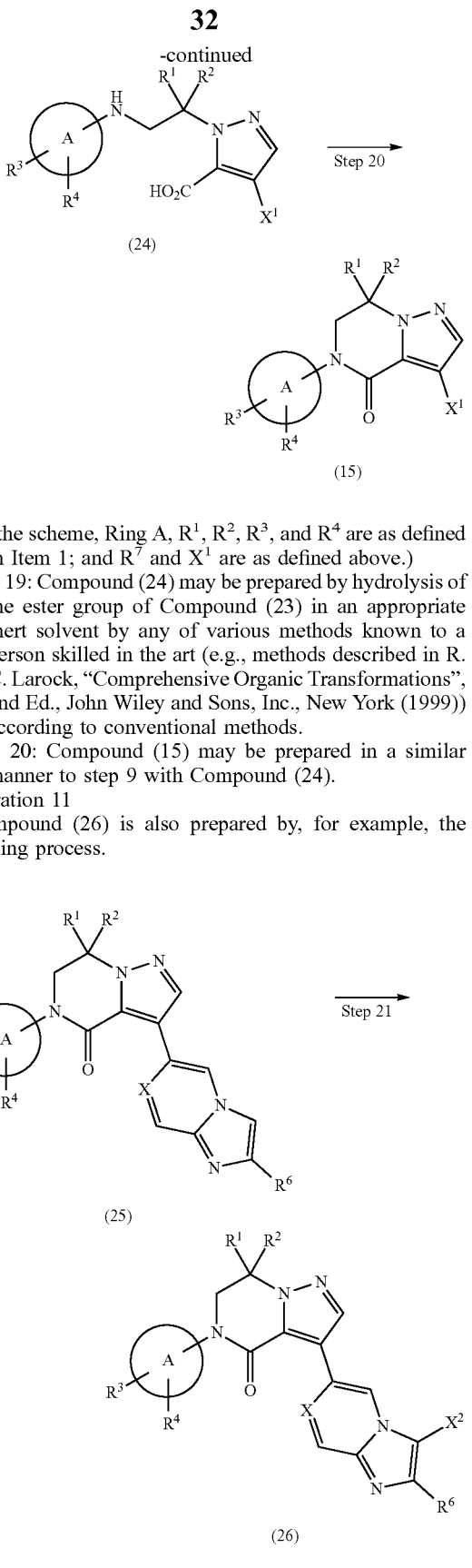

(In the scheme, Ring A, $R^1$, $R^2$, $R^3$, and $R^4$ are as defined in Item 1; and $R^7$ and $X^1$ are as defined above.)

step 19: Compound (24) may be prepared by hydrolysis of the ester group of Compound (23) in an appropriate inert solvent by any of various methods known to a person skilled in the art (e.g., methods described in R. C. Larock, "Comprehensive Organic Transformations", 2nd Ed., John Wiley and Sons, Inc., New York (1999)) according to conventional methods.

step 20: Compound (15) may be prepared in a similar manner to step 9 with Compound (24).

Preparation 11

Compound (26) is also prepared by, for example, the following process.

(In the scheme, Ring A, X, $R^1$, $R^2$, $R^3$, $R^4$, and $R^6$ are as defined in Item 1; and $X^2$ is fluorine atom, chlorine atom, bromine atom, or iodine atom.)

step 21: Compound (26) may be prepared by reacting Compound (25) and a halogenating agent in an appropriate inert solvent according to conventional methods. The reaction may also be carried out in the presence of an additive or acid, if necessary. The reaction temperature generally ranges from −20° C. to a boiling point of the solvent used herein. The reaction time ranges from 1 minute to 5 days.

Examples of the halogenating agent herein include, for example, 1-fluoro-4-methyl-1,4-diazoniabicyclo[2,2,2]octane bis(tetrafluoroborate), 1-fluoropyridinium trifluoromethanesulfonate, N-fluorobenzenesulfonimide, N-iodosuccinimide, N-bromosuccinimide, N-chlorosuccinimide, iodine, iodine monochloride, bromine, and 1,3-diiodo-5,5-dimethylhydantoin.

Examples of the additive herein include, for example, ammonium cerium (IV) nitrate, sodium acetate, and iron.

Examples of the acid herein include, for example, hydrochloric acid, sulfuric acid, acetic acid, para-toluenesulfonic acid, and pyridinium para-toluenesulfonate.

Examples of the inert solvent herein include, for example, halogenated hydrocarbons such as chloroform, dichloromethane, and carbon tetrachloride; aprotic polar solvents such as acetonitrile, N,N-dimethylformamide, and ethyl acetate; protic polar solvents such as acetic acid; and a mixed solvent thereof.

Preparation 12

Compound (1) is also prepared by, for example, the following processes.

metal catalyst in an appropriate inert solvent. The present step may also be carried out in the presence of an appropriate base and/or an appropriate ligand, if necessary. The reaction temperature of the present step generally ranges from room temperature to a boiling point of the solvent used herein, preferably from 50° C. to 150° C. The reaction time of the present step generally ranges from 1 minute to 5 days, preferably from 1 minute to 2 days. The present step may also be carried out under microwave irradiation.

Examples of the boronic acid used in the present step include, for example, methylboronic acid, ethylboronic acid, and trimethylboroxine; but are not limited thereto.

Examples of the alkylzinc reagent used in the present step include, for example, methylzinc chloride and ethylzinc chloride; but are not limited thereto.

Examples of the transition metal catalyst used in the present step include, for example, tetrakis(triphenylphosphine)palladium (0), palladium (II) acetate, palladium (II) chloride, tris(dibenzylideneacetone)dipalladium (0), dichlorobis(triphenylphosphine)palladium (II), dichloro[1,1'-bis(diphenylphosphino)ferrocene]palladium (II) dichloromethane adduct, dichlorobis[di-tert-butyl(4-dimethylaminophenyl)phosphino]palladium (II), and bis(tri-tert-butylphosphine)palladium (0); but are not limited thereto.

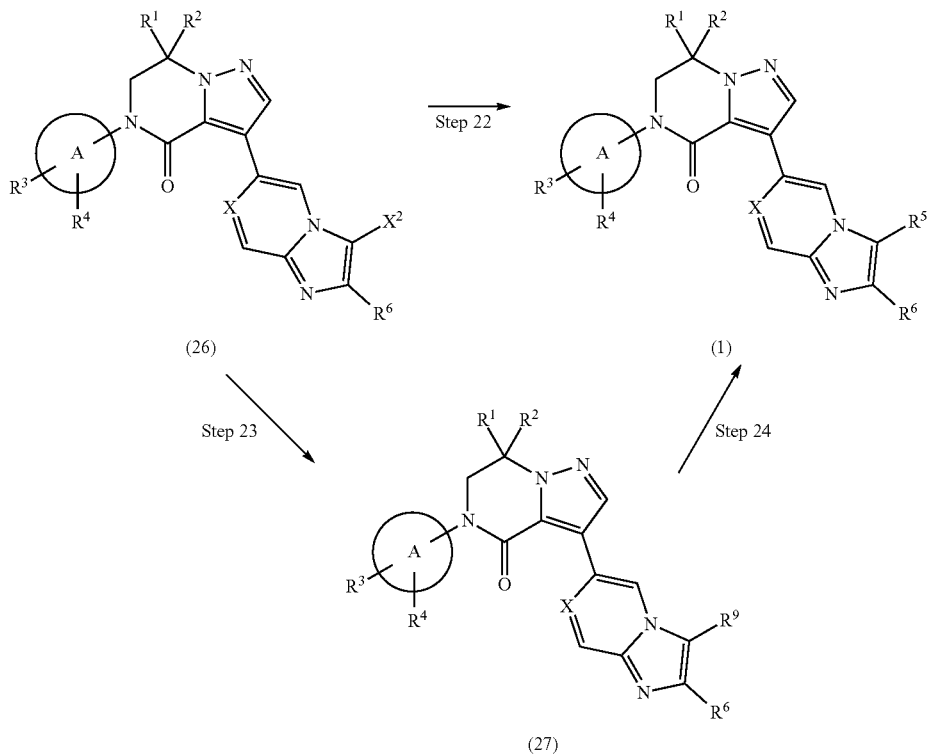

(In the scheme, Ring A, X, $R^1$, $R^2$, $R^3$, $R^4$, $R^5$, and $R^6$ are as defined in Item 1; $X^2$ is as defined above; and $R^9$ is vinyl or allyl.)

step 22: Compound (1) may be prepared by coupling Compound (26) and a boronic acid reagent or alkylzinc reagent in the presence of an appropriate transition Examples of the base used in the present step include, for example, sodium carbonate, potassium carbonate, cesium carbonate, sodium hydroxide, potassium hydroxide, and potassium phosphate; but are not limited thereto.

Examples of the ligand used in the present step include, for example, triphenylphosphine, tri-tert-butylphosphine, 2-dicyclohexylphosphino-2',6'-dimethoxybiphenyl, and 2-dicyclohexylphosphino-2',4',6'-triisopropylbiphenyl; but are not limited thereto.

Examples of the inert solvent used in the present step include, for example, ether solvents such as tetrahydrofuran, diethyl ether, 1,4-dioxane, and 1,2-dimethoxyethane; aprotic polar solvents such as N,N-dimethylformamide, N,N-dimethylacetamide, N-methyl-2-pyrrolidone, and acetonitrile; aromatic hydrocarbons such as benzene and toluene; water; and a mixed solvent thereof; but are not limited thereto.

step 23: Compound (27) may be prepared in a coupling reaction of Compound (26) and a boronic acid reagent in the presence of an appropriate transition metal catalyst and an appropriate base in an appropriate inert solvent according to conventional methods. The present step may also be carried out in the presence of an appropriate ligand, if necessary. The reaction temperature of the present step generally ranges from room temperature to a boiling point of the solvent used herein, preferably from 50° C. to 150° C. The reaction time of the present step generally ranges from 1 minute to 5 days, preferably from 1 minute to 2 days. The present step may also be carried out under microwave irradiation.

Examples of the boronic acid used in the present step include, for example, 4,4,5,5-tetramethyl-2-vinyl-1,3,2-dioxaborolane, cis-propenylboronic acid, trans-propenylboronic acid, and allylboronic acid pinacol ester; but are not limited thereto.

Examples of the transition metal catalyst used in the present step include, for example, tetrakis(triphenylphosphine)palladium (0), palladium (II) acetate, palladium (II) chloride, tris(dibenzylideneacetone)dipalladium (0), dichlorobis(triphenylphosphine)palladium (II), dichloro[1,1'-bis(diphenylphosphino)ferrocene]palladium (II) dichloromethane adduct, and dichlorobis[di-tert-butyl(4-dimethylaminophenyl)phosphino]palladium (II); but are not limited thereto.

Examples of the base used in the present step include, for example, sodium carbonate, potassium carbonate, cesium carbonate, sodium hydroxide, potassium hydroxide, and potassium phosphate; but are not limited thereto.

Examples of the ligand used in the present step include, for example, triphenylphosphine, tri-tert-butylphosphine, 2-dicyclohexylphosphino-2',6'-dimethoxybiphenyl, and 2-dicyclohexylphosphino-2',4',6'-triisopropylbiphenyl; but are not limited thereto.

Examples of the inert solvent used in the present step include, for example, ether solvents such as tetrahydrofuran, diethyl ether, 1,4-dioxane, and 1,2-dimethoxyethane; aprotic polar solvents such as N,N-dimethylformamide, N,N-dimethylacetamide, N-methyl-2-pyrrolidone, and acetonitrile; aromatic hydrocarbons such as benzene and toluene; water; and a mixed solvent thereof; but are not limited thereto.

step 24: Compound (1) may be prepared by hydrogenation of an unsaturated carbon bond of Compound (27) in an appropriate inert solvent by any of various methods known to a person skilled in the art (e.g., methods described in R. C. Larock, "Comprehensive Organic Transformations", 2nd Ed., John Wiley and Sons, Inc., New York (1999)) according to conventional methods. The reaction temperature of the present step generally ranges from room temperature to a boiling point of the solvent used herein. The reaction time of the present step ranges from 1 minute to 5 days.

Bases used in each step of each Preparation should be selected appropriately depending on reactions and starting materials, and include, for example, alkali bicarbonates such as sodium bicarbonate and potassium bicarbonate; alkali carbonates such as sodium carbonate and potassium carbonate; metal hydrides such as sodium hydride and potassium hydride; alkali metal hydroxides such as sodium hydroxide and potassium hydroxide; alkali metal alkoxides such as sodium methoxide and sodium tert-butoxide; organic metal bases such as butyllithium and lithium diisopropylamide; and organic bases such as triethylamine, diisopropylethylamine, pyridine, 4-dimethylaminopyridine (DMAP), and 1,8-diazabicyclo[5.4.0]-7-undecene (DBU).

Solvents used in each step of each Preparation should be selected appropriately depending on reactions and starting materials, and include, for example, alcohols such as methanol, ethanol, and isopropanol; ketones such as acetone and methyl ketone; halogenated hydrocarbons such as methylene chloride and chloroform; ethers such as tetrahydrofuran (THF) and 1,4-dioxane; aromatic hydrocarbons such as toluene and benzene; aliphatic hydrocarbons such as hexane and heptane; esters such as ethyl acetate and propyl acetate; amides such as N,N-dimethylformamide (DMF) and N-methyl-2-pyrrolidone; sulfoxides such as dimethylsulfoxide (DMSO); and nitriles such as acetonitrile; and these solvents may be used in a single component or in a mixture of any two or more solvents. An organic base may be used in place of a solvent depending on reactions.

Intermediates and desired compounds in each Preparation may be isolated with purification procedures commonly used in the organic synthetic chemistry, such as neutralization, filtration, extraction, washing, drying, concentration, recrystallization, and a variety of chromatography (e.g., silica gel column chromatography, ion-exchange column chromatography, and preparative liquid chromatography). Solvents for recrystallization include, for example, alcohol solvents such as methanol, ethanol, and 2-propanol; ether solvents such as diethyl ether; ester solvents such as ethyl acetate; aromatic hydrocarbon solvents such as benzene and toluene; ketone solvents such as acetone; halogen solvents such as dichloromethane and chloroform; hydrocarbon solvents such as hexane; aprotic solvents such as N,N-dimethylformamide and acetonitrile; water; and a mixed solvent thereof. Other purification procedures include methods described in Experimental Chemistry (edited by The Chemical Society of Japan, Maruzen) vol. 1. Molecular structures of the present compound can readily be determined by spectroscopy such as the nuclear magnetic resonance method, infrared absorption technique, and circular dichroic spectroscopy and mass spectroscopy with reference to corresponding structures derived from starting materials. Intermediates may also be used in a next reaction without any specific purification.

The present compound may cause asymmetry or have a substituent with an asymmetric carbon, and such a compound may have optical isomers. The present compound includes a mixture of these isomers and a separated isomer, and may be prepared according to conventional methods. Such methods include, for example, those using a starting material with an asymmetric center and those which asymmetry is introduced during any of intermediate steps. For example, an optical isomer may be obtained by starting from a corresponding optically active starting material or by optical resolution in any of appropriate steps during its preparation process. Such optical resolution includes, for example, HPLC with a separation column for optical isomers. When a compound of Formula (1) or intermediates thereof may have a basic functional group, diastereomer technique may be used to form a corresponding salt with an optically active acid (e.g., monocarboxylic acid such as mandelic acid, N-benzyloxyalanine, and lactic acid; dicarboxylic acid such as tartaric acid, o-diisopropylidenetartaric acid, and malic acid; and sulfonic acid such as camphorsulfonic acid and bromocamphorsulfonic acid) in an inert solvent (e.g., alcohol solvents such as methanol, ethanol, and 2-propanol; ether solvents such as diethyl ether; ester solvents such as ethyl acetate; hydrocarbon solvents such as toluene; aprotic solvents such as acetonitrile; and a mixed solvent of any two or more selected from the above-mentioned solvents). When the present compound or intermediates thereof may have an acidic functional group such as carboxyl group, optical resolution may be carried out to form a corresponding salt with an optically active amine (e.g., organic amines such as 1-phenylethylamine, quinine, quinidine, cinchonidine, cinchonine, and strychnine).

The temperature forming a salt is selected from the range from −50° C. to a boiling point of a solvent, preferably the range from 0° C. to a boiling point, more preferably the range from room temperature to a boiling point of a solvent. In order to improve the optical purity, it is desirable to increase the temperature to around a boiling point of a solvent. A salt precipitated may be optionally cooled down to be collected by filtration so as to improve yields. The amount of an optically active acid or amine used ranges from about 0.5 to about 2.0 equivalents to a corresponding substrate, preferably around 1 equivalent. A crystal may be optionally recrystallized in an inert solvent (e.g., alcohol solvents such as methanol, ethanol, and 2-propanol; ether solvent such as diethyl ether; ester solvents such as ethyl acetate; hydrocarbon solvents such as toluene; aprotic solvents such as acetonitrile; and a mixed solvent of any two or more selected from the above-mentioned solvents) to give a corresponding highly-pure optically-active salt. An optically resolved salt may be optionally treated with an acid or base according to conventional methods to give a corresponding free form.

The present compound has mGlu2 receptor negative allosteric modulator (NAM) activity, and may be a novel therapeutic agent and/or preventive agent for diseases involving Group II mGlu receptors (i.e., metabotropic glutamate receptor subtype 2 (mGluR2) and/or metabotropic glutamate receptor subtype 3 (mGluR3), preferably mGluR2), which shows negative allosteric modulation to Group II mGlu receptors. Such diseases involving Group II mGlu receptors include psychiatric diseases and neurodegenerative diseases, specifically major depressive disorder, depressive disorders (such as major depression, treatment-resistant depression, and chronic depression), bipolar and related disorders (such as bipolar depression), anxiety disorders (such as generalized anxiety disorder, panic disorder, social anxiety disorder, and specific phobia), posttraumatic stress disorder, obsessive-compulsive disorder, acute stress disorder, schizophrenia, autism spectrum disorder, Alzheimer's disease, cognitive dysfunction, dementia, drug dependence, obesity, seizure, tremor, pain, and sleep disorder.

Among these psychiatric diseases and neurodegenerative diseases, a preferable subject disease is major depressive disorder, depressive disorders (such as major depression, treatment-resistant depression, and chronic depression), bipolar and related disorders (such as bipolar depression), anxiety disorders (such as generalized anxiety disorder, panic disorder, social anxiety disorder, and specific phobia), posttraumatic stress disorder, obsessive-compulsive disorder, acute stress disorder, Alzheimer's disease, cognitive dysfunction, dementia, drug dependence, obesity, seizure, tremor, pain, or sleep disorder.

The administration route of the present compound may be any of oral, parenteral, or intrarectal administration, and the daily dose varies depending on conditions such as compounds, administration routes, and symptoms or ages of patients. In the case of oral administration, about 0.01 to 1000 mg, preferably about 0.1 to 500 mg, per day may be administered to an adult in a single dose or in several divided doses.

The present compound may be orally or parenterally administered directly or in a suitable dosage form after formulation. Such a dosage form includes, for example, tablets, capsules, powders, granules, liquids, suspensions, injections, patches, and cataplasms; but is not limited thereto. Formulations are prepared with pharmaceutically acceptable excipients according to known methods. Such excipients can be selected from vehicles, disintegrants, binders, fluidizers, lubricants, coating agents, solubilizers, solubilizing agents, thickening agents, dispersants, stabilizing agents, sweetening agents, and fragrances depending on the purpose. Such excipients include, for example, lactose, mannitol, crystalline cellulose, low-substituted hydroxypropylcellulose, corn starch, partly pregelatinized starch, carmellose calcium, croscarmellose sodium, hydroxypropylcellulose, hydroxypropylmethylcellulose, polyvinyl alcohol, magnesium stearate, sodium stearyl fumarate, polyethylene glycol, propylene glycol, titanium oxide, and talc.

The present compound may be used in combination with one or more antipsychotic drugs to treat one or more psychiatric diseases or neurodegenerative diseases described herein. Such antipsychotic drugs include, for example, therapeutic agents of major depressive disorder, depressive disorders (such as major depression, treatment-resistant depression, and chronic depression), bipolar and related disorders (such as bipolar depression), anxiety disorders (such as generalized anxiety disorder, panic disorder, social anxiety disorder, and specific phobia), posttraumatic stress disorder, obsessive-compulsive disorder, acute stress disorder, schizophrenia, autism spectrum disorder, Alzheimer's disease, cognitive dysfunction, dementia, drug dependence, obesity, seizure, tremor, pain, and sleep disorder. The administration interval of the present compound and these therapeutic agents is not limited; i.e., these may be administered to a subject at the same time or with a suitable interval. Alternatively, the present compound and any of these therapeutic agents may be formulated into a single combination drug. The dose of these therapeutic agents can be suitably determined on the basis of clinically-used doses thereof. The combination ratio of the present compound and any of these therapeutic agents can be suitably determined on the basis of the condition such as subjects to be administered, administration routes, target diseases, symptoms, and combinations thereof.

When the present compound is used for an active pharmaceutical ingredient, it is not intended to be used only for human, but it can be used for other animals, such as cats, dogs, cows, chickens, and fishes, besides human.

The present invention is explained in more detail as below by referring to Reference examples, Examples, and Tests; however, the technical scope of the present invention is not limited thereto. The compound names used in Reference examples and Examples hereinafter are not necessarily based on IUPAC nomenclature system. In order to simplify descriptions, abbreviations may be used.

EXAMPLES

Compounds were identified by proton nuclear magnetic resonance spectroscopy ($^1$H-NMR), LC-MS, and the like.

For the nuclear magnetic resonance spectroscopy, tetramethylsilane was used as an internal standard.

Silica gel columns and amino columns manufactured by Yamazen Corporation were used for column chromatography and amino chromatography in Reference examples and Examples. In purification by TLC, Silica gel 60F254 (Merck) was used for TLC (silica gel plate), and TLC plate NH (Fuji Silysia) was used for TLC (NH silica gel plate).

The following apparatuses were used in Reference examples and Examples. Various data were obtained with the following apparatuses in Reference examples and Examples.

Microwave reactor: Biotage AB Initiator
NMR spectra: [$^1$H-NMR] 400 MHz: JEOL JNM-AL series AL 400 LC-MS spectra: Waters ACQUITY™ UltraPerformance LC
High-performance liquid chromatograph (HPLC): Shimazu LC-20 Powder X-ray diffraction: Spectris Power X-ray diffraction system Empyrian
CHN Elemental analyzer: FlasH 2000 manufactured by Thermo Fisher Scientific Inc.
Ion analyzer: ICS-5000+ manufactured by Thermo Fisher Scientific Inc.
Compounds in Reference examples and Examples were named by ACD/Name (ACD/Labs 12.0, Advanced Chemistry Development Inc.).

LC-MS data in Reference examples and Examples were measured under the following conditions. Observed values in mass spectroscopy [MS(m/z)] are shown in [M+H]$^+$.
Measurement conditions
Column: ACQUITY UPLC BEH C18 1.7 μm 2.1×30 mm column
Solvent: Solution A: 0.05% HCOOH/H$_2$O, Solution B: CH$_3$CN
Gradient conditions:
0.0-1.3 min; A/B=90/10 to 5/95 (linear gradient)
1.3-1.5 min; A/B=90/10
Flow rate: 0.80 mL/min
UV: 220 nm, 254 nm
Column temperature: 40° C.

Data of high-performance liquid chromatograph (HPLC) in Reference examples and Examples were measured under the following conditions. Retention times are shown in Rt (min)
Column: Phenomenex Kinetex 2.6 μm C18 (75×3.0 mm)
Solvent: Solution A: 0.035% TFA/H$_2$O, Solution B: 0.035% TFA/CH$_3$CN
Gradient Conditions:
0.0 min; A/B=99/1
0.0-5.70 min; A/B=99/1 to 1/99
(Linear Gradient)
5.70-8.00 min; A/B=1/99
Flow rate: 0.90 mL/min
UV: 220 nm, 254 nm
Column temperature: 40° C.

Powder X-ray diffraction measurement in Reference examples and Examples were conducted under the following conditions.
X-ray tube: CuKα (wavelength: 1.54 angstrom)
Tube voltage: 45 kV
Tube current: 40 mA
Measurement range: 4 to 40 degrees (2θ)
Step range: 0.013 degree
Integration time: 100 seconds/step
Diffraction patterns (XRD spectra) obtained are shown in FIGS. 1 to 3.

Crystalline forms may be determined on the basis of characteristic diffraction peaks of each crystal shown in the diffraction diagrams of FIGS. 1 to 3.

Major and characteristic diffraction peaks determined in the diffraction patterns of FIGS. 1 to 3 are shown as below. Diffraction peak values of diffraction angles 2θ (°) in the following Examples may comprise a certain amount of measurement deviations depending on measurement apparatuses or measurement conditions. Specifically, such measurement deviations may be within the range of ±0.2, preferably ±0.1.

CHN elemental analyses in Reference examples and Examples were conducted under the following conditions.
Combustion furnace temperature: 1000° C.
Reducing furnace temperature: 700° C.
Temperature in constant temperature bath: 55° C.
Analysis time: 600 seconds
Flow rate of helium gas: 110 mL/min
Injection rate of oxygen gas: 75 mL/min Ion analyses in Reference examples and Examples were conducted under the following conditions.
Cartridge for pretreatment of samples: TOYO IC-SP M
Detector: Conductivity detector
Guard column: IonPac AG11-HC (0.4 mm i.d.×50 mm, Thermo Fisher Scientific)
Column: IonPac AS11-HC (0.4 mm i.d.×250 mm, Thermo Fisher Scientific)
Suppressor: ACES-300 (4 mm i.d., Thermo Fisher Scientific)
Column oven: 30° C.
Flow rate: 0.015 mL/min
Injection rate: 0.4 μL
Analysis time: 18 min
Eluent: potassium hydroxide solution prepared with Eluent generator EGC KOH (capillary)
Gradient conditions (eluent concentrations)
0-5 min; 10 mM
5-10 min; 10-30 mM (Linear gradient)
10-18 min; 30 mM The following abbreviations may be used in Reference examples and Examples.
CDCl$_3$: deuterochloroform
CD$_3$OD: deuteromethanol
DMSO-d$_6$: deuterodimethylsulfoxide
s: singlet
d: doublet
t: triplet
q: quartet
m: multiplet
br: broad
dd: double doublet
td: triple doublet
J: coupling constant
Hz: Hertz
min: minute
atm: atmosphere
HATU: O-(7-aza-1H-benzotriazol-1-yl)-N,N,N',N'-tetramethyluronium hexafluorophosphate
HPLC: High-performance liquid chromatograph
THF: tetrahydrofuran
DME: 1,2-dimethoxyethane
TFA: trifluoroacetic acid
DMF: N,N-dimethylformamide
HBTU: O-(benzotriazol-1-yl)-N,N,N',N'-tetramethyluronium hexafluorophosphate
X-phos: 2-dicyclohexylphosphino-2',4',6'-triisopropylbiphenyl S-phos: 2-dicyclohexylphosphino-2',6'-dimethoxybiphenyl
N.D.: Not Detected
RLU: Relative Light Unit Reference Example 1: ethyl 1-{(2S)-1-[(tert-butoxycarbonyl)amino]propan-2-yl}-1H-pyrazolo-5-carboxylate

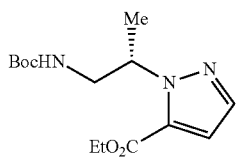 [SMILES: CCOC(=O)c1ccnn1[C@@H](C)CNC(=O)OC(C)(C)C]

To a solution of tert-butyl N-[(2R)-2-hydroxypropyl]carbamate (18.3 g) in THF (130 mL) were added ethyl 1H-pyrazole-3-carboxylate (16.1 g) and triphenylphosphine (30.2 g) at room temperature, and then thereto was added dropwise diisopropyl azodicarboxylate (60.6 mL, 1.9 mol/L toluene solution) over 30 minutes. The mixture was stirred further at room temperature for 2 hours, and then thereto was added water (130 mL). The mixture was stirred for 30 minutes. The mixture was extracted with ethyl acetate twice, and the separated organic layers were combined and dried over anhydrous sodium sulfate, filtered, and concentrated under reduced pressure. To the resulted residue was added hexane:diethyl ether (1:1, 200 mL), and the resulted solid was filtered off. The filtrate was concentrated under reduced pressure to give a crude product. The resulted crude product was purified by silica gel column chromatography (hexane/ethyl acetate) to give the titled compound (26.5 g).
$^{1}$H-NMR (400 MHz, CDCl$_3$) δ: 7.52 (1H, d, J=1.8 Hz), 6.83 (1H, d, J=1.8 Hz), 5.58-5.48 (1H, m), 4.88 (1H, s), 4.34 (2H, q, J=7.1 Hz), 3.66-3.49 (2H, m), 1.47-1.33 (15H, m)

Reference Example 2: (7S)-7-methyl-6,7-dihydropyrazolo[1,5-a]pyrazin-4(5H)-one

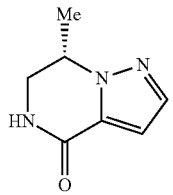

To a solution of the compound of Reference example 1 (26.5 g) in toluene (90 mL) was added TFA (27.8 mL) at ice bath temperature, and the mixture was stirred at room temperature overnight. The reaction mixture was concentrated under reduced pressure, and the residue was dissolved in DMF (150 mL). Thereto was added dropwise triethylamine (37.9 mL) at room temperature. The reaction mixture was heated to reflux for 7 hours, and then thereto was added water (300 mL). The mixture was stirred for additional 10 minutes. The mixture was extracted with chloroform:methanol (4:1) 14 times, and then the separated organic layers were combined and dried under anhydrous sodium sulfate, filtered, and concentrated under reduced pressure. To the resulted residue was added diethyl ether (100 mL), and the mixture was stirred. The resulted solid was collected by filtration (6.51 g). The filtrate was concentrated under reduced pressure, and to the resulted residue was added diethyl ether (100 mL). The mixture was stirred, and the resulted solid was collected by filtration (2.51 g). The resulted solids were combined to give the titled compound (8.66 g).
$^{1}$H-NMR (400 MHz, CDCl$_3$) δ: 7.57 (1H, d, J=2.4 Hz), 6.88 (1H, d, J=2.4 Hz), 6.88-6.82 (1H, m), 4.60-4.50 (1H, m), 3.80 (1H, ddd, J=7.6, 4.8, 3.6 Hz), 3.49 (1H, ddd, J=10.4, 7.6, 2.8 Hz), 1.62 (3H, d, J=6.1 Hz).

Reference Example 3: (7S)-7-methyl-5-[4-(trifluoromethyl)phenyl]-6,7-dihydropyrazolo[1,5-a]pyrazin-4 (5H)-one

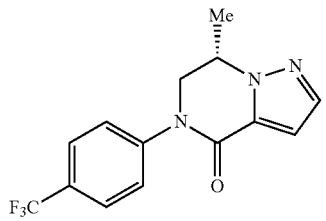 [SMILES: C[C@H]1CN(c2ccc(C(F)(F)F)cc2)C(=O)c2ccnn21]

To a suspension of 1-bromo-4-(trifluoromethyl)benzene (60.6 g), the compound of Reference example 2 (33.92 g), and potassium carbonate (62 g) in toluene (746 mL) were added N,N'-dimethylethylenediamine (11.87 g) and copper iodide (8.55 g), and the mixture was heated to reflux for 6 hours. The reaction solution was let cool to room temperature, and then thereto were added 14% ammonia water (750 mL) and ethyl acetate (750 mL). The mixture was stirred at room temperature for 30 minutes. The mixture was separated into layers, and the organic layer was washed sequentially with 14% ammonia water (750 mL) and brine (400 mL), and then dried over anhydrous sodium sulfate, filtered, and concentrated under reduced pressure. To the residue were added isopropanol (760 mL), activated carbon (7.6 g), and silica gel (24 g), and the mixture was stirred at room temperature for 1 hour. The mixture was filtered through Celite and washed with ethyl acetate (200 mL) three times, and then the filtrate was concentrated under reduced pressure to give the titled compound (71.8 g).
$^{1}$H-NMR (400 MHz, CDCl$_3$) δ: 7.68 (2H, d, J=8.5 Hz), 7.60 (1H, d, J=1.8 Hz), 7.49 (2H, d, J=8.5 Hz), 6.97 (1H, d, J=1.8 Hz), 4.75-4.67 (1H, m), 4.21 (1H, dd, J=12.5, 4.3 Hz), 3.95 (1H, dd, J=12.5, 7.6 Hz), 1.69 (3H, d, J=6.7 Hz).

Reference Example 4: (7S)-3-iodo-7-methyl-5-[4-(trifluoromethyl)phenyl]-6,7-dihydropyrazolo[1,5-a]pyrazin-4 (5H)-one

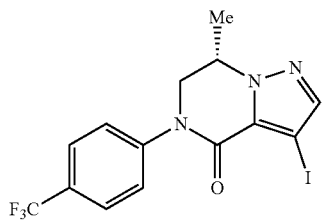 [SMILES: C[C@H]1CN(c2ccc(C(F)(F)F)cc2)C(=O)c2c(I)cnn21]

A suspension of the compound of Reference example 3 (104.9 g) and 1,3-diiodo-5,5-dimethylhydantoin (88 g) in acetic acid (662 mL) was stirred at 100° C. for 1 hour. The reaction suspension was let cool to room temperature, and then thereto was added dropwise water (330 mL). The mixture was stirred for 30 minutes. To the reaction mixture were added dropwise hexane (200 mL) and water (990 mL), and the mixture was stirred for 30 minutes. The resulted solid was collected by filtration and washed with hexane (150 mL) three times to give a crude product (146 g). To the resulted crude product was added isopropanol (438 mL). The mixture was stirred at 75° C., and then let gradually cool to 55° C. To the mixture was added dropwise water (657 mL). The mixture was stirred for 1 hour, and then cooled to 15° C. over 3 hours. The resulted solid was collected by filtration and washed with isopropanol:water (1:2) twice, and dried under reduced pressure to give the titled compound (133 g).

$^1$H-NMR (400 MHz, CDCl$_3$) δ: 7.68-7.66 (3H, m), 7.49 (2H, d, J=8.5 Hz), 4.75-4.71 (1H, m), 4.22 (1H, dd, J=12.5, 4.3 Hz), 3.95 (1H, dd, J=12.5, 7.6 Hz), 1.67 (3H, d, J=6.1 Hz).

Reference Example 5: (7S)-3-iodo-7-methyl-6,7-dihydropyrazolo[1,5-a]pyrazin-4(5H)-one

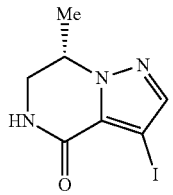

To a solution of the compound of Reference example 2 (5.15 g) in acetic acid (85 mL) was added 1,3-diiodo-5,5-dimethylhydantoin (10.35 g). The reaction solution was stirred at 100° C. for 4 hours, and then let cool to room temperature. To the solution was added saturated aqueous sodium thiosulfate solution. The mixture was extracted with chloroform:ethanol (4:1) twice, and then the organic layers were dried over anhydrous sodium sulfate, filtered, and concentrated under reduced pressure to give the titled compound (11.06 g).

$^1$H-NMR (400 MHz, DMSO-d$_6$) δ: 7.93 (1H, s), 4.54-4.47 (1H, m), 3.66-3.61 (1H, m), 3.33-3.29 (1H, m), 1.42 (3H, d, J=6.1 Hz).

LC-MS, m/z; 278[M+H]$^+$ retention time; 0.567 min

Reference Example 6: imidazo[1,2-a]pyridin-6-ylboronic acid

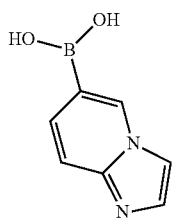 [SMILES: OB(O)c1ccc2nccn2c1]

A mixture of bis(pinacolato)diboron (3.74 g), 6-bromo-imidazo[1,2-a]pyridine (2.23 g), 1,1'-bis(diphenylphosphino)ferrocene palladium (II) chloride (0.924 g), and potassium acetate (2.78 g) in toluene (16 mL) was heated to reflux with stirring for 2 hours. The reaction mixture was let cool to room temperature, and then filtered through Celite. The filtrate was concentrated under reduced pressure to give a crude product of the titled compound.

LC-MS, m/z; 163[M+H]$^+$ retention time; 0.243 min

Reference Example 7: (7S)-3-(imidazo[1,2-a]pyridin-6-yl)-7-methyl-6,7-dihydropyrazolo[1,5-a]pyrazin-4(5H)-one

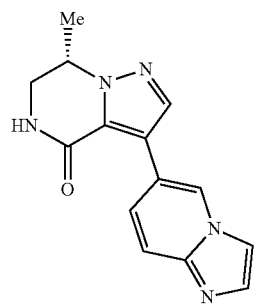 [SMILES: C[C@H]1CNC(=O)c2c(-c3ccc4nccn4c3)cnn21]

A mixture of the compound of Reference example 5 (2.41 g), the compound of Reference example 6 (1.83 g), palladium acetate (195 mg), X-phos (830 mg), and potassium carbonate (2.41 g) in 1,2-dimethoxyethane (16 mL)/water (8 mL) was heated to reflux with stirring for 4 hours. The reaction mixture was let cool to room temperature, and then diluted with ethyl acetate, and filtered through Celite. To the filtrate was added water, and the mixture was separated into layers. The organic layer was washed with brine, and then dried over anhydrous sodium sulfate, filtered, and concentrated under reduced pressure. The resulted residue was purified by amino silica gel column chromatography (chloroform/methanol) to give the titled compound (693.9 mg) LC-MS, m/z; 268[M+H]$^+$ retention time; 0.376 min Reference Example 8: {(7S)-7-methyl-4-oxo-5-[4-(trifluoromethyl)phenyl]-4,5,6,7-tetrahydropyrazolo[1,5-a]pyrazin-3-yl}boronic acid

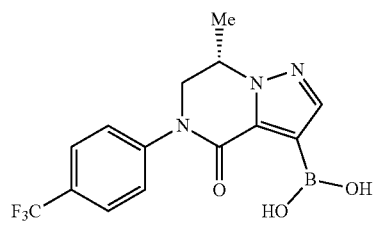 [SMILES: C[C@H]1CN(c2ccc(C(F)(F)F)cc2)C(=O)c2c(B(O)O)cnn21]

To a solution of the compound of Reference example 4 (10.00 g) and 2-isopropoxy-4,4,5,5-tetramethyl-1,3,2-dioxaborolane (9.60 mL) in THF (100 mL) was added dropwise isopropylmagnesium chloride-lithium chloride complex (42.7 mL) at −25° C. The reaction mixture was stirred at −25° C. for 30 minutes, and then thereto was added saturated aqueous ammonium chloride solution. The mixture was extracted with ethyl acetate. The organic layer was washed with brine, and then dried over anhydrous sodium sulfate, filtered, and concentrated under reduced pressure. The resulted residue was purified by silica gel column chromatography (hexane/ethyl acetate) to give the titled compound (9.12 g) LC-MS, m/z; 340[M+H]+ retention time; 0.865 min Reference Example 9: (2R)-1-{[4-(trifluoromethyl)phenyl]amino}propan-2-ol

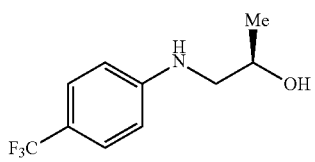

To a mixture of 1-iodo-4-(trifluoromethyl)benzene (168 g), (R)-1-aminopropan-2-ol (116 g), and methanol (168 mL) was added potassium hydroxide (69.3 g) at 20° C. with stirring, and the mixture was stirred. Exotherm was cooled to 20° C., and to the mixture was added copper (I) chloride (6.11 g).

The mixture was warmed to 30° C. and stirred for 3 hours, and then stirred at 20° C. for 15 hours. Methanol was removed under reduced pressure, and to the residue were added water (880 mL), 28% ammonia water (220 mL), and toluene (880 mL). The mixture was stirred for 30 minutes, and then separated into layers. The toluene layer was washed with water (880 mL), and then concentrated under reduced pressure to give the titled compound (130 g).

$^1$H-NMR (400 MHz, CDCl$_3$) δ: 7.39 (d, 2H, J=8.2 Hz), 6.66 (d, 2H, J=8.2 Hz), 4.09-4.01 (m, 1H), 3.25 (dd, 1H, J=3.0, 12.8 Hz), 3.03 (dd, 1H, J=7.9, 12.8 Hz), 1.27 (d, 3H, J=6.7 Hz)

Reference Example 10: methyl 4-bromo-1-{(2S)-1-[4-(trifluoromethyl)anilino]propan-2-yl}-1H-pyrazole-5-carboxylate

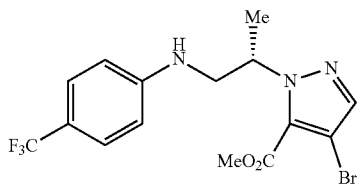 [SMILES: COC(=O)c1c(Br)cnn1[C@@H](C)CNc1ccc(C(F)(F)F)cc1]

To a mixture of the compound of Reference example 9 (3.03 g), diisopropyl azodicarboxylate (2.93 g), methyl 4-bromo-1H-pyrazole-5-carboxylate (2.83 g), and tetrahydrofuran (18 mL) was added triphenylphosphine (3.81 g) with stirring at ice temperature, and the mixture was stirred for 1.5 hours at ice temperature and for 22 hours at 20° C. The reaction solution was concentrated and purified by column chromatography (silica gel, hexane/ethyl acetate=8/1 to 5/1) to give the titled compound (2.38 g).

$^1$H-NMR (400 MHz, CDCl$_3$) δ: 7.55 (s, 1H), 7.35 (d, 2H, J=8.5 Hz), 6.52 (d, 2H, J=8.5 Hz), 5.57-5.52 (m, 1H), 4.26 (br, 1H), 3.78 (s, 3H), 3.67-3.59 (m, 1H), 3.50-3.44 (m, 1H), 1.53 (d, 3H, J=6.7 Hz)

Reference Example 11: 4-bromo-1-{(2S)-1-[4-(trifluoromethyl)anilino]propan-2-yl}-1H-pyrazole-5-carboxylic acid

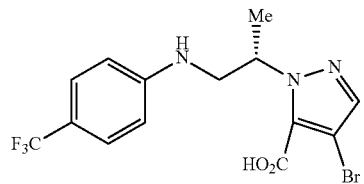 [SMILES: C[C@@H](CNc1ccc(C(F)(F)F)cc1)n1ncc(Br)c1C(=O)O]

To a mixture of the compound of Reference example 10 (406 mg) and methanol (2 mL) was added 1 mol/L aqueous sodium hydroxide solution (1.5 mL), and the mixture was stirred at room temperature for 24 hours. The reaction solution was cooled with ice, acidified with 5% aqueous potassium hydrogensulfate solution, and extracted with ethyl acetate. The organic layer was dried over anhydrous sodium sulfate, and then concentrated under reduced pressure to give the titled compound (392 mg).

$^1$H-NMR (400 MHz, DMSO-d$_6$) δ: 13.84 (brs, 1H), 7.75 (s, 1H), 7.32 (d, 2H, J=8.9 Hz), 6.64 (d, 2H, J=8.9 Hz), 6.44 (br, 1H), 5.52-5.44 (m, 1H), 3.53-3.47 (m, 1H), 3.40-3.35 (m, 1H), 1.43 (d, 3H, J=6.7 Hz).

Reference Example 12: (7S)-3-bromo-7-methyl-5-[4-(trifluoromethyl)phenyl]-6,7-dihydropyrazolo[1,5-a]pyrazin-4(5H)-one

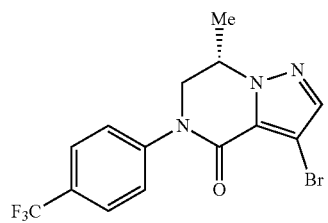

Synthesis-1: To a mixture of the compound of Reference example 11 (392 mg) and toluene (3 mL) was added p-toluenesulfonic acid monohydrate (16 mg), and the mixture was stirred at 100° C. for 12 hours. The reaction solution was cooled to 20° C., and thereto was added saturated aqueous sodium hydrogen carbonate solution. The mixture was extracted with toluene. The organic layer was dried over sodium sulfate, and then concentrated under reduced pressure to give the titled compound (356 mg).

Synthesis-2: To a mixture of the compound of Reference example 10 (406 mg) and toluene (3 mL) was added p-toluenesulfonic acid monohydrate (16 mg), and the mixture was stirred at 100° C. for 8 hours. The area percentage of liquid chromatography showed the ratio of product/starting material=15/82.

$^1$H-NMR (400 MHz, CDCl$_3$) δ: 7.67 (d, 2H, J=8.5 Hz), 7.59 (s, 1H), 7.49 (d, 2H, J=8.5 Hz), 4.73-4.65 (m, 1H), 4.20 (dd, 1H, J=4.3, 12.8 Hz), 3.95 (dd, 1H, J=7.3, 12.8 Hz), 1.67 (d, 3H, J=6.7 Hz).

Reference Example 13: (7S)-3-(3-iodoimidazo[1,2-a]pyridin-6-yl)-7-methyl-5-[4-(trifluoromethyl)phenyl]-6,7-dihydropyrazolo[1,5-a]pyrazin-4(5H)-one

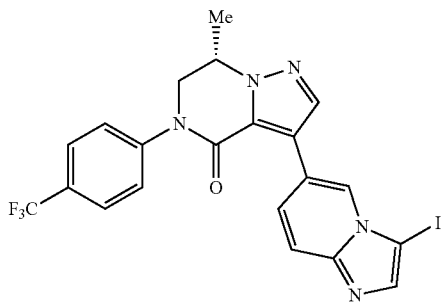 [SMILES: C[C@H]1CN(c2ccc(C(F)(F)F)cc2)C(=O)c2c(-c3ccc4ncc(I)n4c3)cnn21]

A solution of the compound of Example 1 (386 mg) and 1,3-diiodo-5,5-dimethylhydantoin (178 mg) in acetic acid (4 mL) was stirred at room temperature for 5 hours. To the reaction solution was added saturated aqueous sodium thiosulfate solution, and the mixture was extracted with ethyl acetate. The organic layer was washed with saturated sodium hydrogen carbonate solution and brine, and then dried over anhydrous sodium sulfate, filtered, and concentrated under reduced pressure. The resulted residue was purified by silica gel column chromatography (hexane/ethyl acetate) to give the titled compound (403 mg).

$^1$H-NMR (400 MHz, DMSO-D$_6$) δ: 9.02 (1H, d, J=1.2 Hz), 8.14 (1H, s), 7.82 (2H, d, J=8.5 Hz), 7.70-7.59 (5H, m), 4.85-4.83 (1H, m), 4.38 (1H, dd, J=12.8, 4.3 Hz), 4.12-4.07 (1H, m), 1.60 (3H, d, J=6.7 Hz).

Reference Example 14: (7S)-3-(3-ethenylimidazo[1,2-a]pyridin-6-yl)-7-methyl-5-[4-(trifluoromethyl)phenyl]-6,7-dihydropyrazolo[1,5-a]pyrazin-4(5H)-one

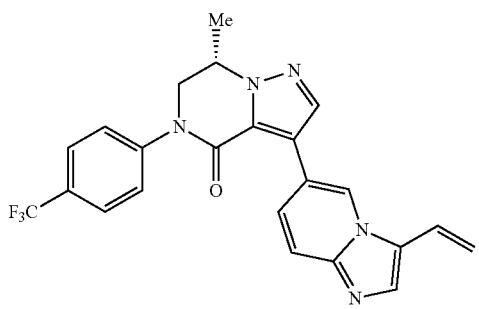 [SMILES: C=Cc1cnc2ccc(-c3cnn4c3C(=O)N(c3ccc(C(F)(F)F)cc3)C[C@@H]4C)cn12]

A mixture of the compound of Reference example 13 (219 mg), 4,4,5,5-tetramethyl-2-vinyl-1,3,2-dioxaborolane (0.14 mL), tetrakis(triphenylphosphine)palladium (0) (47.1 mg), and potassium carbonate (130 mg) in 1,2-dimethoxyethane (2 mL) and water (1 mL) was heated to reflux with stirring for 4 hours. The reaction mixture was let cool to room temperature, and then diluted with ethyl acetate and filtered through Celite. To the filtrate was added saturated aqueous sodium hydrogen carbonate solution, and the mixture was separated into layers. The organic layer was washed with brine, and then dried over anhydrous sodium sulfate, filtered, and concentrated under reduced pressure. The resulted residue was purified by amino silica gel column chromatography (hexane/ethyl acetate) to give the titled compound (87.8 mg).

LC-MS, m/z; 438[M+H]$^+$ retention time; 0.805 min

Reference Example 15: (7S)-7-methyl-3-{3-[(1Z)-prop-1-en-1-yl]imidazo[1,2-a]pyridin-6-yl}-5-[4-(trifluoromethyl)phenyl]-6,7-dihydropyrazolo[1,5-a]pyrazin-4(5H)-one

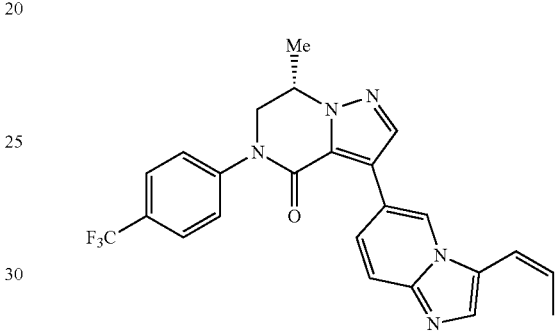

The compound of Reference example 13 (210 mg) was treated with cis-propenylboronic acid (67.1 mg) in a similar manner to Reference example 14 to give the titled compound (114.1 mg).

LC-MS, m/z; 452[M+H]$^+$ retention time; 0.805 min

Reference Example 16: (7S)-5-(4-fluoro-3-methylphenyl)-7-methyl-6,7-dihydropyrazolo[1,5-a]pyrazin-4(5H)-one

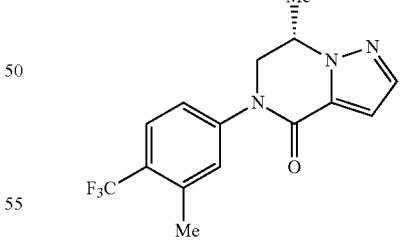

The compound of Reference example 2 (1.05 g) was treated with 4-bromo-1-fluoro-2-methylbenzene (1.58 g) in a similar manner to Reference example 3 to give the titled compound (1.80 g).

$^1$H-NMR (400 MHz, CDCl$_3$) δ: 7.57 (1H, d, J=1.8 Hz), 7.16 (1H, dd, J=6.7, 3.1 Hz), 7.11-7.07 (1H, m), 7.04-7.02 (1H, m), 6.92 (1H, d, J=1.8 Hz), 4.70-4.62 (1H, m), 4.12 (1H, dd, J=12.8, 4.3 Hz), 3.84 (1H, dd, J=12.8, 7.3 Hz), 2.27 (3H, d, J=1.8 Hz), 1.66 (3H, d, J=6.7 Hz).

Reference Example 17: (7S)-5-(4-fluoro-3-methylphenyl)-3-iodo-7-methyl-6,7-dihydropyrazolo[1,5-a]pyrazin-4(5H)-one

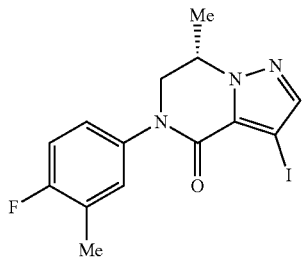 [SMILES: Cc1cc(N2C[C@H](C)n3ncc(I)c3C2=O)ccc1F]

The compound of Reference example 16 (1.70 g) was treated in a similar manner to Reference example 4 to give the titled compound (2.00 g).
¹H-NMR (400 MHz, CDCl₃) δ: 7.62 (1H, s), 7.18 (1H, dd, J=6.7, 2.4 Hz), 7.10-7.06 (1H, m), 7.03-7.01 (1H, m), 4.72-4.64 (1H, m), 4.13 (1H, dd, J=12.8, 4.3 Hz), 3.85 (1H, dd, J=12.8, 7.3 Hz), 2.27 (3H, d, J=1.8 Hz), 1.64 (3H, d, J=6.1 Hz).

Reference Example 18: (7S)-5-(4-fluoro-3-methylphenyl)-3-(3-iodoimidazo[1,2-a]pyridin-6-yl)-7-methyl-6,7-dihydropyrazolo[1,5-a]pyrazin-4(5H)-one

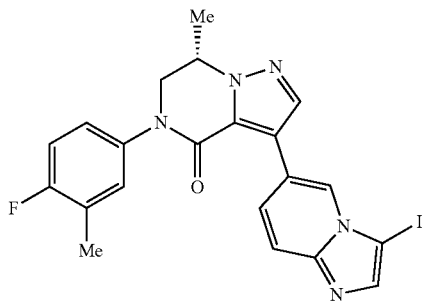 [SMILES: Cc1cc(N2C[C@H](C)n3ncc(-c4ccc5ncc(I)n5c4)c3C2=O)ccc1F]

The compound of Example 17 (40.0 mg) was treated in a similar manner to Reference example 13 to give the titled compound (39.4 mg).
¹H-NMR (400 MHz, CDCl₃) δ: 8.59-8.59 (1H, m), 7.77 (1H, s), 7.65 (1H, s), 7.54-7.53 (2H, m), 7.16 (1H, dd, J=6.9, 2.7 Hz), 7.12-7.08 (1H, m), 7.04-6.99 (1H, m), 4.77-4.74 (1H, m), 4.20 (1H, dd, J=12.8, 4.1 Hz), 3.90 (1H, dd, J=12.8, 7.1 Hz), 2.26 (3H, d, J=1.8 Hz), 1.73 (3H, d, J=6.4 Hz).

Reference Example 19

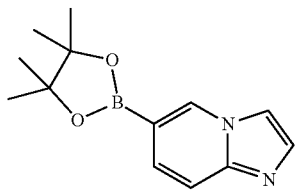 [SMILES: CC1(C)OB(c2ccc3nccn3c2)OC1(C)C]

A mixture of 6-bromoimidazo[1,2-a]pyridine (151.72 g), bis(pinacolato)diboron (235 g), 1,1'-bis(diphenylphosphino)ferrocene palladium (II) chloride-dichloromethane adduct (62.9 g), and potassium acetate (189 g) in 1,2-dimethoxyethane (1.59 L) was heated to reflux with stirring for 4.5 hours. The reaction mixture was let cool to room temperature, and then the precipitated solid was collected by filtration and washed with 1,2-dimethoxyethane (200 ml). To the resulted solid were added water (500 ml) and hexane (500 ml), and the mixture was suspended with stirring at room temperature for 30 minutes. The resulted solid was collected by filtration and washed with 1,2-dimethoxyethane (400 ml) three times to give the titled compound (145.1 g).
¹H-NMR (400 MHz, CDCl₃) δ: 8.55 (1H, t, J=1.2 Hz), 7.62-7.56 (3H, m), 7.44 (1H, dd, J=9.2, 1.2 Hz), 1.35 (13H, s).

Example 1: (7S)-3-(imidazo[1,2-a]pyridin-6-yl)-7-methyl-5-[4-(trifluoromethyl)phenyl]-6,7-dihydropyrazolo[1,5-a]pyrazin-4 (5H)-one

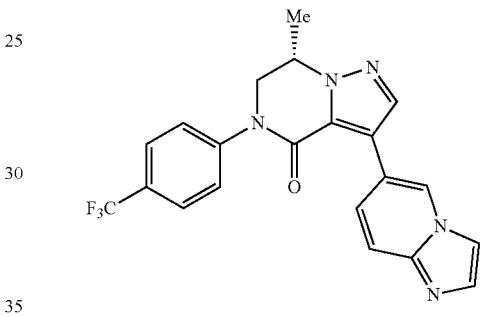

Synthesis-1: A mixture of the compound of Reference example 4 (1.15 g), the compound of Reference example 6 (661 mg), palladium acetate (61.1 mg), X-phos (259 mg), and potassium carbonate (752 mg) in 1,2-dimethoxyethane (6 mL)/water (3 mL) was heated to reflux with stirring for 3 hours. The reaction mixture was let cool to room temperature, and then diluted with ethyl acetate and filtered through Celite. To the filtrate was added water, and the mixture was separated into layers. The organic layer was washed with brine, and then dried over anhydrous sodium sulfate, filtered, and concentrated under reduced pressure. The resulted residue was purified by amino silica gel column chromatography (hexane/ethyl acetate) to give the titled compound (551.5 mg).

Synthesis-2: A mixture of the compound of Reference example 12 (177 mg), the compound of Reference example 6 (92 mg), potassium carbonate (196 mg), tetrakis(triphenylphosphine)palladium (0) (27 mg), 1,4-dioxane (1.9 mL), and water (0.47 mL) was stirred at 90° C. for 3.5 hours. The mixture was cooled to 20° C., and thereto was added brine. The mixture was extracted with ethyl acetate. The organic layer was dried over anhydrous sodium sulfate, and then concentrated under reduced pressure. The resulted residue was stirred in ethyl acetate (about 1.5 mL) at room temperature, and the resulted solid was collected by filtration. The solid was washed with ethyl acetate (about 0.5 mL) to give the titled compound (102 mg).

Synthesis-3: A mixture of the compound of Reference example 4 (116 g), the compound of Reference example 6 (67.0 g), palladium acetate (6.20 g), X-phos (26.3 g), and potassium carbonate (76 g) in 1,2-dimethoxyethane (700 mL)/water (350 mL) was heated to reflux with stirring for 3 hours. The reaction mixture was let cool to room temperature, and then thereto were added ethyl acetate (500 mL) and 2 mol/L hydrochloric acid (1000 mL). The mixture was stirred at room temperature for 30 minutes. The mixture was filtered through Celite, and the residue was washed with ethyl acetate (500 mL), and then the filtrate was separated into layers. The organic layer was washed with 2 mol/L hydrochloric acid (500 mL) twice, and the aqueous layers were combined, and adjusted to pH 9 by addition of 10 mol/L aqueous sodium hydroxide solution. The aqueous layer was extracted with chloroform (500 mL) three times, and then washed with brine, and then dried over anhydrous sodium sulfate, filtered, and concentrated under reduced pressure. To the residue (125.3 g) was added ethanol (1253 mL), and the mixture was heated to reflux with stirring for 30 minutes. To the mixture was added water (626 mL), and the mixture was heated to reflux with stirring. The mixture was let cool to room temperature, and then the resulted solid was collected by filtration and washed with ethyl acetate. To the resulted solid (44.4 g) was added ethyl acetate (666 mL), and the mixture was heated to reflux with stirring for 30 minutes. The mixture was let cool to room temperature, and then the resulted solid was collected by filtration, washed with ethyl acetate, and dried under reduced pressure to give the titled compound (39.77 g).

Synthesis-4: A mixture of the compound of Reference example 4 (28.5 g), the compound of Reference example 19 (33.5 g), palladium acetate (1.519 g), S-phos (5.56 g), and potassium carbonate (18.70 g) in 1,2-dimethoxyethane (100 mL)/water (50 mL) was heated to reflux with stirring for 3 hours. The reaction mixture was let cool to room temperature, and then diluted with chloroform (180 mL)/methanol (20 mL) and filtered through Celite, and washed with chloroform (450 mL)/methanol (50 mL). To the resulted filtrate was added aqueous sodium hydrogen carbonate solution, and the mixture was separated into layers. The organic layer was washed with brine, and then dried over anhydrous sodium sulfate, filtered, and concentrated under reduced pressure. The resulted residue was purified by silica gel column chromatography (ethyl acetate/methanol) to give a solid. The resulted solid (21.23 g) was washed with ethyl acetate (210 ml), and collected by filtration. To a solution of the resulted solid (13.65 g) in chloroform (117 mL)/methanol (13 mL) was added activated carbon (trade name "Kyoryoku Shirasagi") (6.5 g), and the mixture was stirred at room temperature for 1 hour. Then, to the mixture was added Argoregin MP-TMT (6.5 g), and the mixture was stirred at room temperature for additional 1 hour. The resulted solution was filtered through Celite and washed with chloroform (720 mL)/methanol (80 mL), and then the filtrate was concentrated under reduced pressure to give the titled compound (12.03 g).

$^1$H-NMR (400 MHz, CDCl$_3$) δ: 8.89 (1H, d, J=1.8 Hz), 7.80 (1H, s), 7.70 (2H, d, J=8.5 Hz), 7.59-7.55 (3H, m), 7.48 (2H, d, J=8.5 Hz), 7.40 (1H, dd, J=9.8, 1.8 Hz), 4.80-4.75 (1H, m), 4.27 (1H, dd, J=12.5, 4.0 Hz), 3.99 (1H, dd, J=12.5, 7.3 Hz), 1.74 (3H, d, J=6.1 Hz).

[Crystalline Form I]

Major diffraction peaks: 2θ (°)=4.5, 8.5, 8.9, 10.1, 13.4, 16.9, 18.2, 18.6, 22.7, 23.8

Characteristic diffraction peaks: 2θ (°)=4.5, 8.5, 8.9, 10.1, 13.4, 16.9

Preparation of a Hydrochloride Salt of the Compound of Example 1

To a solution of the compound of Example 1 (10.8 g) in chloroform (100 mL) was added 4 mol/L hydrochloric acid-ethyl acetate (200 mL), and the mixture was stirred at room temperature for 5 minutes. The reaction mixture was concentrated under reduced pressure, and then to the residue was added ethanol (100 mL). The mixture was heated to reflux with stirring for 30 minutes. To the mixture was added hexane (50 mL), and the mixture was heated to reflux with stirring for additional 1 hour. The mixture was let cool to room temperature, and then the resulted solid was collected by filtration, washed with ethanol/hexane (1/2), and dried under reduced pressure to give a hydrochloride salt of the compound of Example 1 (10.0 g).

$^1$H-NMR (400 MHz, DMSO-d$_6$) δ: 9.37 (1H, s), 8.39 (1H, d, J=1.8 Hz), 8.28 (1H, dd, J=9.4, 1.5 Hz), 8.20 (1H, d, J=1.8 Hz), 8.12 (1H, s), 7.98 (1H, d, J=9.1 Hz), 7.83 (2H, d, J=8.5 Hz), 7.68 (2H, d, J=8.5 Hz), 4.89-4.87 (1H, m), 4.40 (1H, dd, J=12.8, 6.4 Hz), 4.14 (1H, dd, J=12.8, 7.6 Hz), 1.61 (3H, d, J=6.1 Hz).

[Crystalline Form II]

Major diffraction peaks: 2θ (°)=5.7, 8.7, 9.5, 11.0, 11.3, 12.7, 13.6, 15.3, 15.5, 16.6, 21.5

Characteristic diffraction peaks: 2θ (°)=5.7, 8.7, 9.5, 11.0, 11.3, 15.3

Preparation of a Phosphate Salt of the Compound of Example 1

To a suspension of the compound of Example 1 (8.80 g) in ethyl acetate (150 mL) was added phosphoric acid (4.38 mL), and the mixture was heated to reflux with stirring for 1 hour. The mixture was let cool to room temperature, and then the resulted solid was collected by filtration, washed with ethyl acetate, and dried under reduced pressure to give a 2.5 phosphate salt of the compound of Example 1 (14.18 g).

$^1$H-NMR (400 MHz, DMSO-d$_6$) δ: 9.05 (1H, s), 8.02 (1H, s), 7.97 (1H, s), 7.81 (2H, d, J=8.5 Hz), 7.67 (2H, d, J=8.5 Hz), 7.62-7.58 (3H, m), 4.85-4.82 (1H, m), 4.37 (1H, dd, J=12.8, 4.3 Hz), 4.10 (1H, dd, J=12.8, 7.9 Hz), 1.59 (3H, d, J=6.1 Hz).

[Crystalline Form III]

Major diffraction peaks: 2θ (°)=6.1, 6.9, 8.9, 9.8, 12.1, 13.4, 13.7, 18.0, 18.2, 20.6

Characteristic diffraction peaks: 2θ (°)=6.1, 8.9, 9.8, 12.1, 13.4, 13.7

CHN elemental analysis: $C_{21}H_{16}F_3N_5O \cdot 2.5\, H_3PO_4$; theoretical value: C, 38.43%; H, 3.61%; N, 10.67%, measured value: C, 38.29%; H, 3.59%; N, 10.54%.

Ion analysis: phosphate ion ($PO_4^{3-}$) of $C_{21}H_{16}F_3N_5O \cdot 2.5\, H_3PO_4$; theoretical value: 36.13%, measured value: 35.94%, 35.90%.

Example 2: (7S)-3-(imidazo[1,2-a]pyrazin-6-yl)-7-methyl-5-[4-(trifluoromethyl)phenyl]-6,7-dihydropyrazolo[1,5-a]pyrazin-4 (5H)-one

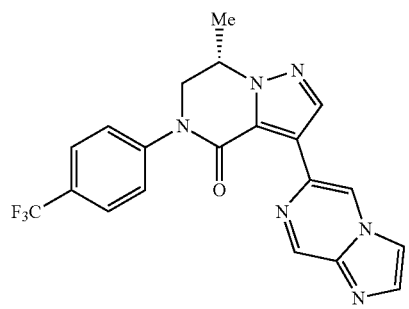 [SMILES: C[C@H]1CN(c2ccc(C(F)(F)F)cc2)C(=O)c2c(-c3cn4ccnc4cn3)cnn21]

The compound of Reference example 4 (848 mg) was treated with imidazo[1,2-a]pyrazin-6-ylboronic acid (492 mg) in a similar manner to Example 1 to give the titled compound (4 mg).

$^1$H-NMR (400 MHz, CDCl$_3$) δ: 9.71 (1H, s), 9.09 (1H, s), 8.40 (1H, s), 7.76-7.74 (3H, m), 7.66 (1H, s), 7.52 (2H, d, J=7.9 Hz), 4.82-4.80 (1H, m), 4.29 (1H, dd, J=12.2, 3.7 Hz), 3.98 (1H, dd, J=12.2, 6.7 Hz), 1.75 (3H, d, J=6.1 Hz).

Example 3: (7S)-5-(3-chloro-4-fluorophenyl)-3-(imidazo[1,2-a]pyridin-6-yl)-7-methyl-6,7-dihydro-pyrazolo[1,5-a]pyrazin-4 (5H)-one

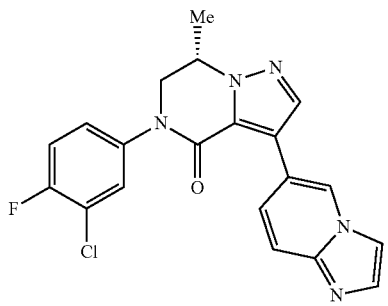 [SMILES: C[C@H]1CN(c2ccc(F)c(Cl)c2)C(=O)c2c(-c3ccc4nccn4c3)cnn21]

A mixture of the compound of Reference example 7 (300 mg), 4-bromo-2-chloro-1-fluorobenzene (0.204 mL), copper iodide (64.1 mg), N,N'-dimethylethylenediamine (0.109 mL), and potassium carbonate (310 mg) in toluene (2.5 mL) was heated to reflux with stirring for 5 hours. The reaction mixture was let cool to room temperature, and then thereto was added 28% ammonia water. The mixture was extracted with ethyl acetate. The organic layer was washed with saturated aqueous ammonium chloride solution, saturated aqueous sodium hydrogen carbonate solution, and brine, and then dried over anhydrous sodium sulfate, filtered, and concentrated under reduced pressure. The resulted residue was purified by amino silica gel column chromatography (hexane/ethyl acetate) to give the titled compound (263.3 mg).

$^1$H-NMR (400 MHz, DMSO-d$_6$) δ: 9.38 (1H, s), 8.40 (1H, d, J=1.8 Hz), 8.28 (1H, dd, J=9.5, 1.5 Hz), 8.19 (1H, d, J=1.8 Hz), 8.12 (1H, s), 7.98 (1H, d, J=9.2 Hz), 7.75 (1H, dd, J=6.7, 2.4 Hz), 7.55-7.46 (2H, m), 4.88-4.83 (1H, m), 4.32 (1H, dd, J=12.8, 4.3 Hz), 4.05 (1H, dd, J=12.8, 7.6 Hz), 1.60 (3H, d, J=6.1 Hz).

Examples 4 to 9

Compounds of corresponding Reference examples were treated according to the method of Example 3 to give the compounds of Examples 4 to 9 as shown in the following table.

| Example | Chemical structure | Instrumental analysis data |
|---|---|---|
| 4 | 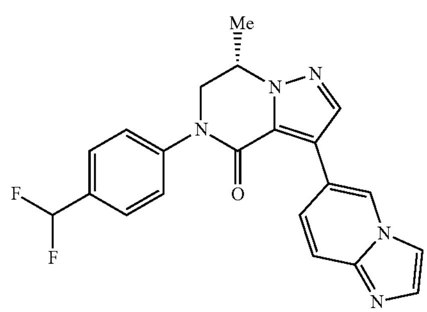 [SMILES: C[C@H]1CN(c2ccc(C(F)F)cc2)C(=O)c2c(-c3ccc4nccn4c3)cnn21] | $^1$H-NMR (400 MHz, DMSO-d$_6$) δ: 9.03 (1H, s), 8.01 (1H, s), 7.94 (1H, s), 7.65 (2H, d, J = 8.5 Hz), 7.58 (2H, d, J = 8.5 Hz), 7.55 (3H, d, J = 2.4 Hz), 7.06 (1H, t, J = 55.8 Hz), 4.84-4.80 (1H, m), 4.34 (1H, dd, J = 12.8, 4.3 Hz), 4.07 (1H, dd, J = 12.8, 7.3 Hz), 1.59 (3H, d, J = 6.7 Hz). |
| 5 | 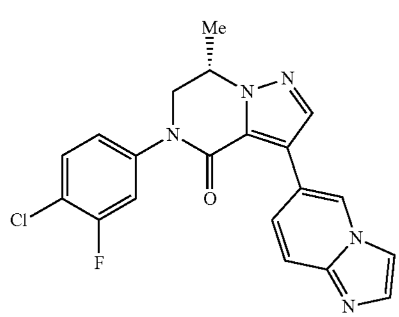 [SMILES: C[C@H]1CN(c2ccc(Cl)c(F)c2)C(=O)c2c(-c3ccc4nccn4c3)cnn21] | $^1$H-NMR (400 MHz, CDCl$_3$) δ: 8.88 (1H, d, J = 1.8 Hz), 7.79 (1H, s), 7.59-7.57 (3H, m), 7.46-7.44 (1H, m), 7.41-7.38 (1H, m), 7.21 (1H, dd, J = 9.8, 2.4 Hz), 7.11-7.08 (1H, m), 4.79-4.74 (1H, m), 4.21 (1H, dd, J = 12.8, 4.3 Hz), 3.93 (1H, dd, J = 12.8, 7.3 Hz), 1.73 (3H, d, J = 6.7 Hz). |

-continued

| Example | Chemical structure | Instrumental analysis data |
|---|---|---|
| 6 | 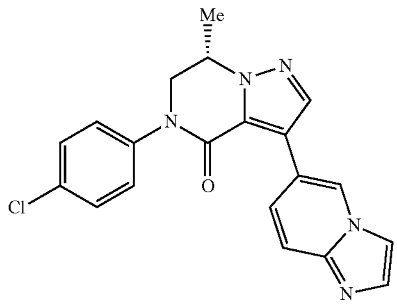 [SMILES: C[C@H]1CN(c2ccc(Cl)cc2)C(=O)c2c(-c3ccc4nccn4c3)cnn21] | ¹H-NMR (400 MHz, CDCl₃) δ: 8.93 (1H, s), 7.79 (1H, s), 7.59-7.55 (3H, m), 7.42-7.39 (3H, m), 7.28 (2H, d, J = 8.5 Hz), 4.78-4.72 (1H, m), 4.21 (1H, dd, J = 12.8, 4.3 Hz), 3.92 (1H, dd, J = 12.8, 7.3 Hz), 1.72 (3H, d, J = 6.7 Hz). |
| 7 | 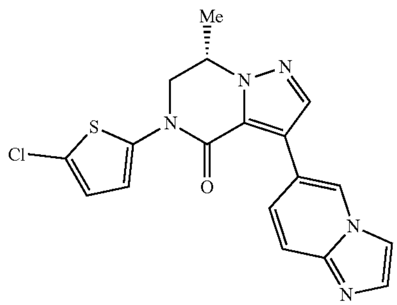 [SMILES: C[C@H]1CN(c2ccc(Cl)s2)C(=O)c2c(-c3ccc4nccn4c3)cnn21] | HPLC Rt = 4.489<br>LC-MS, m/z; 384 [M + H]⁺, Rt: 1.558 min |
| 8 | 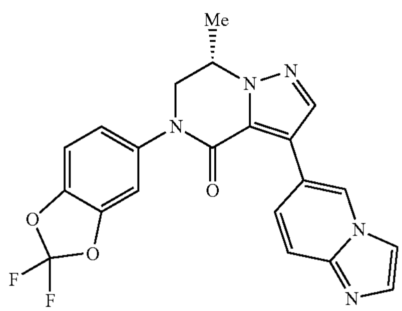 [SMILES: C[C@H]1CN(c2ccc3c(c2)OC(F)(F)O3)C(=O)c2c(-c3ccc4nccn4c3)cnn21] | ¹H-NMR (400 MHz, CDCl₃) δ: 8.93 (1H, s), 7.80 (1H, s), 7.59-7.53 (3H, m), 7.41 (1H, dd, J = 9.4, 1.5 Hz), 7.12-7.10 (2H, m), 7.02 (1H, dd, J = 8.5, 2.4 Hz), 4.78-4.76 (1H, m), 4.20 (1H, dd, J = 12.8, 4.3 Hz), 3.90 (1H, dd, J = 12.8, 7.3 Hz), 1.73 (3H, d, J = 6.1 Hz). |
| 9 | 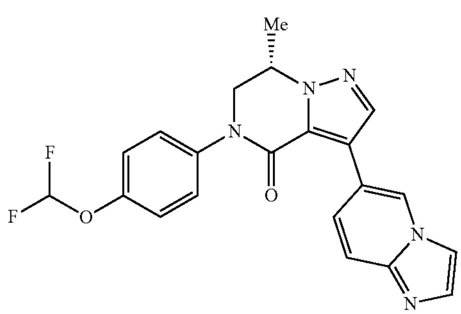 [SMILES: C[C@H]1CN(c2ccc(OC(F)F)cc2)C(=O)c2c(-c3ccc4nccn4c3)cnn21] | ¹H-NMR (400 MHz, CDCl₃) δ: 8.93 (1H, s), 7.79 (1H, s), 7.59-7.55 (3H, m), 7.43-7.33 (3H, m), 7.20 (2H, d, J = 8.5 Hz), 6.50 (1H, t, J = 73.4 Hz), 4.78-4.74 (1H, m), 4.22 (1H, dd, J = 12.8, 4.3 Hz), 3.92 (1H, dd, J = 12.8, 7.3 Hz), 1.73 (3H, d, J = 6.1 Hz). |

The following show the chemical names of the compounds of Examples 4 to 9.

Example 4: (7S)-5-[4-(difluoromethyl)phenyl]-3-(imidazo[1,2-a]pyridin-6-yl)-7-methyl-6,7-dihydropyrazolo[1,5-a]pyrazin-4(5H)-one Example 5: (7S)-5-(4-chloro-3-fluorophenyl)-3-(imidazo[1,2-a]pyridin-6-yl)-7-methyl-6,7-dihydropyrazolo[1,5-a]pyrazin-4(5H)-one Example 6: (7S)-5-(4-chlorophenyl)-3-(imidazo[1,2-a]pyridin-6-yl)-7-methyl-6,7-dihydropyrazolo[1,5-a]pyrazin-4(5H)-one Example 7: (7S)-5-(5-chlorothiophen-2-yl)-3-(imidazo[1,2-a]pyridin-6-yl)-7-methyl-6,7-dihydropyrazolo[1,5-a]pyrazin-4 (5H)-one Example 8: (7S)-5-(2,2-difluoro-1,3-benzodioxol-5-yl)-3-(imidazo[1,2-a]pyridin-6-yl)-7-methyl-6,7-dihydropyrazolo[1,5-a]pyrazin-4(5H)-one Example 9: (7S)-5-[4-(difluoromethoxy)phenyl]-3-(imidazo[1,2-a]pyridin-6-yl)-7-methyl-6,7-dihydropyrazolo[1,5-a]pyrazin-4(5H)-one Example 10: (7S)-3-(2-aminoimidazo[1,2-a]pyridin-6-yl)-7-methyl-5-[4-(trifluoromethyl)phenyl]-6,7-dihydropyrazolo[1,5-a]pyrazin-4 (5H)-one

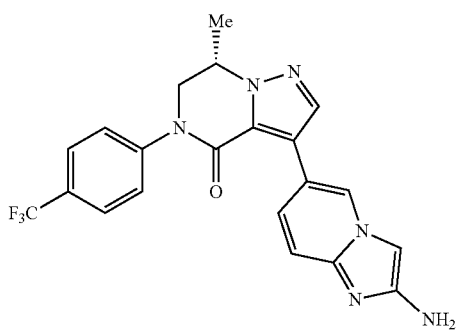 [SMILES: C[C@H]1CN(c2ccc(C(F)(F)F)cc2)C(=O)c2c(-c3ccc4nc(N)cn4c3)cnn21]

A mixture of 6-bromoimidazo[1,2-a]pyridin-2-amine (299 mg), the compound of Reference example 8 (318.9 mg), palladium acetate (21.1 mg), X-phos (90.0 mg), and potassium carbonate (260 mg) in DMF (2 mL) was stirred at 105° C. for 6 hours. The reaction mixture was let cool to room temperature, and then diluted with ethyl acetate and filtered through Celite. To the filtrate was added water, and the mixture was separated into layers. The organic layer was washed with water twice and brine, and then dried over anhydrous sodium sulfate, filtered, and concentrated under reduced pressure. The resulted residue was purified by amino silica gel column chromatography (hexane/ethyl acetate) to give the titled compound (5.10 mg).

LC-MS, m/z; 427[M+H]$^+$ retention time; 0.675 min HPLC Rt=4.438 min

Example 11: (7S)-3-(3-aminoimidazo[1,2-a]pyridin-6-yl)-7-methyl-5-[4-(trifluoromethyl)phenyl]-6,7-dihydropyrazolo[1,5-a]pyrazin-4(5H)-one

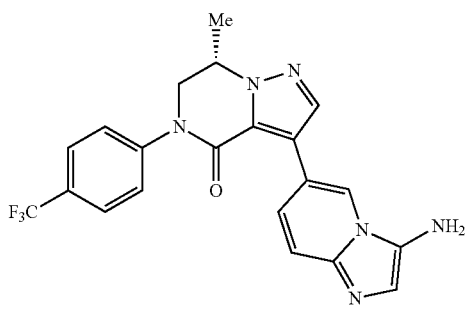 [SMILES: C[C@H]1CN(c2ccc(C(F)(F)F)cc2)C(=O)c2c(-c3ccc4ncc(N)n4c3)cnn21]

The compound of Reference example 8 (372 mg) was treated with 6-bromoimidazo[1,2-a]pyridin-3-amine (302 mg) in a similar manner to Example 10 to give the titled compound (87.5 mg).

$^1$H-NMR (400 MHz, CDCl$_3$) δ: 8.64 (1H, d, J=1.8 Hz), 7.79 (1H, s), 7.68 (2H, d, J=8.5 Hz), 7.49-7.46 (3H, m), 7.33 (1H, dd, J=9.2, 1.8 Hz), 7.16 (1H, s), 4.79-4.73 (1H, m), 4.26 (1H, dd, J=12.8, 4.3 Hz), 3.98 (1H, dd, J=12.8, 7.3 Hz), 3.25 (2H, brs), 1.73 (3H, d, J=6.7 Hz).

Example 12: (7S)-3-(imidazo[1,2-a]pyridin-6-yl)-7-methyl-5-[5-(trifluoromethyl)pyridin-2-yl]-6,7-dihydropyrazolo[1,5-a]pyrazin-4(5H)-one

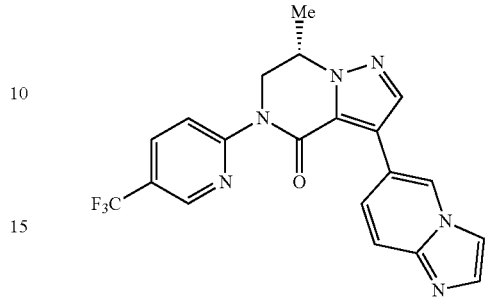

A mixture of 2-chloro-5-(trifluoromethyl)pyridine (345 mg), the compound of Reference example 7 (339 mg), tetrakis(triphenylphosphine)palladium (0) (147 mg), cesium carbonate (826 mg), and 4,5-bis(diphenylphosphino)-9,9-dimethylxanthene (147 mg) in 1,4-dioxane (3 mL) was heated to reflux with stirring for 5 hours. The reaction mixture was let cool to room temperature, and then diluted with ethyl acetate and filtered through Celite. To the filtrate was added saturated aqueous ammonium chloride solution, and the mixture was separated into layers. The organic layer was washed with brine, and then dried over anhydrous sodium sulfate, filtered, and concentrated under reduced pressure. The resulted residue was purified by amino silica gel column chromatography (hexane/ethyl acetate) to give the titled compound (414.9 mg).

LC-MS, m/z; 427[M+H]$^+$ retention time; 0.675 min $^1$H-NMR (400 MHz, CDCl$_3$) δ: 8.71 (2H, dd, J=11.0, 1.8 Hz), 8.21 (1H, d, J=9.2 Hz), 7.93 (1H, dd, J=8.9, 2.1 Hz), 7.77 (1H, s), 7.63-7.60 (3H, m), 7.40 (1H, dd, J=9.2, 1.8 Hz), 4.76-4.69 (2H, m), 4.39-4.34 (1H, m), 1.72 (3H, d, J=6.7 Hz).

Example 13: (7S)-3-(3-fluoroimidazo[1,2-a]pyridin-6-yl)-7-methyl-5-[4-(trifluoromethyl)phenyl]-6,7-dihydropyrazolo[1,5-a]pyrazin-4(5H)-one

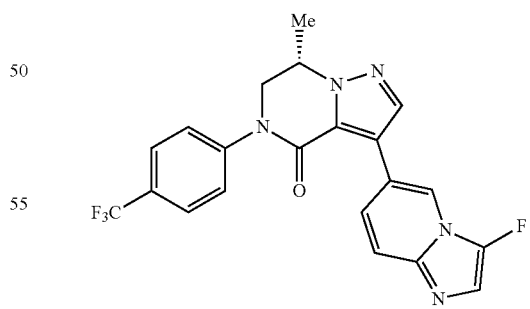

A mixture of the compound of Example 1 (544 mg) and 1-fluoro-4-methyl-1,4-diazoniabicyclo[2,2,2]octane bis(tetrafluoroborate) (634 mg) in acetonitrile (6 mL) was stirred at room temperature for 6 hours. To the reaction mixture was added saturated aqueous sodium thiosulfate solution, and the mixture was extracted with ethyl acetate. The organic layer was washed with saturated aqueous sodium hydrogen carbonate solution and brine, and then dried over anhydrous sodium sulfate, filtered, and concentrated under reduced pressure. The resulted residue was purified by silica gel column chromatography (hexane/ethyl acetate) to give the titled compound (21.8 mg).

$^1$H-NMR (400 MHz, DMSO-$d_6$) δ: 8.85 (1H, s), 8.11 (1H, s), 7.82 (2H, d, J=8.5 Hz), 7.68 (2H, d, J=8.5 Hz), 7.60 (1H, dd, J=9.8, 1.8 Hz), 7.52-7.51 (1H, m), 7.35 (1H, d, J=7.3 Hz), 4.85-4.83 (1H, m), 4.37 (1H, dd, J=12.8, 4.3 Hz), 4.09 (1H, dd, J=12.8, 7.3 Hz), 1.59 (3H, d, J=6.1 Hz).

Example 14: (7S)-7-methyl-3-(3-methylimidazo[1,2-a]pyridin-6-yl)-5-[4-(trifluoromethyl)phenyl]-6,7-dihydropyrazolo[1,5-a]pyrazin-4(5H)-one

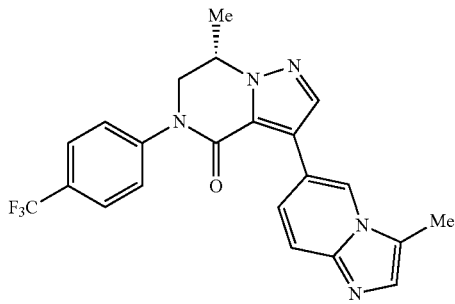 [SMILES: Cc1cnc2ccc(-c3cnn4c3C(=O)N(c3ccc(C(F)(F)F)cc3)C[C@@H]4C)cn12]

A mixture of the compound of Reference example 13 (219 mg), methylboronic acid (73.2 mg), tetrakis(triphenylphosphine)palladium (0) (47.1 mg), and sodium hydroxide (48.9 mg) in 1,2-dimethoxyethane (2 mL) and water (1 mL) was heated to reflux with stirring for 4 hours. The reaction mixture was let cool to room temperature, and then diluted with chloroform and filtered through Celite. To the filtrate was added saturated aqueous sodium hydrogen carbonate solution, and the mixture was separated into layers. The organic layer was washed with brine, and then dried over anhydrous sodium sulfate, filtered, and concentrated under reduced pressure. The resulted residue was purified by amino silica gel column chromatography (hexane/ethyl acetate) to give the titled compound (20.3 mg).

$^1$H-NMR (400 MHz, DMSO-$d_6$) δ: 8.75 (1H, s), 8.07 (1H, s), 7.82 (2H, d, J=7.9 Hz), 7.68 (2H, d, J=7.9 Hz), 7.54-7.52 (2H, m), 7.35 (1H, s), 4.84-4.83 (1H, m), 4.39-4.38 (1H, m), 4.09 (1H, dd, J=12.2, 7.9 Hz), 2.43 (3H, s), 1.59 (3H, d, J=6.1 Hz).

Example 15: (7S)-3-(3-ethylimidazo[1,2-a]pyridin-6-yl)-7-methyl-5-[4-(trifluoromethyl)phenyl]-6,7-dihydropyrazolo[1,5-a]pyrazin-4(5H)-one

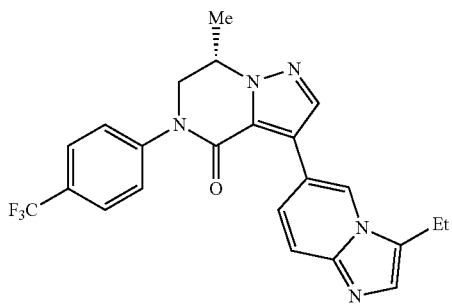 [SMILES: CCc1cnc2ccc(-c3cnn4c3C(=O)N(c3ccc(C(F)(F)F)cc3)C[C@@H]4C)cn12]

A mixture of the compound of Reference example 14 (87 mg) and 10% palladium-carbon (166 mg) in methanol (7 mL) was stirred under hydrogen atmosphere at room temperature for 3 hours. The reaction mixture was filtered through Celite, and the filtrate was concentrated under reduced pressure. The resulted residue was purified by amino silica gel column chromatography (hexane/ethyl acetate) to give the titled compound (46.9 mg).

$^1$H-NMR (400 MHz, DMSO-$d_6$) δ: 8.81 (1H, s), 8.07 (1H, s), 7.82 (2H, d, J=8.5 Hz), 7.68 (2H, d, J=8.5 Hz), 7.56-7.50 (2H, m), 7.36 (1H, s), 4.84-4.82 (1H, m), 4.38 (1H, dd, J=12.8, 4.3 Hz), 4.08 (1H, dd, J=12.8, 7.3 Hz), 2.83 (2H, a, J=7.5 Hz), 1.59 (3H, d, J=6.7 Hz), 1.30 (3H, t, J=7.5 Hz).

Example 16: (7S)-7-methyl-3-(3-propylimidazo[1,2-a]pyridin-6-yl)-5-[4-(trifluoromethyl)phenyl]-6,7-dihydropyrazolo[1,5-a]pyrazin-4(5H)-one

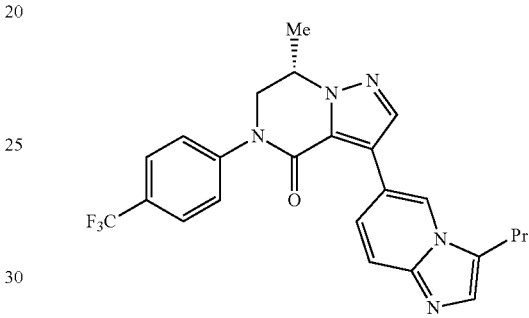

The compound of Reference example 15 (114.1 mg) was treated in a similar manner to Example 15 to give the titled compound (66.7 mg).

$^1$H-NMR (400 MHz, DMSO-$d_6$) δ: 8.81 (1H, s), 8.06 (1H, s), 7.81 (2H, d, J=8.5 Hz), 7.68 (2H, d, J=8.5 Hz), 7.52 (2H, s), 7.36 (1H, s), 4.85-4.81 (1H, m), 4.37 (1H, dd, J=13.1, 4.0 Hz), 4.08 (1H, dd, J=13.1, 7.6 Hz), 2.82 (2H, t, J=7.3 Hz), 1.74-1.66 (2H, m), 1.59 (3H, d, J=6.7 Hz), 0.95 (3H, t, J=7.3 Hz).

Example 17: (7S)-5-(4-fluoro-3-methylphenyl)-3-(imidazo[1,2-a]pyridin-6-yl)-7-methyl-6,7-dihydropyrazolo[1,5-a]pyrazin-4(5H)-one

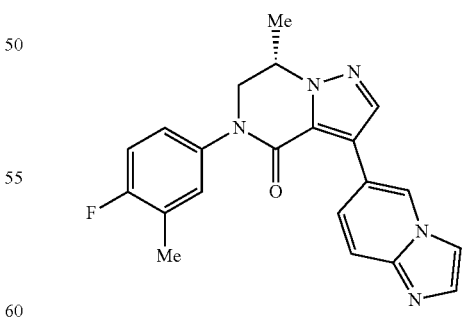

A mixture of the compound of Reference example 17 (161.8 mg), the compound of Reference example 6 (109 mg), palladium acetate (9.4 mg), S-phos (34.5 mg), and potassium carbonate (116 mg) in 1,2-dimethoxyethane (1.4 mL)/water (0.7 mL) was heated to reflux with stirring for 2 hours. The reaction mixture was let cool to room temperature, and then diluted with ethyl acetate and filtered through Celite. To the filtrate was added saturated aqueous sodium hydrogen carbonate solution, and the mixture was separated into layers. The organic layer was washed with brine, and then dried over anhydrous sodium sulfate, filtered, and concentrated under reduce pressure. The resulted residue was purified by silica gel column chromatography (hexane/ethyl acetate) to give the titled compound (109 mg).

$^1$H-NMR (400 MHz, CDCl$_3$) δ: 9.01 (1H, s), 7.80 (1H, s), 7.62-7.57 (3H, m), 7.46 (1H, dd, J=9.6, 1.4 Hz), 7.17-7.16 (1H, m), 7.10-7.07 (2H, m), 4.77-4.73 (1H, m), 4.19 (1H, dd, J=12.8, 4.1 Hz), 3.89 (1H, dd, J=12.8, 7.3 Hz), 2.28 (3H, d, J=1.8 Hz), 1.72 (3H, d, J=6.4 Hz).

Example 18: (7S)-3-(3-fluoroimidazo[1,2-a]pyridin-6-yl)-5-(4-fluoro-3-methylphenyl)-7-methyl-6,7-dihydropyrazolo[1,5-a]pyrazin-4 (5H)-one

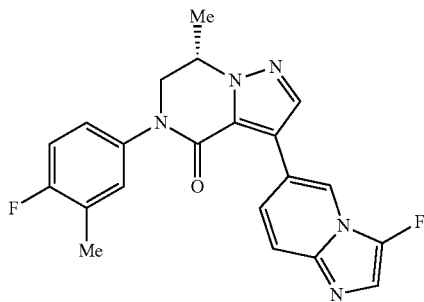 [SMILES: Cc1cc(N2C[C@H](C)n3ncc(-c4ccc5ncc(F)n5c4)c3C2=O)ccc1F]

The compound of Example 17 (81.4 mg) was treated in a similar manner to Example 13 to give the titled compound (4.2 mg).

$^1$H-NMR (400 MHz, CDCl$_3$) δ: 9.01 (1H, s), 8.12 (1H, d, J=9.8 Hz), 7.86 (1H, d, J=9.2 Hz), 7.80 (1H, s), 7.43 (1H, d, J=6.1 Hz), 7.11-7.00 (3H, m), 4.75-4.74 (1H, m), 4.17 (1H, dd, J=12.8, 4.3 Hz), 3.87 (1H, dd, J=12.8, 7.0 Hz), 2.24 (3H, d, J=1.8 Hz), 1.70 (3H, d, J=6.1 Hz).

Example 19: (7S)-5-(4-fluoro-3-methylphenyl)-7-methyl-3-(3-methylimidazo[1,2-a]pyridin-6-yl)-6,7-dihydropyrazolo[1,5-a]pyrazin-4(5H)-one

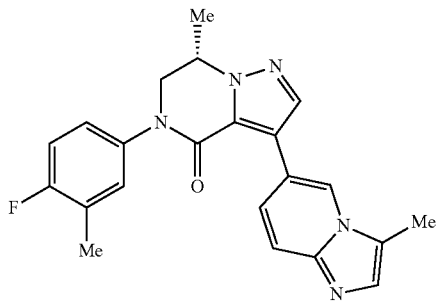 [SMILES: Cc1cc(N2C[C@H](C)n3ncc(-c4ccc5ncc(C)n5c4)c3C2=O)ccc1F]

To a mixture of the compound of Reference example 18 (30.0 mg) and bis-(tri-tert-butylphosphine)palladium (0) (6.12 mg) in THF (1.2 mL) was added methylzinc chloride (59.8 μL, 2.0M THF solution), and the mixture was stirred at room temperature for 5 hours. To the reaction mixture was added saturated aqueous ammonium chloride solution, and the mixture was extracted with ethyl acetate twice. The organic layers were combined, dried over anhydrous sodium sulfate, filtered, and concentrated under reduced pressure. The resulted residue was purified by amino silica gel column chromatography (hexane/ethyl acetate) to give the titled compound (16 mg).

$^1$H-NMR (400 MHz, CDCl$_3$) δ: 9.14 (1H, s), 8.18 (1H, d, J=9.1 Hz), 7.90 (1H, d, J=9.1 Hz), 7.83 (1H, s), 7.55 (1H, s), 7.11-7.00 (3H, m), 4.76-4.74 (1H, m), 4.17 (1H, dd, J=12.8, 4.1 Hz), 3.86 (1H, dd, J=12.8, 7.1 Hz), 2.52 (3H, s), 2.24 (3H, d, J=1.8 Hz), 1.70 (3H, d, J=6.4 Hz).

Tests

The following are pharmacological test methods and results for the present compound, but the present invention is not intended to be limited to these tests.

Test 1: Assessment with Human mGlu2 Receptor Stable Expressing Cells (1) Human mGlu2 Receptor Stable Expressing Cells Human mGlu2 receptor stable expressing cells were prepared, and used for incubation. Specifically, human mGlu2 receptor gene was inserted into pcDNA4/TO (K1020-01, Life technologies, Carlsbad, CA, USA), and introduced into TR-expressed human kidney-derived HEK cells (cat #CCL-82.2, ATCC, USA), followed by screening with Geneticin (cat #10131-027, Life technologies, Carlsbad, CA, USA), to obtain human mGlu2 receptor stable expressing cells.

High glucose-DMEM media (cat #11995-065, Life technologies, Carlsbad, CA, USA) containing 10% Dialysed-FBS (cat #26400-044, Life technologies, Carlsbad, CA, USA), 50 μg/mL Blasticidin S (cat #ANT-BL-1, Life technologies, Carlsbad, CA, USA), and 2 mg/mL G418 (cat #16513-84, nacalai tesque, Kyoto, Japan) were used for incubation on flasks for cell culture (cat #3133-150, AGC Thechno Glass, Shizuoka, Japan). During the incubation, cells were recovered by the treatment with TrypLE Express (cat #12604-013, Life technologies, Carlsbad, CA, USA), followed by subculture, every three to four days.

Cells were recovered by an about 80% confluency in the treatment with TrypLE Express three to four days after the subculture, transiently transfected with Gα16, apoaequorin, in media of Hanks (cat #14065-056, Life technologies, Carlsbad, CA, USA)/20 mmol/L HEPES (cat #15630-080, Life technologies, Carlsbad, CA, USA) Buffer (pH 7.4) containing 0.1% BSA (cat #12604-013, Life technologies, Carlsbad, CA, USA) and 0.1 pig/mL Tetracycline (cat #33031-64, nacalai tesque, Kyoto, Japan), and then seeded on a 384-well plate (cat #781090, Greiner bio-one, Frickenhausen, Germany) in 1,500 cells/30 μL/well.

Coelentetrazine h (cat #S2011, Promega, Madison, WI, USA) was added to the plate (10 μl/well) so as to be a final concentration of 1 μmol/L on the day after the seeding, and let stand for 4 hours or more at room temperature after centrifugation.

(2) Preparation of Test Compounds

A test compound was dissolved in DMSO so as to be a concentration 1000 times higher than the assessment concentration. This DMSO solution was diluted with a medium (Hanks, 20 mmol/L HEPES, 0.1% BSA) to a concentration 6 times higher than the assessment concentration. Glutamate was diluted with Hanks/20 mmol/L HEPES/0.1% BSA medium to a concentration 6 times higher than EC$_{80}$ concentration.

(3) Assessment of mGlu2 Receptor Negative Allosteric Modulator Activity

Human mGlu2 receptor stable expressing cells were prepared and incubated. Luminescence signals by mGlu2 receptor stimulation were detected with FDSS7000 (Hamamatsu Photonics). The compound solution prepared above was added to a plate where cells and luminescent substrates were added (10 μl/well). After 120 seconds of the addition, $EC_{80}$ Glutamate-containing solution was added thereto (10 μl/well), and luminescence signals were measured for 300 seconds after the addition (center wavelength: 465 nm) for calculation of RLU (Integration). mGlu2 receptor negative allosteric modulator activity of a compound was calculated by (100−100×(RLU of each compound and concentration)/(RLU of DMSO group)).

The present compound was assessed with the above biological test, and the compounds with mGlu2 receptor negative allosteric modulator activity were found out. mGlu2 receptor negative allosteric modulator activity ($IC_{50}$ value (nmol/L)) for each compound is shown in the following table.

| Example | mGluR2 NAM $IC_{50}$ (nM) or inhibition rate (%) |
|---|---|
| 1 | 18 |
| 2 | 11 |
| 3 | 23 |
| 4 | 33 |
| 5 | 18 |
| 6 | 26 |
| 7 | 11 |
| 8 | 19 |
| 9 | 61 |
| 10 | 302 |
| 11 | 78 |
| 12 | 16 |
| 13 | 7.9 |
| 14 | 9.1 |
| 15 | 7.8 |
| 16 | 13 |
| 17 | 17 |
| 18 | 6.9 |
| 19 | 16 |

(4) Assessment of Time-Dependent mGlu2 Receptor Negative Allosteric Modulator Activity Human mGlu2 receptor stable expressing cells are prepared and incubated. Luminescence signals by mGlu2 receptor stimulation are detected with FDSS7000 (Hamamatsu Photonics). The test compound solution prepared in the above (2) is added to a plate where cells and luminescent substrates are added (10 μl/well). After 2, 15, 30, 60, and 120 minutes of the addition, $EC_{80}$ Glutamate-containing solution is added thereto (10 μl/well), and luminescence signals are measured for 300 seconds after the addition (center wavelength: 465 nm) for calculation of RLU (Integration). mGlu2 receptor negative allosteric modulator activity of a compound at each time for addition is calculated by (100−100×(RLU of each compound and concentration)/(RLU of DMSO group)).

Test 2: Rat Forced Swimming Test

Existing antidepressants such as tricyclic antidepressants and serotonin reuptake inhibitors are known to shorten the immobility time in the forced swimming test in rats. This test system is used to assess the antidepressant-like effect of the present compound based on the immobility time.

7-Week-old male Wistar rats are used for the rat forced swimming test. Specifically, animals are put into a tank filled with 5.8 L of tap water (water temperature 25±1° C.), and then forced to swim for 15 minutes (swimming training). After the swimming training, animals are wiped dry and return to the homecage. On the day after the swimming training, the swim test is performed for 5 minutes in the same manner as the swimming training. Swimming behaviors of each individual are recorded with a video camera through the side of tank. After the swimming test, animals are wiped dry and return to the homecage. A test compound or a positive control, imipramine, is suspended in a 0.5% methylcellulose solution for oral administration. A vehicle or a test compound is administered 15 minutes after finishing the swim training and 2 hours before the swimming test. Imipramine is administered 15 minutes after finishing the swim training and 1 hour before the swimming test. Immobility is defined as the condition where an animal is floated without moving its forepaws and body in a tank, and the cumulative time of immobility during the 5-minute swimming test is measured as the immobility time of the individual. Student's t-test and Dunnett's multiple comparison are used for statistical processing.

Test 3: Enhancing Effect of Electrocortico γ-Frequency Band Power in Rats

Changes in γ-frequency band power in electrocorticogram are considered as an index of cortical activity, and mGluR2 antagonists, NAM, or NMDA receptor antagonists (such as Ketamine) are known to enhance γ-frequency band power. The present compound is assessed, whether to show enhancing γ-frequency band power.

The test is performed in the dark period by using male Wistar rats, which electroencephalogram measurement electrods are implanted. A compound is suspended in a 0.5% methylcellulose solution for oral administration. Measurement of electroencephalogram and frequency analyses are carried out according to the method described in Progress in Neuro-Psychopharmacology & Biological Psychiatry 63 (2015) 6-13. Frequency of electroencephalogram is analyzed between 0.5 and 80 Hz, and the frequency band between 30 and 80 Hz is defined as the γ frequency to calculate the power value. The power change is measured every 1 hour until 2 hours after administration as an index of the value before administration as 100%. In view of duplicate measurement, the power changes are statistically compared using repeated measures two-way ANOVA followed by post hoc Dunnett tests.

Test 4: Assessment of MBI and enzyme inactivation clearance against CYP3A4

Cytochrome P450 (hereinafter called CYP) is the most important enzyme group associated with drug metabolism, and most of pharmacokinetic interactions are based on the inhibition of the CYP activities. CYP includes multiple molecular species. In particular, CYP3A4 is most involved in drug metabolism in oxidation reaction with CYP, and accounts for a major portion of CYPs existing in the liver.

CYP inhibition is generally divided into two types consisting of "reversible inhibition" and "irreversible inhibition (mechanism-based inhibition: MBI)". In particular, CYP inhibition based on the MBI is known to have a possibility to cause severe side effects such as hepatotoxicity as well as drug-drug interactions (Curr Opin Drug Discov Devel. 2010 January, 13(1), 66-77, Therapeutics and Clinical Risk Management, 2005, 1(1), 3-13).

MBI and enzyme inactivation clearance against CYP3A4 were evaluated for example compounds.

Inhibition effects and inhibition types of test compounds to CYP3A4 were evaluated using human liver microsomes as an enzyme source and midazolam or testosterone as a substrate of CYP3A4. After metabolic reaction for 30 minutes at 37° C., metabolites of CYP3A4 substrate in the presence or absence of a test compound (at 4 concentrations) were measured by LC-MS/MS, and the inhibition rates were calculated from the ratios of peak area. $IC_{50}$ values were calculated from plots of test compound concentrations. It was known that when a test compound has MBI potential, $IC_{50}$ value is lowered by starting metabolic reactions after preincubation in the presence of NADPH (cofactor). Therefore, it was determined that there was MBI potential when the shift in $IC_{50}$ values due to preincubation was 2-fold or more (Xenobiotica, 2009, 39(2), 99-112).

When MBI potential was determined, $k_{inact}$ (maximum inactivation rate constant) and $K_I$ (inactivator concentration yielding a measured inactivation rate at half of $k_{inact}$) were calculated by the non-linear least-squares method. Enzyme inactivation clearance was calculated according to the method described in Drug Metabolism and Disposition, 2011, 39(7), 1247-1254 ($CL_{int}=k_{inact}/K_I$(ml/min/mmol)× CYP contents (pmol/mg protein)).

MBI and enzyme inactivation clearance against CYP3A4 for each Example compound are shown in the following table.

| Example | CYP3A4 MBI | Enzyme inactivation clearance (µL/min/mg protein) |
|---|---|---|
| 1 | N.D. | 0 |
| 2 | N.D. | 0 |
| 3 | N.D. | 0 |
| 4 | N.D. | 0 |
| 5 | N.D. | 0 |
| 6 | N.D. | 0 |
| 7 | 4.5 | 2.146 |
| 8 | 2.2 | 0.601 |
| 9 | N.D. | 0 |
| 11 | N.D. | 0 |
| 12 | 2.2 | 0.159 |
| 13 | N.D. | 0 |
| 14 | N.D. | 0 |
| 15 | N.D. | 0 |
| 16 | N.D. | 0 |
| 17 | 3.2 | 1.942 |
| 18 | N.D. | 0 |
| 19 | N.D. | 0 |

INDUSTRIAL APPLICABILITY

As explained above, the present compound shows negative allosteric modulation against Group II metabotropic glutamate (mGlu) receptors. The present compound is, therefore, useful as a therapeutic agent and/or preventive agent for diseases involving metabotropic glutamate receptor subtype 2 (mGluR2) and/or metabotropic glutamate receptor subtype 3 (mGluR3).

The invention claimed is:
1. A process for preparing a compound of Formula (1a):

(1a)

or a pharmaceutically acceptable salt thereof, wherein:

X is CH or N;

$R^3$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents;

$R^4$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents;

$R^5$ is H, halogen, $C_{1-6}$ alkyl, or $NH_2$; and $R^6$ is H, halogen, $C_{1-6}$ alkyl, or $NH_2$;

wherein the process comprises the following steps:

A1) reacting a compound of Formula (4a):

(4a)

wherein:

PG is a protecting group selected from the group consisting of $CH_2$-phenyl, $C(O)CH_3$, $C(O)OC(CH_3)_3$ and $C(O)OCH_2$-phenyl;

with a compound of Formula (3):

(3)

wherein:

$R_7$ is $CH_3$ or $CH_2CH_3$;

in the presence of (i) $P(Ph)_3$ or $P(CH_2CH_2CH_2CH_3)_3$ and a Mitsunobu reaction reagent selected from the group consisting of diethyl azodicarboxylate, diisopropyl azodicarboxylate, and N,N,N',N'-tetramethylazodicarboxamide, or (ii) cyanomethylenephosphorane, to give a compound of Formula (6a):

(6a)

wherein:

$R_7$ is $CH_3$ or $CH_2CH_3$; and

PG is a protecting group selected from the group consisting of $CH_2$-phenyl, $C(O)CH_3$, $C(O)OC(CH_3)_3$ and $C(O)OCH_2$-phenyl;

A2) cyclizing the compound of Formula (6a) above in the presence of an acid or a base, to give a compound of Formula (7a):

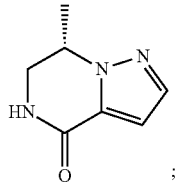
(7a)

A3) coupling the compound of Formula (7A) above with a compound of Formula (8a):

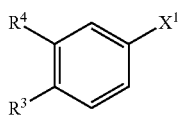
(8a)

wherein:
 $R^3$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents;
 $R^4$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents; and
 $X^1$ is Cl, Br, or I;
in the presence of a transition metal catalyst selected from the group consisting of palladium (II) acetate, tris(dibenzylideneacetone)dipalladium(0), bis(tri-tert-butylphosphine)palladium(0), copper (I) iodide, and copper (II) oxide, to give a compound of Formula (9a):

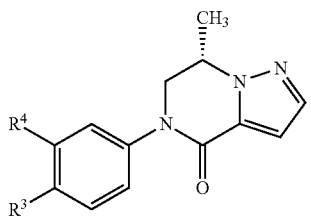
(9a)

wherein:
 $R^3$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents;
 $R^4$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents;

A4) reacting the compound of Formula (9a) above with a halogenating agent selected from the group consisting of bromine, iodine, iodine monochloride, 1,3-diiodo-5, 5-dimethylhydantoin, N-chlorosuccinimide, N-bromosuccinimide, and N-iodosuccinimide, to give a compound of Formula (15a):

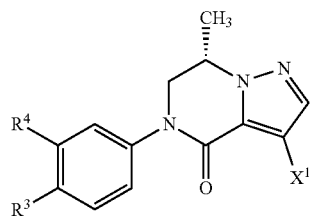
(15a)

wherein:
 $R^3$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents;
 $R^4$ is H, halogen, $C_{1-6}$ alkyl, or $C_{1-4}$ alkoxy, wherein the $C_{1-6}$ alkyl or $C_{1-4}$ alkoxy is optionally substituted with 1, 2, 3, 4, or 5 independently selected halogen substituents; and
 $X^1$ is Cl, Br, or I;

A5) coupling the compound of Formula (15a) above with a compound of Formula (16):

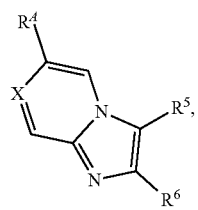
(16)

or a pharmaceutically acceptable salt thereof,
wherein:
 X is CH or N;
 $R^5$ is H, halogen, $C_{1-6}$ alkyl, or $NH_2$;
 $R^6$ is H, halogen, $C_{1-6}$ alkyl, or $NH_2$; and
 $R^A$ is $B(OH)_2$ or a boronic acid ester;
in the presence of a transition metal catalyst selected from the group consisting of tetrakis(triphenylphosphine)palladium(0), palladium (II) acetate, palladium (II) chloride, tris(dibenzylideneacetone)dipalladium (0), dichlorobis(triphenylphosphine) palladium (II), dichloro[1,1'-bis(diphenylphosphino)ferrocene]palladium (II) dichloromethane adduct, and dichlorobis(di-tert-butyl(4-dimethylamnophenyl)phosphino)palladium (II), to give the compound of Formula (1a) above; and A6) optionally dissolving or suspending the compound of Formula (Ia) above in an organic solvent, followed by adding a pharmaceutically acceptable acid or base selected from the group consisting of (a), (b), (c), (d), (e), and (f):
 (a) an organic acid selected from the group consisting of acetic acid, trifluoroacetic acid, maleic acid, fumaric acid, citric acid, tartaric acid, methanesulfonic acid, benzenesulfonic acid, formic acid, and para-toluenesulfonic acid;
 (b) an inorganic acid selected from the group consisting of hydrochloric acid, hydrobromic acid, hydroiodic acid, sulfuric acid, nitric acid, and phosphoric acid;
 (c) an amino acid selected from the group consisting of arginine, lysine, ornithine, asparagine acid, and glutamic acid;

(d) a metal selected from the group consisting of sodium, potassium, calcium, magnesium, barium, and aluminum;

(e) an ammonium salt; and (f) an organic base selected from the group consisting of trimethylamine, triethylamine, pyridine, picoline, 2,6-lutidine, ethanolamine, diethanolamine, triethanolamine, tromethamine, tris(hydroxymethyl)methylamine, tert-butylamine, cyclohexylamine, dicyclohexylamine, and N,N'-dibenzylethylenediamine, to give a pharmaceutically acceptable salt of the compound of Formula (1a) above.

2. The process according to claim 1, wherein PG is a protecting group selected from the group consisting of $CH_2$-phenyl and $C(O)CH_3$.

3. The process according to claim 1, wherein PG is a protecting group selected from the group consisting of $C(O)OC(CH_3)_3$ and $C(O)OCH_2$-phenyl.

4. The process according to claim 1, wherein:

$R^3$ is H, F, Cl, $CHF_2$, $CF_3$, or $OCHF_2$;

$R^4$ is H, F, Cl, $CHF_2$, $CF_3$, or $OCHF_2$;

$R^5$ is H or $NH_2$; and $R^6$ is H or $NH_2$.

5. The process according to claim 1, wherein the compound of Formula (Ia) is selected from the group consisting of:

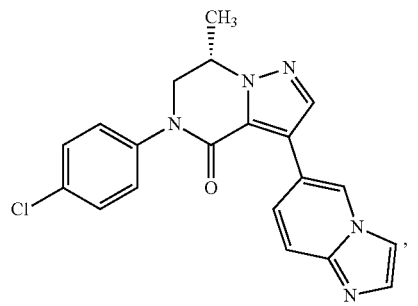

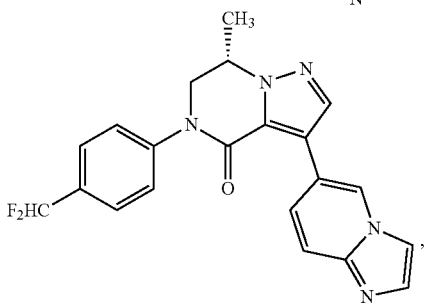

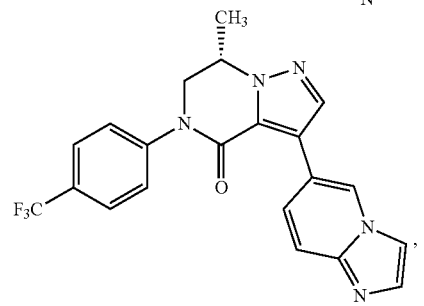

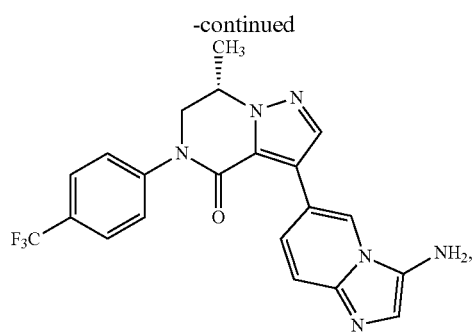

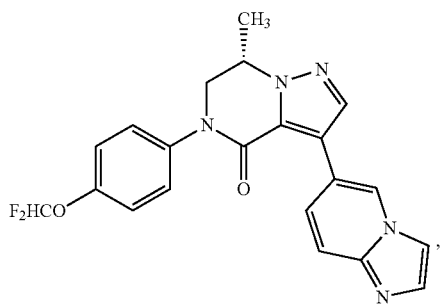

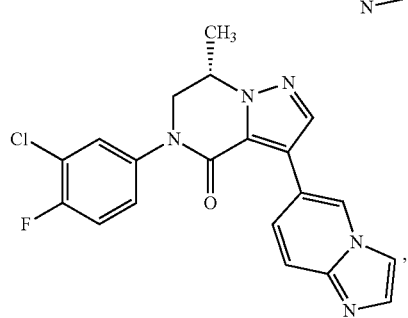

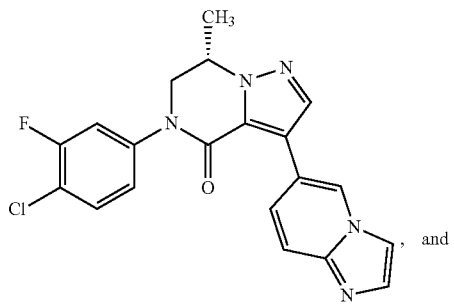

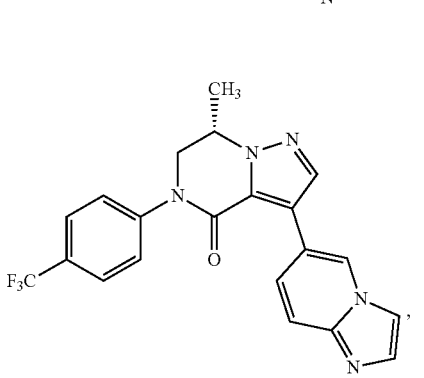

or a pharmaceutically acceptable salt thereof.

6. The process according to claim 1, wherein the compound of Formula (Ia) is selected from the group consisting of:

71
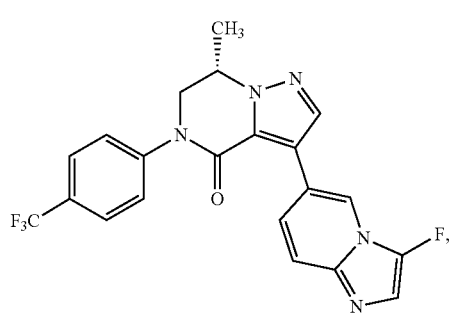
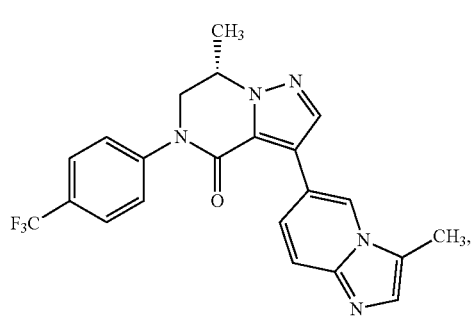
72
-continued
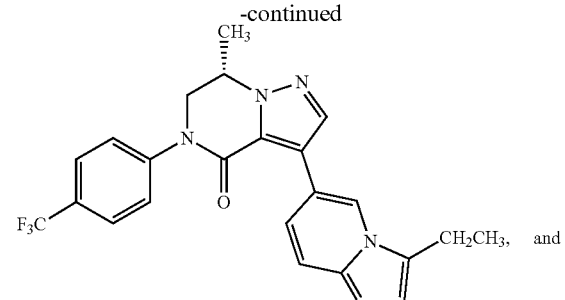
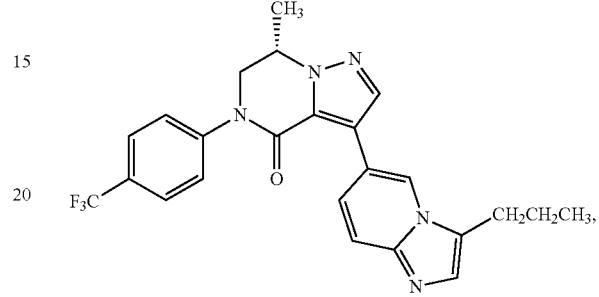
or a pharmaceutically acceptable salt thereof.
* * * * *